(12) United States Patent
Yamada et al.

(10) Patent No.: US 10,155,952 B2
(45) Date of Patent: Dec. 18, 2018

(54) METHOD FOR PRODUCING TARGET SUBSTANCE

(71) Applicant: AJINOMOTO CO., INC., Tokyo (JP)

(72) Inventors: Kazuteru Yamada, Kanagawa (JP); Yoshihiko Hara, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 205 days.

(21) Appl. No.: 15/134,674

(22) Filed: Apr. 21, 2016

(65) Prior Publication Data
US 2016/0222394 A1 Aug. 4, 2016

Related U.S. Application Data

(63) Continuation of application No. PCT/JP2014/078234, filed on Oct. 23, 2014.

(30) Foreign Application Priority Data

Oct. 23, 2013 (JP) .................. 2013-220609

(51) Int. Cl.
| | |
|---|---|
| C12N 15/77 | (2006.01) |
| C12P 19/32 | (2006.01) |
| C12P 21/02 | (2006.01) |
| C07K 14/34 | (2006.01) |
| C12N 1/20 | (2006.01) |
| C12P 19/34 | (2006.01) |
| C12P 19/40 | (2006.01) |
| C12N 9/00 | (2006.01) |
| C12N 9/12 | (2006.01) |
| C12N 9/88 | (2006.01) |
| C12N 9/92 | (2006.01) |
| C12P 13/04 | (2006.01) |
| C12N 9/02 | (2006.01) |

(52) U.S. Cl.
CPC .............. *C12N 15/77* (2013.01); *C07K 14/34* (2013.01); *C12N 1/20* (2013.01); *C12N 9/0008* (2013.01); *C12N 9/1205* (2013.01); *C12N 9/88* (2013.01); *C12N 9/92* (2013.01); *C12P 13/04* (2013.01); *C12P 19/32* (2013.01); *C12P 19/34* (2013.01); *C12P 19/40* (2013.01); *C12P 21/02* (2013.01); *C12Y 102/01026* (2013.01); *C12Y 207/01017* (2013.01); *C12Y 402/01082* (2013.01); *C12Y 503/01005* (2013.01)

(58) Field of Classification Search
None
See application file for complete search history.

(56) References Cited

U.S. PATENT DOCUMENTS

| | | |
|---|---|---|
| 5,168,056 A | 12/1992 | Frost |
| 5,776,736 A | 7/1998 | Frost et al. |
| 5,906,925 A | 5/1999 | Liao |
| 8,404,474 B2 | 3/2013 | Kozlov et al. |
| 8,728,774 B2 | 5/2014 | Rybak et al. |
| 8,753,849 B2 | 6/2014 | Kozlov et al. |
| 8,785,161 B2 | 7/2014 | Rybak et al. |
| 8,969,048 B2 | 3/2015 | Kozlov et al. |
| 9,045,789 B2 | 6/2015 | Nishio et al. |
| 2005/0014234 A1 | 1/2005 | Zelder et al. |
| 2013/0295621 A1 | 11/2013 | Nishio et al. |
| 2014/0287472 A1 | 9/2014 | Rybak |
| 2014/0377816 A1 | 12/2014 | Rah et al. |
| 2015/0259717 A1 | 9/2015 | Hara et al. |

FOREIGN PATENT DOCUMENTS

| | | |
|---|---|---|
| EP | 1577396 | 9/2005 |
| JP | 09-507386 | 7/1997 |
| JP | 11-506934 | 6/1999 |
| WO | WO95/017517 | 6/1995 |
| WO | WO96/040970 | 12/1996 |
| WO | WO 96/040970 | 12/1996 |
| WO | WO03/040181 A2 | 5/2003 |
| WO | WO2007/086608 A1 | 8/2007 |
| WO | WO2011/123154 A2 | 10/2011 |
| WO | WO2011/163128 A1 | 12/2011 |
| WO | WO2013/069634 | 5/2013 |
| WO | WO2013/105802 | 7/2013 |

OTHER PUBLICATIONS

International Preliminary Report on Patentability for PCT Patent App. No. PCT/JP2014/078234 (dated Oct. 23, 2014).
Brinkrolf, K., et al., "The transcriptional regulatory repertoire of *Corynebacterium glutamicum*: Reconstruction of the network controlling pathways involved in lysine and glutamate production," J. Biotechnol. 2010;149:173-182.
Gonzalez, R., et al., "Global Gene Expression Differences Associated with Changes in Glycolytic Flux and Growth Rate in *Escherichia coli* during the Fermentation of Glucose and Xylose," Biotechnol. Prog. 2002;18:6-20.
Gopinath, V., et al., "Amino acid production from rice straw and wheat bran hydrolysates by recombinant pentose-utilizing *Corynebacterium glutamicum*," Appl. Microbiol. Biotechnol. 2011;92:985-996.
International Search Report for PCT Patent App. No. PCT/JP2014/078234 (dated Jan. 27, 2015).
Nichols, N. N., et al., "Use of catabolite repression mutants for fermentation of sugar mixtures to ethanol," Appl. Microbiol. Biotechnol. 2001;56;120-125.

(Continued)

*Primary Examiner* — Suzanne M Noakes
(74) *Attorney, Agent, or Firm* — Cermak Nakajima & McGowan LLP; Shelly Guest Cermak

(57) ABSTRACT

A method for producing a target substance is provided. A target substance is produced by culturing a coryneform bacterium, which is able to produce a target substance, and which also has an improved ability to assimilate xylose as a result of the introduction of a mutation into a coding region and/or an expression control region of the NCgl2954 gene on the chromosome of the bacterium. The culture is conducted in a medium containing xylose, and the target substance can be collected from the medium.

21 Claims, 6 Drawing Sheets

Specification includes a Sequence Listing.

(56) References Cited

OTHER PUBLICATIONS

Tao, H., et al., "Engineering a Homo-Ethanol Pathway in *Escherichia coli*: Increased Glycolytic Flux and Levels of Expression of Glycolytic Genes during Xylose Fermentation," J. Bacteriol. 2001;183(10):2979-2988.

Zahoor, A., et al., "Metabolic Engineering of Corynebacterium Glutamicum Aimed at Alternative Carbon Sources and New Products," Computational and Structural Biotechnology Journal 2012;3(4):1-11.

Database UniProt [Online], entered Dec. 9, 2015, retrieved from EBI accession No. UNIPROT:A0A0M4CP06 on Jan. 26, 2017, Database accession No. A0A0M4CP06.

Kawaguchi, H., et al., "Engineering of a Xylose Metabolic Pathway in Corynebacterium glutamicum," Applied and Environmental Microbiology 2006;72(5):3418-3428.

Zhou, Z., et al., "*Corynebacterium desert* sp. nov., isolated from desert sand," International Journal of Systematic and Evolutionary Microbiology 2012;62:791-794.

Extended European Search Report for European Patent App. No. 14856074.1 (dated Feb. 14, 2017).

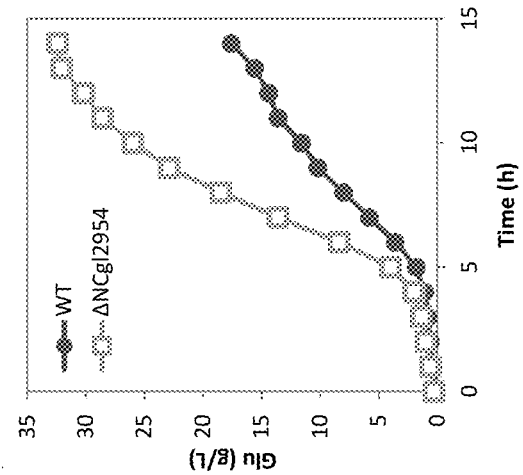
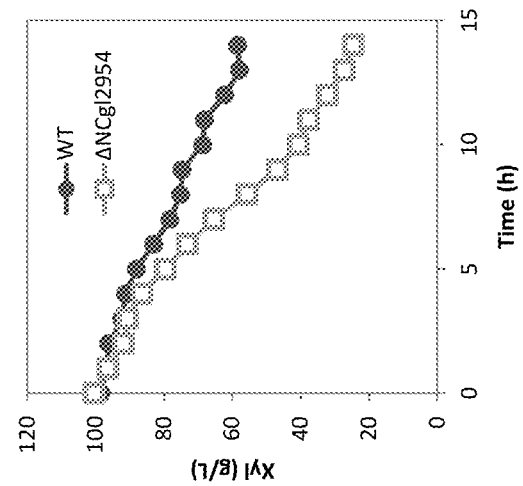
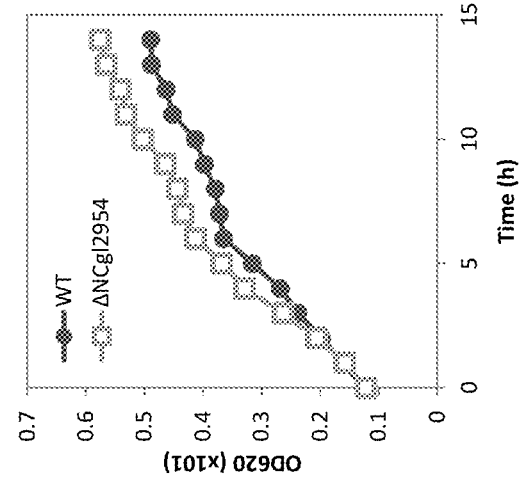
Fig. 8(A)
Fig. 8(B)
Fig. 8(C)

METHOD FOR PRODUCING TARGET SUBSTANCE

This application is a Continuation of, and claims priority under 35 U.S.C. § 120 to, International Application No. PCT/JP2014/078234, filed Oct. 23, 2014, and claims priority therethrough under 35 U.S.C. § 119 to Japanese Patent Application No. 2013-220609, filed Oct. 23, 2013, the entireties of which are incorporated by reference herein. Also, the Sequence Listing filed electronically herewith is hereby incorporated by reference (File name: 2016-04-21T_US-546_Seq_List; File size: 128 KB; Date recorded: Apr. 21, 2016).

BACKGROUND OF THE INVENTION

Field of the Invention

The present invention relates to a method for producing target substances such as L-amino acids using a coryneform bacterium. L-Amino acids are industrially useful as additives for animal feeds, ingredients of seasonings, foods and drinks, amino acid infusion solutions, and so forth.

Brief Description of the Related Art

L-Amino acids are industrially produced by, for example, fermentation using various microorganisms having an L-amino acid-producing ability. Examples of methods for producing an L-amino acid by fermentation include, for example, using a wild-type microorganism (wild-type strain), using an auxotrophic strain derived from a wild-type strain, using a metabolic regulation mutant strain derived as a mutant strain resistant to any of various drugs from a wild-type strain, and using a strain having characteristics of both an auxotrophic strain and metabolic regulation mutant strain.

Further, in recent years, microorganisms of which an L-amino acid-producing ability is improved by recombinant DNA techniques are used for the L-amino acid production. Examples of methods for improving an L-amino acid-producing ability of a microorganism include, for example, enhancing the expression of a gene encoding an L-amino acid biosynthetic enzyme (U.S. Pat. No. 5,168,056 and U.S. Pat. No. 5,776,736), and enhancing inflow of a carbon source into an L-amino acid biosynthesis system (U.S. Pat. No. 5,906,925).

In the conventional industrial production of target substances such as L-amino acids by fermentation, glucose, fructose, sucrose, blackstrap molasses, starch hydrolysates and so forth have been used as the carbon source. However, they are relatively expensive, and use of biomass raw materials derived from plants has also been advanced in recent years.

Although raw materials consisting of edible portions such as starch and fats and oils are mainly used as such biomass raw materials at present, it is desired to use biomass raw materials consisting of non-edible portions such as cellulose, hemicellulose, and lignin in future. Cellulose and hemicellulose are converted into pentoses and hexoses through a pretreatment using heat or acid, and a saccharification treatment using an enzyme such as cellulase, and they can be used as a raw material for fermentation (Japanese Patent Laid-open (Kohyo) No. 9-507386 and Japanese Patent Laid-open (Kohyo) No. 11-506934). It is known that if mixed saccharides of such pentoses and hexoses are used as the raw material for amino acid fermentation etc., *Escherichia coli* preferentially assimilates glucose, and as a result, phenomena of two-step proliferation (diauxy), and delayed growth have been confirmed (Nichols N. N. et al., Appl. Microbiol. Biotechnol., 2001 July, 56(1-2):120-1251 and Gonzalez, R., Biotechnol. Prog., 2002 January-February, 18(1):6-20)

In *Escherichia coli*, a xylose assimilation pathway including xylose isomerase encoded by the xylA gene and xylulokinase encoded by the xylB gene is known, and it is also known that an L-amino acid can be produced from xylose by using *Escherichia coli* or *Corynebacterium glutamicum* into which this pathway has been introduced (Tao H., et al., J. Bacteriol., 2001 May, 183(10):2979-2988 and Gopinath, V et al., Appl. Microbiol. Biotechnol., 2011 December, 92(5): 985-96, European Patent No. 1577396 and WO2013/105802). As xylose assimilation pathway, there is also known another pathway in which xylose is converted into α-ketoglutaric acid via xylonic acid, and it is known that a target substance such as L-glutamic acid can be produced from xylose by using a bacterium into which this pathway has been introduced (WO2013/069634).

The NCgl2954 gene of *Corynebacterium glutamicum* is a gene encoding a transcription factor. However, a connection between the NCgl2954 gene and xylose assimilability has not been previously reported.

SUMMARY OF THE INVENTION

Aspects of the present invention include development of a novel technique for improving xylose assimilability of coryneform bacteria, and thereby provide a method for efficiently producing target substances such as L-amino acids and nucleic acids from a raw material containing xylose.

Coryneform bacteria into which a mutation was introduced into the NCgl2954 gene and coryneform bacteria deficient in the NCgl2954 gene were found to be able to efficiently assimilate xylose.

It is an aspect of the present invention to provide a method for producing a target substance comprising:
culturing a coryneform bacterium having an ability to produce a target substance in a medium containing xylose to produce and accumulate the target substance in the medium; and
collecting the target substance from the medium,
wherein the ability of the bacterium to assimilate xylose has been improved by introduction of a mutation into a coding region and/or an expression control region of the NCgl2954 gene on the chromosome of the bacterium.

It is a further aspect of the present invention to provide a method as described above, wherein the ability of the bacterium to assimilate xylose has been improved by improving the ability of the bacterium to take up xylose.

It is a further aspect of the present invention to provide a method as described above, wherein the ability of the bacterium to assimilate xylose has been improved by attenuation of expression of the NCgl2954 gene, or disruption of the gene.

It is a further aspect of the present invention to provide a method as described above, wherein the NCgl2954 gene is a DNA encoding a protein selected from the group consisting of:
(A) a protein comprising the amino acid sequence of SEQ ID NO: 14;
(B) a protein comprising the amino acid sequence of SEQ ID NO: 14, but which includes substitution, deletion, insertion, or addition of one or several amino acid residues, and wherein when said protein is deleted from the coryneform bacterium, the bacterium has an improved ability to assimilate xylose; and (C) a protein comprising an amino acid sequence having an identity of 90% or higher to the amino acid sequence of SEQ ID NO: 14, and wherein when said protein is deleted from the coryneform bacterium, the bacterium has an improved ability to assimilate xylose.

It is a further aspect of the present invention to provide a method as described above, wherein the mutation is selected from the group consisting of:

(1) replacement of an amino acid residue corresponding to the leucine residue at position 438 of SEQ ID NO: 14 with an amino acid residue other than leucine residue;

(2) replacement of an amino acid residue corresponding to the tryptophan residue at position 274 of SEQ ID NO: 14 with an amino acid residue other than tryptophan residue;

(3) replacement of an amino acid residue corresponding to the tyrosine residue at position 377 of SEQ ID NO: 14 with an amino acid residue other than tyrosine residue;

(4) replacement of an amino acid residue corresponding to the leucine residue at position 365 of SEQ ID NO: 14 with an amino acid residue other than leucine residue;

(5) replacement of an amino acid residue corresponding to the leucine residue at position 366 of SEQ ID NO: 14 with an amino acid residue other than leucine residue;

(6) replacement of an amino acid residue corresponding to the alanine residue at position 367 of SEQ ID NO: 14 with an amino acid residue other than alanine residue;

(7) truncation of the N-terminus amino acid residues beginning with the amino acid residue at position 368 of SEQ ID NO: 14; and (8) combinations thereof.

It is a further aspect of the present invention to provide a method as described above, wherein said amino acid residue other than leucine residue at position 438 of SEQ ID NO: 14 is proline;

said amino acid residue other than tryptophan residue is arginine;

said amino acid residue other than tyrosine residue is asparagine;

said amino acid residue other than leucine residue at position 365 of SEQ ID NO: 14 is serine;

said amino acid residue other than leucine residue at position 366 of SEQ ID NO: 14 is arginine; and said amino acid residue other than alanine residue is phenylalanine.

It is a further aspect of the present invention to provide a method as described above, wherein the bacterium has been further modified so that activities or activity of xylose isomerase and/or xylulokinase is increased.

It is a further aspect of the present invention to provide a method as described above, wherein the xylose isomerase is a protein selected from the group consisting of:

(A) a protein comprising the amino acid sequence of SEQ ID NO: 11;

(B) a protein comprising the amino acid sequence of SEQ ID NO: 11, but which includes substitution, deletion, insertion, or addition of one or several amino acid residues, and wherein said protein has xylose isomerase activity; and (C) a protein comprising an amino acid sequence having an identity of 90% or higher to the amino acid sequence of SEQ ID NO: 11, and wherein said protein has xylose isomerase activity.

It is a further aspect of the present invention to provide a method as described above, wherein the xylulokinase is a protein selected from the group consisting of:

(A) a protein comprising the amino acid sequence of SEQ ID NO: 12;

(B) a protein comprising the amino acid sequence of SEQ ID NO: 12, but which includes substitution, deletion, insertion, or addition of one or several amino acid residues, and wherein said protein has xylulokinase activity; and (C) a protein comprising an amino acid sequence having an identity of 90% or higher to the amino acid sequence of SEQ ID NO: 12, and wherein said protein has xylulokinase activity.

It is a further aspect of the present invention to provide a method as described above, wherein the bacterium has been further modified so that activity or activities of an enzyme selected from the group consisting of xylose dehydrogenase, xylonolactonase, xylonate dehydratase, 2-keto-3-deoxyxylonate dehydratase, α-ketoglutaric semialdehyde dehydrogenase, and combinations thereof is/are increased.

It is a further aspect of the present invention to provide a method as described above, wherein the xylonate dehydratase, 2-keto-3-deoxyxylonate dehydratase, and α-ketoglutaric semialdehyde dehydrogenase are derived from an *Escherichia* bacterium, *Sphingomonas* bacterium, and *Bacillus* bacterium, respectively.

It is a further aspect of the present invention to provide a method as described above, wherein the xylose dehydrogenase is a protein selected from the group consisting of:

(A) a protein comprising the amino acid sequence of SEQ ID NO: 16 or 42;

(B) a protein comprising the amino acid sequence of SEQ ID NO: 16 or 42, but which includes substitution, deletion, insertion, or addition of one or several amino acid residues, and wherein said protein has xylose dehydrogenase activity; and (C) a protein comprising an amino acid sequence having an identity of 90% or higher to the amino acid sequence of SEQ ID NO: 16 or 42, and wherein said protein has xylose dehydrogenase activity.

It is a further aspect of the present invention to provide a method as described above, wherein the xylonolactonase is a protein selected from the group consisting of:

(A) a protein comprising the amino acid sequence of SEQ ID NO: 18 or 44;

(B) a protein comprising the amino acid sequence of SEQ ID NO: 18 or 44, but which includes substitution, deletion, insertion, or addition of one or several amino acid residues, and wherein said protein has xylonolactonase activity; and (C) a protein comprising an amino acid sequence having an identity of 90% or higher to the amino acid sequence of SEQ ID NO: 18 or 44, and wherein said protein has xylonolactonase activity.

It is a further aspect of the present invention to provide a method as described above, wherein the xylonate dehydratase is a protein selected from the group consisting of:

(A) a protein comprising the amino acid sequence of SEQ ID NO: 20 or 46;

(B) a protein comprising the amino acid sequence of SEQ ID NO: 20 or 46, but which includes substitution, deletion, insertion, or addition of one or several amino acid residues, and wherein said protein has xylonate dehydratase activity; and (C) a protein comprising an amino acid sequence having an identity of 90% or higher to the amino acid sequence of SEQ ID NO: 20 or 46, and wherein said protein has xylonate dehydratase activity.

It is a further aspect of the present invention to provide a method as described above, wherein the 2-keto-3-deoxyxylonate dehydratase is a protein selected from the group consisting of:

(A) a protein comprising the amino acid sequence of SEQ ID NO: 22 or 38;

(B) a protein comprising the amino acid sequence of SEQ ID NO: 22 or 38, but which includes substitution, deletion, insertion, or addition of one or several amino acid residues, and wherein said protein has 2-keto-3-deoxyxylonate dehydratase activity; and (C) a protein comprising an amino acid sequence having an identity of 90% or higher to the amino acid sequence of SEQ ID NO: 22 or 38, and wherein said protein has 2-keto-3-deoxyxylonate dehydratase activity.

It is a further aspect of the present invention to provide a method as described above, wherein the α-ketoglutaric semialdehyde dehydrogenase is a protein selected from the group consisting of:

(A) a protein comprising the amino acid sequence of SEQ ID NO: 24 or 40;

(B) a protein comprising the amino acid sequence of SEQ ID NO: 24 or 40, but which includes substitution, deletion, insertion, or addition of one or several amino acid residues, and wherein said protein has α-ketoglutaric semialdehyde dehydrogenase activity; and (C) a protein comprising an amino acid sequence having an identity of 90% or higher to the amino acid sequence of SEQ ID NO: 24 or 40, and wherein said protein has α-ketoglutaric semialdehyde dehydrogenase activity.

It is a further aspect of the present invention to provide a method as described above, wherein the target substance is selected from the group consisting of an amino acid, nucleic acid, and peptide.

It is a further aspect of the present invention to provide a method as described above, wherein the target substance is an amino acid selected from the group consisting of L-glutamic acid, L-glutamine, L-arginine, and L-lysine.

It is a further aspect of the present invention to provide a method as described above, wherein the target substance is a purine nucleoside selected from the group consisting of inosine, xanthosine, guanosine, and adenosine.

It is a further aspect of the present invention to provide a method as described above, wherein the target substance is a purine nucleotide selected from the group consisting of inosinic acid, xanthylic acid, and guanylic acid.

It is a further aspect of the present invention to provide a method as described above, wherein the bacterium is a *Corynebacterium* bacterium.

It is a further aspect of the present invention to provide a method as described above, wherein the bacterium is *Corynebacterium glutamicum*.

BRIEF DESCRIPTION OF THE DRAWINGS

FIG. 5(B) shows glucose concentration in the culture supernatant, and FIG. 5(C) shows glutamic acid concentration in the culture supernatant. "WT" represents the *C. glutamicum* ATCC13869/pVK9Peftu_xylAB strain, and "ΔNCgl2954" represents the *C. glutamicum* ATCC13869ΔNCgl2954/pVK9Peftu_xylAB strain.

FIG. 6(A) shows turbidity (OD620) of the culture broth, FIG. 6(B) shows xylose concentration in the culture supernatant, and FIG. 6(C) shows glutamic acid concentration in the culture supernatant. "WT" represents the *C. glutamicum* ATCC13869/pVK9Peftu_xylAB strain, and "ΔNCgl2954" represents the *C. glutamicum* ATCC13869ΔNCgl2954/pVK9Peftu_xylAB strain.

FIG. 8(A)-(C) shows results of glutamic acid fermentation performed in the xylose medium, specifically, FIG. 8(A) shows turbidity (OD620) of the culture broth, 8(B) shows xylose concentration in the culture supernatant, and 8(C) shows glutamic acid concentration in the culture supernatant. "WT" represents the *C. glutamicum* ATCC13869+D/pVK9Peftu_NXA strain, and "ΔNCgl2954" represents the *C. glutamicum* ATCC13869ΔNCgl2954+D/pVK9Peftu_NXA strain.

DETAILED DESCRIPTION OF EXEMPLARY EMBODIMENTS

Figure 1:
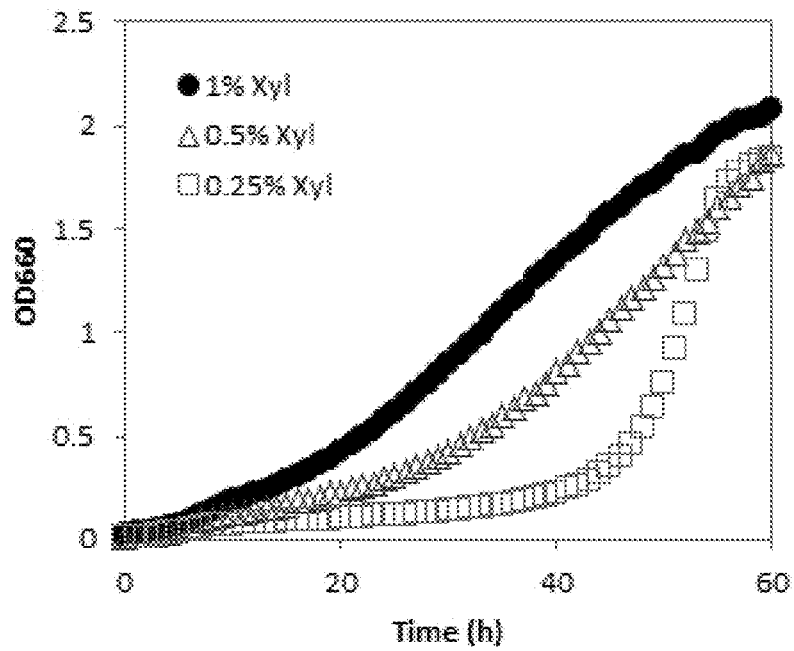
FIG. 1 shows a proliferation profile of the *C. glutamicum* ATCC 13869/pVK9Peftu_xylAB strain obtained in the xylose medium.

The method of the present invention is a method for producing a target substance which includes the steps of culturing a coryneform bacterium having an ability to produce the target substance in a medium containing xylose to produce and accumulate the target substance in the medium or cells of the bacterium, and collecting the target substance from the medium or cells, wherein a mutation of the NCgl2954 gene has been introduced into the bacterium that results in an increased ability of the bacterium to assimilate xylose. The bacterium can be referred to as "bacterium of the present invention".

<1> Bacterium of the Present Invention

The bacterium of the present invention is a coryneform bacterium having an ability to produce a target substance, and the bacterium also has an improved ability to assimilate xylose due to the introduction of a mutation into the NCgl2954 gene.

<1-1> Coryneform bacterium having an ability to produce a target substance

The phrase "bacterium having an ability to produce a target substance" or "bacterium having a target substance-producing ability" can refer to a bacterium having an ability to produce and accumulate a target substance in a medium or cells of the bacterium in such a degree that the target substance can be collected, when the bacterium is cultured in the medium. The bacterium having a target substance-producing ability may be a bacterium that is able to accumulate a target substance in a medium in an amount larger than that obtained with a non-modified strain. Examples of the non-modified strain include wild-type strains and the parent strain of the bacterium. The bacterium having a target substance-producing ability may be a bacterium that is able to accumulate a target substance in a medium in an amount of 0.5 g/L or more, or 1.0 g/L or more.

The target substance is not particularly limited, so long as it can be produced by fermentation using a coryneform bacterium. Examples of the target substance include, for example, L-amino acids, nucleic acids, and proteins. Examples of the target substance further include, for example, α-ketoglutaric acid and derivatives thereof. The bacterium of the present invention may have an ability to produce one kind of target substance, or may have an ability to produce two or more kinds of target substances.

Examples of the L-amino acid include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. The bacterium of the present invention may have an ability to produce one kind of L-amino acid, or may have an ability to produce two or more kinds of L-amino acids. The term "amino acid" may refer to L-amino acid, unless otherwise stated.

Examples of α-ketoglutaric acid and derivatives thereof include α-ketoglutaric acid, L-glutamic acid, L-glutamine, L-arginine, L-citrulline, L-ornithine, L-proline, γ-aminobutyric acid (GABA), and putrescine.

Examples of nucleic acids include purine substances. Examples of purine substances include purine nucleosides and purine nucleotides. Examples of the purine nucleosides include inosine, guanosine, xanthosine, and adenosine. Examples of the purine nucleotides include 5'-phosphate esters of the purine nucleosides. Examples of the 5'-phosphate esters of the purine nucleosides include inosinic acid (inosine-5'-monophosphate, IMP), guanylic acid (guanosine-5'-monophosphate, GMP), xanthylic acid (xanthosine-5'-monophosphate, XMP), and adenylic acid (adenosine-5'-monophosphate, AMP). The bacterium of the present invention may have an ability to produce one kind of purine substance, or may have an ability to produce two or more kinds of purine substances. For example, the bacterium of the present invention may have an ability to produce one or more kinds of purine nucleosides. For example, the bacterium of the present invention may have an ability to produce one or more kinds of purine nucleotides.

The protein is not particularly limited, so long as it can be expressed in a host coryneform bacterium. The protein may be a protein derived from the bacterium of the present invention or a heterogenous protein. The heterologous protein may be, for example, a protein derived from a microorganism, a protein derived from a plant, a protein derived from an animal, or a protein derived from a virus, or a an artificially designed protein. The proteins may be a monomeric protein or a multimeric protein. The proteins may be a naturally secretory protein or a naturally non-secretory protein. The term "protein" also includes peptides, oligopeptides, or polypeptides.

The target substance to be produced may be a free compound, salt thereof, or mixture thereof. That is, the term "target substance" may mean the target substance in the form of a free compound, salt thereof, or mixture thereof, unless otherwise stated. Examples of salt will be mentioned later.

Examples of the coryneform bacterium include bacteria belonging to the genus *Corynebacterium, Brevibacterium, Microbacterium*, or the like.

Specific examples of the coryneform bacteria include the following species.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Corynebacterium glutamicum* (*Brevibacterium divaricatum*) ATCC 14020
*Corynebacterium glutamicum* (*Brevibacterium flavum*) ATCC 13826, ATCC 14067, AJ12418 (FERM BP-2205)
*Brevibacterium immariophilum* ATCC 14068
*Corynebacterium glutamicum* (*Brevibacterium lactofermentum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria include bacteria which have previously been classified into the genus *Brevibacterium*, but are presently united into the genus *Corynebacterium* (Int. J. Syst. Bacteriol., 41, 255 (1991)). Moreover, *Corynebacterium stationis* includes such a bacterium that has previously been classified into *Corynebacterium ammoniagenes*, but is presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: 12301 Parklawn Drive, Rockville, Md. 20852, P.O. Box 1549, Manassas, Va. 20108, United States of America). That is, registration numbers are assigned to the respective strains, and the strains can be ordered by using these registration numbers (refer to atcc.org/). The registration numbers of the strains are listed in the catalogue of the American Type Culture Collection.

The bacterium of the present invention may be a bacterium inherently having a target substance-producing ability, or may be a bacterium modified so that it has a target substance-producing ability. The bacterium having a target substance-producing ability can be obtained by, for example, imparting a target substance-producing ability to such a bacterium as mentioned above, or enhancing a target substance-producing ability of such a bacterium as mentioned above.

<1-1-1> L-Amino Acid-Producing Bacteria

To impart or enhance an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. The activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parent strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP 1010755 A, and so forth. The detailed procedures for enhancing enzyme activity will be described later.

Further, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" referred to here includes an enzyme involved in decomposition of the objective amino acid. The method for reducing an enzyme activity will be described later.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability include, for example, a method of modifying a bacterium so that the bacterium has an increased activity or activities of one or more kinds of enzymes selected from the L-glutamic acid biosynthesis enzymes. Examples of such enzymes include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (OA), methylcitrate synthase (prpC), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are examples of the names of the genes encoding the enzymes (the same shall apply to the same occasions hereafter). It is preferable to enhance the activity or activities of one or more kinds of enzymes selected from, for example, glutamate dehydrogenase, citrate synthase, phosphoenol pyruvate carboxylase, and methylcitrate synthase, among these enzymes.

Examples of coryneform bacteria modified so that expression of the glutamate synthetase gene (gltBD) is increased include those disclosed in WO99/07853.

Examples of methods for imparting or enhancing L-glutamic acid-producing ability also include, for example, a method of modifying a bacterium so that the bacterium has a reduced activity or activities of one or more kinds of enzymes selected from the enzymes that catalyze a reaction branching away from the biosynthesis pathway of L-glutamic acid to generate a compound other than L-glutamic acid. Examples of such enzymes include, but are not particularly limited to, isocitrate lyase (aceA), α-ketoglutarate dehydrogenase (sucA, odhA), phosphotransacetylase (pta), acetate kinase (ack), acetohydroxy acid synthase (ilvG), acetolactate synthase (ilvI), formate acetyltransferase (pfl), lactate dehydrogenase (ldh), alcohol dehydrogenase (adh), glutamate decarboxylase (gadAB), succinate dehydrogenase (sdhABCD), and 1-pyroline-5-carboxylate dehydrogenase (putA). It is preferable to reduce or delete, for example, the α-ketoglutarate dehydrogenase activity, among these enzymes.

Coryneform bacteria in which the α-ketoglutarate dehydrogenase activity is reduced or eliminated, and methods for obtaining those are disclosed in WO2008/075483. Specific examples of coryneform bacteria in which the α-ketoglutarate dehydrogenase activity is reduced or eliminated include, for example, the following strains.

*Corynebacterium glutamicum* (*Brevibacterium lactofermentum*) L30-2 strain (Japanese Patent Laid-open (Kokai) No. 2006-340603)

*Corynebacterium glutamicum* (*Brevibacterium lactofermentum*) ΔS strain (WO95/34672)

*Corynebacterium glutamicum* (*Brevibacterium lactofermentum*) AJ12821 (FERM BP-4172, French Patent No. 9401748)

*Corynebacterium glutamicum* (*Brevibacterium flavum*) AJ12822 (FERM BP-4173, French Patent No. 9401748)

*Corynebacterium glutamicum* AJ12823 (FERM BP-4174, French Patent No. 9401748)

*Corynebacterium glutamicum* L30-2 strain (Japanese Patent Laid-open (Kokai) No. 2006-340603)

Examples of L-glutamic acid-producing bacteria and parent strains for deriving them also include strains in which both the α-ketoglutarate dehydrogenase (sucA) activity and the succinate dehydrogenase (sdh) activity are reduced or eliminated (Japanese Patent Laid-open (Kokai) No. 2010-041920). Specific examples of such strains include, for example, *Corynebacterium glutamicum* 8L3GΔSDH strain, which is the odhAsdhA double-deficient strain of *Corynebacterium glutamicum* ATCC 14067 (Japanese Patent Laid-open (Kokai) No. 2010-041920).

Examples of methods for imparting or enhancing L-glutamic acid-producing ability also include a method of modifying a bacterium so that the D-xylulose-5-phosphate phosphoketolase activity and/or the fructose-6-phosphate phosphoketolase activity are/is enhanced (Japanese Patent Laid-open (Kohyo) No. 2008-509661). Either one of the D-xylulose-5-phosphate phosphoketolase activity and the fructose-6-phosphate phosphoketolase activity may be enhanced, or both may be enhanced. In this specification, D-xylulose-5-phosphate phosphoketolase and fructose-6-phosphate phosphoketolase may be collectively referred to as phosphoketolase.

The D-xylulose-5-phosphate phosphoketolase activity means an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183: 2929-2936, 2001).

The fructose-6-phosphate phosphoketolase activity means an activity for converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001).

Examples of methods for imparting or enhancing L-glutamic acid-producing ability also include, for example, a method of enhancing the expression of the yhfK gene (WO2005/085419) or the ybjL gene (WO2008/133161), which is an L-glutamic acid secretion gene.

Furthermore, examples of methods for imparting or enhancing L-glutamic acid-producing ability to or in coryneform bacteria also include methods of imparting resistance to an organic acid analogue, respiratory inhibitor, or the like, and methods of imparting sensitivity to a cell wall synthesis inhibitor. Specific examples of such methods include, for example, the method of imparting monofluoroacetic acid resistance (Japanese Patent Laid-open (Kokai) No. 50-113209), the method of imparting adenine resistance or thymine resistance (Japanese Patent Laid-open (Kokai) No. 57-065198), the method of attenuating urease (Japanese Patent Laid-open (Kokai) No. 52-038088), the method of imparting malonic acid resistance (Japanese Patent Laid-open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-open (Kokai) No. 57-2689), the method of imparting guanidine resistance (Japanese Patent Laid-open (Kokai) No. 56-35981), the method of imparting sensitivity to penicillin (Japanese Patent Laid-open (Kokai) No. 4-88994), and so forth.

Specific examples of such resistant or sensitive bacteria include the following strains.

*Corynebacterium glutamicum* (*Brevibacterium flavum*) AJ3949 (FERM BP-2632, refer to Japanese Patent Laid-open (Kokai) No. 50-113209)

*Corynebacterium glutamicum* AJ11628 (FERM P-5736, refer to Japanese Patent Laid-open (Kokai) No. 57-065198)

*Corynebacterium glutamicum* (*Brevibacterium flavum*) AJ11355 (FERM P-5007, refer to Japanese Patent Laid-open (Kokai) No. 56-1889)

*Corynebacterium glutamicum* AJ11368 (FERM P-5020, refer to Japanese Patent Laid-open (Kokai) No. 56-1889)

*Corynebacterium glutamicum* (*Brevibacterium flavum*) AJ11217 (FERM P-4318, refer to Japanese Patent Laid-open (Kokai) No. 57-2869)

*Corynebacterium glutamicum* AJ11218 (FERM P-4319, refer to Japanese Patent Laid-open (Kokai) No. 57-2869)

*Corynebacterium glutamicum* (*Brevibacterium flavum*) AJ11564 (FERM BP-5472, refer to Japanese Patent Laid-open (Kokai) No. 56-140895)

*Corynebacterium glutamicum* (*Brevibacterium flavum*) AJ11439 (FERM BP-5136, refer to Japanese Patent Laid-open (Kokai) No. 56-35981)

*Corynebacterium glutamicum* H7684 (FERM BP-3004, refer to Japanese Patent Laid-open (Kokai) No. 04-88994)

*Corynebacterium glutamicum* (*Brevibacterium lactofermentum*) AJ11426 (FERM P-5123, refer to Japanese Patent Laid-open (Kokai) No. 56-048890)

*Corynebacterium glutamicum* AJ11440 (FERM P-5137, refer to Japanese Patent Laid-open (Kokai) No. 56-048890)

*Corynebacterium glutamicum* (*Brevibacterium lactofermentum*) AJ11796 (FERM P-6402, refer to Japanese Patent Laid-open (Kokai) No. 58-158192)

Furthermore, examples of methods for imparting or enhancing L-glutamic acid-producing ability to or in coryneform bacteria also include a method of enhancing expression of the yggB gene and a method of introducing a mutant yggB gene having a mutation in the coding region (WO2006/070944). The yggB gene is a gene encoding a mechanosensitive channel. The yggB gene of the *Corynebacterium glutamicum* ATCC 13032 strain corresponds to the sequence complementary to the sequence of the nucleotide numbers 1,336,091 to 1,337,692 in the genome sequence registered as Genbank Accession No. NC_003450 in the NCBI database, and is also called NCgl1221. The YggB protein is registered as GenBank accession No. NP_600492. The nucleotide sequence of the yggB gene of *Corynebacterium glutamicum* 2256 (ATCC 13869) and the amino acid sequence of the YggB protein encoded by the gene are shown in SEQ ID NOS: 25 and 26, respectively.

Examples of the mutant yggB gene usable in the aforementioned methods include yggB genes having the following mutation(s). The YggB protein encoded by a mutant yggB gene is also referred to as a mutant YggB protein. A yggB gene not having such mutation(s) and the YggB protein encoded by the gene are also referred to as a wild-type yggB gene and wild-type YggB protein, respectively. Examples of the wild-type YggB protein include, for example, a protein having the amino acid sequence shown in SEQ ID NO: 26.

(1) Mutation on C-Terminal Side

The mutation on the C-terminal side is a mutation introduced into a part of the nucleotide sequence of the region encoding the sequence of the amino acid numbers 419 to 533 in SEQ ID NO: 26. Although the mutation on the C-terminal side is not particularly limited so long as a mutation is introduced into at least a part of the nucleotide sequence of the aforementioned region, the mutation on the C-terminal side is preferably a mutation for inserting an insertion sequence (henceforth also referred to as "IS") or inserting transposon. The mutation on the C-terminal side may be any of a mutation for introducing amino acid substitution (missense mutation), a mutation for introducing frame shift mutation induced by insertion of the aforementioned IS or the like, and a mutation for introducing nonsense mutation.

Examples of the mutation on the C-terminus side include, for example, a mutation for inserting a nucleotide sequence at the site encoding the valine residue at the position 419 of the wild-type YggB protein (2A-1 type mutation). The 2A-1 type mutation may be, for example, a mutation that causes deletion or replacement of a part or all of the amino acid residues of the positions 419 to 533 of the wild-type YggB protein. Specific examples of a mutant yggB gene having the 2A-1 type mutation include, for example, a yggB gene having the nucleotide sequence of SEQ ID NO: 25, but which includes insertion of IS at the position next to "G" of the position 1255, and encoding a mutant YggB protein having a full length of 423 amino acid residues, which is shorter than the original wild-type YggB protein (SEQ ID NO: 26) (Japanese Patent Laid-open (Kokai) No. 2007-222163).

Examples of the mutation on C-terminus side also include, for example, a mutation for replacing a proline residue existing at any of the positions 419 to 533 of the wild-type YggB protein with an amino acid residue other than proline residue. Examples of such a proline residue include the proline residues at the positions 424, 437, 453, 457, 462, 469, 484, 489, 497, 515, 529, and 533 of the wild-type YggB protein.

(2) Mutation in Transmembrane Region

It is estimated that the YggB protein encoded by the yggB gene has five transmembrane regions. In the amino acid sequence of the wild-type YggB protein of SEQ ID NO: 26, the transmembrane regions correspond to the regions of the amino acid numbers 1 to 23 (first transmembrane region), 25 to 47 (second transmembrane region), 62 to 84 (third transmembrane region), 86 to 108 (fourth transmembrane region), and 110 to 132 (fifth transmembrane region). The yggB gene may have a mutation in a region encoding any of these transmembrane regions. The mutation in the transmembrane region is desirably a mutation including substitution, deletion, addition, insertion, or inversion of one or several amino acid residues while not accompanied by frame shift mutation or nonsense mutation. Examples of the mutation in the transmembrane region include a mutation for inserting one or several amino acid residues (for example, Cys-Ser-Leu) between the leucine residue at position 14 and the tryptophan residue at position 15, a mutation for replacing the alanine residue at position 100 with another amino acid residue (for example, an amino acid residue having hydroxyl group on the side chain (Thr, Ser, or Tyr), preferably Thr), and a mutation for replacing the alanine residue at position 111 with another amino acid residue (for example, an amino acid residue having hydroxyl group on the side chain (Thr, Ser, or Tyr), preferably Thr), in the amino acid sequence shown in SEQ ID NO: 26, and so forth. Specific examples of a mutant yggB gene having such a mutation in a transmembrane region include, for example, a yggB gene having the sequence of SEQ ID NO: 25, but which includes insertion of TTCATTGTG at the position next to "G" of the position 44 (A1 type mutation), a yggB gene having the sequence of SEQ ID NO: 25, but which includes substitution of "A" for "G" of the position 298 (19 type mutation), and a yggB gene having the sequence of SEQ ID NO: 25, but which includes substitution of "T" for "C" of the position 332 (L30 type mutation).

When the wild-type YggB protein has an amino acid sequence other than the amino acid sequence shown in SEQ ID NO: 26, the mutant yggB gene may have a mutation in a region encoding the amino acid residue corresponding to the amino acid residue at the aforementioned position in SEQ ID NO: 26. In an arbitrary wild-type YggB protein, which amino acid residue is "the amino acid residue corresponding to the amino acid residue at the aforementioned position in SEQ ID NO: 26" can be determined on the basis of an alignment between the amino acid sequence of the wild-type YggB protein and the amino acid sequence of SEQ ID NO: 26. The "amino acid number X in SEQ ID NO: 26" may be read as the "position X in SEQ ID NO: 26".

<L-Glutamine-Producing Bacteria>

Examples of the method for imparting or enhancing L-glutamine-producing ability include, for example, a method of modifying a bacterium so that the activity or activities of one or more kinds of enzymes selected from the L-glutamine biosynthesis enzymes are enhanced. Examples of such enzymes include, but not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (ginB) (EP 1229121).

Examples of the method for imparting or enhancing L-glutamine-producing ability also include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes include, but not particularly limited to, glutaminase.

Specific examples of L-glutamine-producing bacteria and parent strains for deriving them include, for example, coryneform bacteria in which the activity or activities of glutamate dehydrogenase (gdhA) and/or glutamine synthetase (glnA) (EP 1229121, EP 1424398) are enhanced, and coryneform bacteria in which the glutaminase activity (Japanese Patent Laid-open (Kokai) No. 2004-187684) is reduced.

Examples of the methods for imparting or enhancing L-glutamine-producing ability to or in coryneform bacteria also include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria having L-glutamine-producing ability include, for example, the following strains.

Corynebacterium glutamicum (Brevibacterium flavum) AJ11573 (FERM P-5492, Japanese Patent Laid-open (Kokai) No. 56-151495)

Corynebacterium glutamicum (Brevibacterium flavum) AJ11576 (FERM BP-10381, Japanese Patent Laid-open (Kokai) No. 56-151495)

Corynebacterium glutamicum (Brevibacterium flavum) AJ12212 (FERM P-8123, Japanese Patent Laid-open (Kokai) No. 61-202694)

<L-Proline-Producing Bacteria>

Examples of methods for imparting or enhancing L-proline-producing ability include, for example, a method of modifying a bacterium so that the bacterium has an increased activity or activities of one or more kinds of enzymes selected from the L-proline biosynthesis enzymes. Examples of such enzymes include glutamate-5-kinase (proB), γ-glutamylphosphate reductase, and pyroline-5-carboxylate reductase (putA). For enhancing the activity of such an enzyme, for example, the proB gene encoding a glutamate kinase desensitized to feedback inhibition by L-proline (German Patent No. 3127361) can be preferably used.

Examples of methods for imparting or enhancing L-proline-producing ability also include, for example, a method of modifying a bacterium so that the bacterium has a reduced activity of an enzyme involved in decomposition of L-proline. Examples of such an enzyme include proline dehydrogenase and ornithine aminotransferase.

<L-Threonine-Producing Bacteria>

Examples of methods for imparting or enhancing L-threonine-producing ability include, for example, a method of modifying a bacterium so that the bacterium has an increased activity or activities of one or more kinds of enzymes selected from the L-threonine biosynthesis enzymes. Examples of such enzymes include, but not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is preferable to enhance activity or activities of one or more kinds of enzymes selected from aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine.

The activities of the L-threonine biosynthesis enzymes are inhibited by the endproduct, L-threonine. Therefore, for constructing L-threonine-producing strains, it is preferred that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, expression of the threonine operon can be enhanced by removing the leader sequence or the attenuator in the attenuation region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (refer to WO98/04715). Also, the threonine operon may be constructed so that the threonine biosynthesis genes are expressed under control of the repressor and promoter of λ-phage (European Patent No. 0593792). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

It is preferred that the expression amount of the threonine operon that is modified so as to be desensitized to feedback inhibition by L-threonine as described above is increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include the rhtA gene (Res. Microbiol. 154:123-135 (2003)), rhtB gene (European Patent Laid-open No. 0994190), rhtC gene (European Patent Laid-open No. 1013765), yfiK gene, and yeaS gene (European Patent Laid-open No. 1016710). As for methods for imparting L-threonine resistance to a host, those described in European Patent Laid-open No. 0994190 and WO90/04636 can be referred to.

The thrA gene encoding aspartokinase homoserine dehydrogenase I of E. coli has been elucidated (nucleotide numbers 337 to 2799, GenBank accession NC_000913.2, gi: 49175990). The thrA gene locates between the thrL and thrB genes on the chromosome of E. coli K-12. The thrB gene encoding homoserine kinase of Escherichia coli has been elucidated (nucleotide numbers 2801 to 3733, GenBank accession NC 000913.2, gi: 49175990). The thrB gene locates between the thrA and thrC genes on the chromosome of E. coli K-12. The thrC gene encoding threonine synthase of E. coli has been elucidated (nucleotide numbers 3734 to 5020, GenBank accession NC 000913.2, gi: 49175990). The thrC gene locates between the thrB gene and the yaaX open reading frame on the chromosome of E. coli K-12. The thrA*BC operon containing a mutant thrA gene encoding aspartokinase homoserine dehydrogenase I resistant to feedback inhibition by threonine and wild-type thrBC genes can be obtained from the well-known pVIC40 plasmid, which is present in the threonine-producing E. coli strain VKPM B-3996 (U.S. Pat. No. 5,705,371).

The rhtA gene of E. coli is present at 18 min on the E. coli chromosome close to the glnHPQ operon, which encodes components of the glutamine transport system. The rhtA gene is identical to ORF1 (ybiF gene, nucleotide numbers 764 to 1651, GenBank accession number AAA218541, gi:440181), and is located between the pexB and ompX genes. The unit that expresses the protein encoded by the ORP1 is referred to as rhtA gene (rht: resistant to homoserine and threonine). It was also revealed that the rhtA23 mutation, which imparts resistance against a high concentration of threonine or homoserine, is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, Abstract No. 457, EP 1013765 A).

The asd gene of E. coli has already been elucidated (nucleotide numbers 3572511 to 3571408, GenBank accession NC 000913.1, gi:16131307), and can be obtained by PCR (refer to White, T. J. et al., Trends Genet, 5, 185 (1989)) utilizing primers prepared on the basis of the nucleotide sequence of the gene. The asd genes of other microorganisms can also be obtained in a similar manner.

The aspC gene of E. coli has also already been elucidated (nucleotide numbers 983742 to 984932, GenBank accession NC 000913.1, gi:16128895), and can be obtained by PCR utilizing primers prepared on the basis of the nucleotide sequence of the gene. The aspC genes of other microorganisms can also be obtained in a similar manner.

Further, examples of coryneform bacteria having L-threonine-producing ability include, for example, Corynebacterium acetoacidophilum AJ12318 (FERM BP-1172, refer to U.S. Pat. No. 5,188,949).

<L-Lysine-Producing Bacteria>

Examples of methods for imparting or enhancing L-lysine-producing ability include, for example, a method of modifying a bacterium so that the bacterium has an increased activity or activities of one or more kinds of enzymes selected from the L-lysine biosynthesis enzymes. Examples of such enzymes include, but not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP 1253195 A). It is preferable to enhance the activity or activities of one or more kinds of enzymes selected from, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. In addition, L-lysine-producing bacteria and parent strains for deriving them can express an increased level of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Further, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme.

Examples of methods for imparting or enhancing L-lysine-producing ability also include, for example, a method of modifying a bacterium so that the bacterium has a reduced activity or activities of one or more kinds of enzymes selected from the enzymes that catalyze a reaction branching away from the biosynthetic pathway of L-lysine to generate a compound other than L-lysine. Examples of such enzymes include, but not particularly limited to, homoserine dehydrogenase, lysine decarboxylase (U.S. Pat. No. 5,827,698), and malic enzyme (WO2005/010175).

Examples of methods for imparting or enhancing L-lysine-producing ability to or in coryneform bacteria include, for example, the method of modifying bacteria so that the activity of the lysine secretory system (lysE) is increased (WO97/23597). The lysE gene of Corynebacterium glutamicum ATCC 13032 corresponds to the complementary sequence of the sequence of the positions 1329712 to 1330413 in the genome sequence registered at the NCBI database as GenBank accession NC_006958 (VERSION NC_006958.1 GI:62388892). The LysE protein of Corynebacterium glutamicum ATCC 13032 is registered as GenBank accession YP_225551 (YP_225551.1 GI:62390149).

Examples of L-lysine-producing bacteria and parent strains for deriving them also include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues include, but not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Examples of coryneform bacteria having L-lysine-producing ability include, for example, the AEC-resistant mutant strains (Corynebacterium glutamicum (Brevibacterium lactofermentum AJ11082) (NRRL B-11470) strain etc., refer to Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (refer to U.S. Pat. Nos. 3,708,395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411, 997).

<L-Arginine-Producing Bacteria>

Examples of methods for imparting or enhancing L-arginine-producing ability include, for example, a method of modifying a bacterium so that the bacterium has an increased activity or activities of one or more kinds of enzymes selected from the L-arginine biosynthesis enzymes. Examples of such enzymes include, but not particularly limited to, N-acetylglutamate synthase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (European Patent Laid-open No. 1170361) can preferably be used.

Examples of L-arginine-producing bacteria and parent strains for deriving them include such coryneform bacteria as a strain deficient in ArgR, which is an arginine repressor (U.S. Published Patent Application No. 20020045223), and a strain in which glutamine synthetase activity is increased (U.S. Published Patent Application No. 20050014236).

Examples of L-arginine-producing bacteria and parent strains for deriving them also include mutant strains of coryneform bacteria, the mutant strains having resistance to an amino acid analogue or the like. Examples of such strains include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability include the following strains.

Corynebacterium glutamicum (Brevibacterium flavum) AJ11169 (FERM BP-6892)

Corynebacterium glutamicum (Brevibacterium lactofermentum) AJ12092 (FERM BP-6906)

Corynebacterium glutamicum (Brevibacterium flavum) AJ11336 (FERM BP-6893)

Corynebacterium glutamicum (Brevibacterium flavum) AJ11345 (FERM BP-6894)

Corynebacterium glutamicum (Brevibacterium lactofermentum) AJ12430 (FERM BP-2228)

<L-Citrulline-Producing Bacteria and L-Ornithine-Producing Bacteria>

The biosynthetic pathways of L-citrulline and L-ornithine are common to that of L-arginine. Therefore, an ability to produce L-citrulline and/or L-ornithine can be imparted or enhanced by increasing the activity or activities of N-acetylglutamate synthase (argA), N-acetylglutamyl phosphate reductase (argC), ornithine acetyltransferase (argJ), N-acetylglutamate kinase (argB), acetylornithine transaminase (argD), and/or acetylornithine deacetylase (argE) (WO2006/35831).

<L-Histidine-Producing Bacteria>

Examples of methods for imparting or enhancing L-histidine-producing ability include, for example, a method of modifying a bacterium so that the bacterium has an increased activity or activities of one or more kinds of enzymes selected from the L-histidine biosynthesis enzymes. Examples of such enzymes include, but not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2003677 and 2119536).

<L-Cysteine-Producing Bacteria>

Examples of methods for imparting or enhancing L-cysteine-producing ability include, for example, a method of modifying a bacterium so that the bacterium has an increased activity or activities of one or more kinds of enzymes selected from the L-cysteine biosynthesis enzymes. Examples of such enzymes include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and U.S. Patent Published Application No. 20050112731. Further, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Further, examples of methods for imparting or enhancing L-cysteine-producing ability also include, for example, a method of modifying a bacterium so that the bacterium has a reduced activity or activities of one or more kinds of enzymes selected form the enzymes that catalyze a reaction branching away from the biosynthesis pathway of L-cysteine to generate a compound other than L-cysteine. Examples of such enzymes include, for example, enzymes involved in decomposition of L-cysteine. Examples of the enzymes involved in decomposition of L-cysteine include, but are not particularly limited to, cysteine desulfhydrase (aecD) (Japanese Patent Laid-open (Kokai) No. 2002-233384).

Further, examples of methods for imparting or enhancing L-cysteine-producing ability also include, for example, a method of enhancing the L-cysteine excretory system, and a method of enhancing the sulfate/thiosulfate transport system. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysPTWAM gene cluster.

Further, examples of coryneform bacteria having L-cysteine-producing ability include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Serine-Producing Bacteria>

Examples of methods for imparting or enhancing L-serine-producing ability include, for example, a method of modifying a bacterium so that the bacterium has an increased activity or activities of one or more kinds of enzymes selected from L-serine biosynthesis enzymes (Japanese Patent Laid-open (Kokai) No. 11-253187). Examples of such enzymes include, but are not particularly limited to, 3-phosphoglycerate dehydrogenase (serA), phosphoserine transaminase (serf), and phosphoserine phosphatase (serB) (Japanese Patent Laid-open (Kokai) No. 11-253187). The 3-phosphoglycerate dehydrogenase activity can be enhanced by, for example, introducing a mutant serA gene encoding a mutant 3-phosphoglycerate dehydrogenase resistant to the feedback inhibition by serine into a bacterium. A mutant 3-phosphoglycerate dehydrogenase is disclosed in, for example, U.S. Pat. No. 6,180,373.

Examples of L-serine-producing bacteria and parent strains for deriving them include, for example, coryneform bacteria resistant to azaserine or β-(2-thienyl)-DL-alanine, and deficient in L-serine decomposition ability (Japanese Patent Laid-open (Kokai) No. 10-248588). Specific examples of such coryneform bacteria include, for example, Corynebacterium glutamicum (Brevibacterium flavum) AJ13324 (FERM P-16128), which is resistant to azaserine and deficient in serine decomposition ability, and Corynebacterium glutamicum (Brevibacterium flavum) AJ13325 (FERM P-16129), which is resistant to β-(2-thienyl)-DL-alanine and deficient in serine decomposition ability (Japanese Patent Laid-open (Kokai) No. 10-248588).

<L-Methionine-Producing Bacteria>

Examples of L-methionine-producing bacteria and parent strains for deriving them include L-threonine auxotrophic strains and mutant strains resistant to norleucine (Japanese Patent Laid-open (Kokai) No. 2000-139471). Examples of L-methionine-producing bacteria and parent strains for deriving them also include a strain containing a mutant homoserine transsuccinylase resistant to feedback inhibition by L-methionine (Japanese Patent Laid-open (Kokai) No. 2000-139471, U.S. Patent Published Application No. 20090029424). Since L-methionine is biosynthesized via L-cysteine as an intermediate, L-methionine-producing ability can also be improved by improving L-cysteine-producing ability (Japanese Patent Laid-open (Kokai) No. 2000-139471, U.S. Patent Published Application No. 20080311632).

<L-Leucine-Producing Bacteria>

Examples of methods for imparting or enhancing L-leucine-producing ability include, for example, a method of modifying a bacterium so that the bacterium has an increased activity or activities of one or more kinds of enzymes selected from the L-leucine biosynthesis enzymes. Examples of such enzymes include, but are not particularly limited to, the enzymes encoded by the genes of the leuABCD operon. Further, for enhancing the activity of such an enzyme, for example, the mutant leuA gene encoding an isopropyl maleate synthase desensitized to feedback inhibition by L-leucine (U.S. Pat. No. 6,403,342) can be preferably used.

Examples of coryneform bacteria having L-leucine-producing ability include, for example, Corynebacterium glutamicum (Brevibacterium lactofermentum) AJ3718 (FERM P-2516), which is resistant to 2-thiazole alanine and β-hydroxyleucine and auxotrophic for isoleucine and methionine.

<L-Isoleucine-Producing Bacteria>

Examples of the method for imparting or enhancing L-isoleucine-producing ability include, for example, a method of modifying a bacterium so that activity or activities of one or more kinds of enzymes selected from the L-isoleucine biosynthetic enzymes are increased. Examples of such enzymes include, but are not particularly limited to, threonine deaminase and acetohydroxy acid synthase (Japanese Patent Laid-open (Kokai) No. 2-458, FR 0356739, U.S. Pat. No. 5,998,178).

Examples of coryneform bacteria having L-isoleucine-producing ability include the coryneform bacterium in which brnE gene encoding a branched chain amino acid excretion protein is amplified (Japanese Patent Laid-open (Kokai) No. 2001-169788), the coryneform bacterium to which L-isoleucine-producing ability is imparted by protoplast fusion with an L-lysine-producing bacterium (Japanese Patent Laid-open (Kokai) No. 62-74293), the coryneform bacterium in which homoserine dehydrogenase is enhanced (Japanese Patent Laid-open (Kokai) No. 62-91193), the threonine hydroxamate resistant strain (Japanese Patent Laid-open (Kokai) No 62-195293), the α-ketomalonic acid resistant strain (Japanese Patent Laid-open (Kokai) No. 61-15695), the methyllysine resistant strain (Japanese Patent Laid-open (Kokai) No. 61-15696), and Corynebacterium glutamicum (Brevibacterium flavum) AJ12149 (FERM BP-759, U.S. Pat. No. 4,656,135).

<L-Valine-Producing Bacteria>

Examples of methods for imparting or enhancing L-valine-producing ability include, for example, a method of modifying a bacterium so that the bacterium has an increased activity or activities of one or more kinds of enzymes selected from the L-valine biosynthesis enzymes. Examples of such enzymes include, but are not particularly limited to, the enzymes encoded by the genes of the ilvGMEDA operon and the enzymes encoded by the ilvBNC operon. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, for enhancing the activity of such an enzyme, it is preferred that the suppression of expression by the produced L-valine is released by removing or modifying a region required for the attenuation. Further, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, for L-valine production, it is preferred that the ilvA gene is, for example, disrupted, and thereby the threonine deaminase activity is decreased.

Examples of methods for imparting or enhancing L-valine-producing ability also include, for example, a method of modifying a bacterium so that the bacterium has a reduced activity or activities of one or more kinds of enzymes selected from the enzymes that catalyze a reaction branching away from the biosynthesis pathway of L-valine to generate a compound other than L-valine. Examples of such enzymes include, but not particularly limited to, threonine dehydratase involved in the L-leucine synthesis, and the enzymes involved in the D-pantothenic acid synthesis (WO00/50624).

Examples of L-valine-producing bacteria and parent strains for deriving them also include strains resistant to an amino acid analogue or the like. Examples of such strains include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM P-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-Producing Bacteria>

Examples of L-alanine-producing bacteria and parent strains for deriving them include the coryneform bacteria deficient in the $H^+$-ATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-Producing Bacteria, L-Phenylalanine-Producing Bacteria, and L-Tyrosine-Producing Bacteria>

Examples of the method for imparting or enhancing L-tryptophan-producing ability, L-phenylalanine-producing ability, and/or L-tyrosine-producing ability include, for example, a method of modifying a bacterium so that the activity or activities of one or more kinds of enzymes selected from the L-tryptophan, L-phenylalanine, and/or L-tyrosine biosynthetic enzymes are enhanced.

Examples of enzymes common to the biosynthesis systems of these aromatic amino acids include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP 763127 B). The expressions of the genes encoding these enzymes are controlled by the tyrosine repressor (tyrR), and the activities of these enzymes may be enhanced by deleting the tyrR gene (EP 763127 B).

Examples of the L-tryptophan biosynthetic enzymes include, but not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase consists of α and β subunits encoded by the trpA and trpB genes, respectively. Since the anthranilate synthase is subject to feedback inhibition by L-tryptophan, a gene encoding this enzyme introduced with a mutation for desensitization to feedback inhibition may be used for enhancing the activity of that enzyme. Since the phosphoglycerate dehydrogenase is subject to feedback inhibition by L-serine, a gene encoding this enzyme introduced with a mutation for desensitization to feedback inhibition may be used for enhancing the activity of that enzyme. Further, by enhancing expression of the operon (ace operon) consisting of the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthetic enzymes include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, a gene encoding these enzymes introduced with a mutation for desensitization to feedback inhibition may be used for enhancing the activities of these enzymes.

Examples of the L-tyrosine biosynthetic enzymes include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, a gene encoding these enzymes introduced with a mutation for desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Further, the L-tryptophan, L-phenylalanine, and/or L-tyrosine-producing bacteria may be modified so that a by-product uptake system is enhanced. Examples of the by-product include aromatic amino acids other than the objective aromatic amino acid. Examples of the gene encoding such a by-product uptake system include tnaB and mtr, which are genes encoding the L-tryptophan uptake system, pheP, which is a gene encoding the L-phenylalanine uptake system, and tyrP, which is a gene encoding the L-tyrosine uptake system (EP 1484410).

Examples of coryneform bacteria having L-tryptophan-producing ability include *Corynebacterium glutamicum* AJ12118 (FERM BP-478) (Japanese Patent No. 01681002), which is resistant to sulfaguanidine, the strain introduced with the tryptophan operon (Japanese Patent Laid-open (Kokai) No. 63-240794), and the strain introduced with a gene encoding shikimate kinase derived from a coryneform bacterium (Japanese Patent Laid-open (Kokai) No. 01-994749).

Examples of coryneform bacteria having L-phenylalanine-producing ability include, for example, the *Corynebacterium glutamicum* strains BPS-13 (FERM BP-1777), K77 (FERM BP-2062), and K78 (FERM BP-2063) (EP 331145 A, Japanese Patent Laid-open (Kokai) No. 02-303495), of which phosphoenolpyruvate carboxylase or pyruvate kinase activity is reduced, and the tyrosine-auxotrophic strain (Japanese Patent Laid-open (Kokai) No. 05-049489).

Examples of coryneform bacteria having L-tyrosine-producing ability include, for example, *Corynebacterium glutamicum* AJ11655 (FERM P-5836, Japanese Patent Publication No. 2-6517), and *Corynebacterium glutamicum* (*Brevibacterium lactofermentum*) AJ12081 (FERM P-7249, Japanese Patent Laid-open (Kokai) No. 60-70093).

Further, examples of methods for imparting or enhancing an L-amino acid-producing ability include, for example, a method of modifying a bacterium so that the activity for secreting an L-amino acid from the bacterial cell is increased. The activity for secreting an L-amino acid can be increased by, for example, increasing the expression of a gene encoding a protein responsible for secretion of the L-amino acid. Examples of genes encoding proteins responsible for secretion of various amino acids include, for example, b2682 gene (ygaZ), b2683 gene (ygaH), b1242 gene (ychE), and b3434 gene (yhgN) (Japanese Patent Laid-open (Kokai) No. 2002-300874).

Further, examples of methods for imparting or enhancing an L-amino acid-producing ability also include, for example, a method of modifying a bacterium so that the activity or activities of one or more of proteins involved in the glycometabolism and proteins involved in the energy metabolism are increased.

Examples of the proteins involved in the glycometabolism include proteins involved in uptake of saccharides and the glycolysis system enzymes. Examples of genes encoding the proteins involved in the glycometabolism include the glucose-6-phosphate isomerase gene (pgi, WO01/02542), phosphoenolpyruvate synthase gene (pps, EP 877090 A), phosphoenolpyruvate carboxylase gene (ppc, WO95/06114), pyruvate carboxylase gene (pyc, WO99/18228, EP 1092776 A), phosphoglucomutase gene (pgm, WO03/04598), fructose bisphosphate aldolase gene (pfkB, fbp, WO03/04664), pyruvate kinase gene (pykF, WO03/008609), transaldolase gene (talB, WO03/008611), fumarase gene (fum, WO01/02545), non-PTS sucrose uptake gene (csc, EP 149911 A), and sucrose utilization gene (scrAB operon, WO90/04636).

Examples of genes encoding the proteins involved in the energy metabolism include the transhydrogenase gene (pntAB, U.S. Pat. No. 5,830,716) and cytochrome bo-type oxidase gene (cyoB, EP 1070376 A).

<1-1-2> Nucleic Acid-Producing Bacteria

A purine substance-producing ability can be imparted or enhanced by the methods conventionally employed in the breeding of purine substance-producing bacteria such as those of Bacillus bacteria and Escherichia bacteria.

A purine substance-producing ability can be imparted or enhanced by, for example, imparting auxotrophy such as adenine auxotrophy, or further imparting resistance to purine analogues and a drug such as sulfaguanidine (refer to Japanese Patent Publication (Kokoku) Nos. 38-23099, 54-17033, 55-45199, 57-14160, 57-41915 and 59-42895, Published U.S. Patent Application No. 20040166575). A mutant strain having a purine substance-producing ability, such as an auxotrophic strain and a drug-resistant strain, can be obtained by subjecting a parent strain or wild-type strain to a mutagenesis treatment and selecting a mutant strain showing a desired phenotype using an appropriate selection medium. Examples of the mutagenesis treatment include, for example, X-ray irradiation, ultraviolet irradiation, and treatment with a mutagenesis agent such as N-methyl-N'-nitro-N-nitrosoguanidine (MNNG), ethyl methanesulfonate (EMS), and methyl methanesulfonate (MMS).

A purine substance-producing ability can also be imparted or enhanced by enhancing the intracellular activity of an enzyme involved in biosynthesis of a purine substance. Activity of one kind of enzyme may be enhanced, or activities of two or more kinds of enzymes may be enhanced. Methods for enhancing an enzyme activity will be explained later. An enzyme activity can be enhanced by, for example, modifying a bacterium so that expression of a gene encoding the enzyme is enhanced. Methods for enhancing gene expression are described in WO18935, EP 1010755 A, and so forth.

Purine nucleotides are biosynthesized via phosphoribosylpyrophosphate (PRPP) as an intermediate. Purine nucleosides are biosynthesized by dephosphorylation of purine nucleotides. Examples of enzymes involved in the biosynthesis of these purine substances include, for example, PRPP synthetase (prs) and the proteins encoded by the purine operon.

Examples of the purine operon include, for example, the purEKBCSQLFMNHD operon of Bacillus subtilis (Bacillus subtilis and Its Closest Relatives, Editor in Chief: A. L. Sonenshein, ASM Press, Washington D.C., 2002) and the pur regulon of Escherichia coli (Escherichia and Salmonella, Second Edition, Editor in Chief: F. C. Neidhardt, ASM Press, Washington D.C., 1996). For example, expression of the total purine operon may be enhanced, or expression of one or more genes selected from the genes contained in the purine operon may be enhanced.

Among these, for example, activity or activities of one or more kinds of enzymes selected from PRPP synthetase (prs) and PRPP amidotransferase (purF) are preferably enhanced.

When an enzyme involved in biosynthesis of a purine substance is negatively regulated by feedback inhibition, expression inhibition, or the like, the enzymatic activity can be enhanced by, for example, reducing or eliminating such regulation, and the purine substance-producing ability can be thereby improved (WO99/003988).

Expression of the purine operon is suppressed by the purine repressor encoded by the purR gene. Therefore, expression of the purine operon can be enhanced by, for example, reducing the activity of the purine repressor (U.S. Pat. No. 6,284,495). The activity of the purine repressor can be reduced by, for example, disrupting the purR gene encoding the purine repressor (U.S. Pat. No. 6,284,495). Further, expression of the purine operon is regulated by the terminator-antiterminator sequence (it is also called attenuator sequence) locating downstream from the promoter (Ebbole, D. J. and Zalkin, H., J. Biol. Chem., 1987, 262, 8274-8287; Ebbole, D. J. and Zalkin, H., J. Biol. Chem., 1988, 263, 10894-10902; Ebbole, D. J. and Zalkin, H., J. Bacteriol., 1989, 171, 2136-2141). Therefore, expression of the purine operon can be enhanced by, for example, deleting the attenuator sequence. Deletion of the attenuator sequence can be attained by the same method as that used for disruption of a gene explained later.

The PRPP synthetase is subject to feedback inhibition by ADP. Therefore, for example, by making a bacterium harbor a mutant PRPP synthetase gene encoding a desensitized-type PRPP synthetase for which the feedback inhibition by ADP is reduced or eliminated, the PRPP synthetase activity can be enhanced, and the purine substance-producing ability can be thereby improved (WO99/003988). Examples of the desensitized-type PRPP synthetase include PRPP synthetase having a mutation that substitutes Ala (A) for Asp (D) of the position 128 of the wild-type PRPP synthetase (S. G. Bower et al., J. Biol. Chem., 264, 10287 (1989)).

The PRPP amidotransferase is subject to feedback inhibition by AMP and GMP. Therefore, for example, by making a bacterium harbor a mutant PRPP amidotransferase gene encoding a desensitized-type PRPP amidotransferase for which the feedback inhibition by AMP and/or GMP is reduced or eliminated, the PRPP amidotransferase activity can be enhanced, and the purine substance-producing ability can be thereby improved (WO99/003988). Examples of the desensitized-type PRPP amidotransferase include PRPP amidotransferase in which Gln (Q) substitutes for Lys (K) of the position 326 of the wild-type PRPP amidotransferase, and PRPP amidotransferase in which Gln (Q) substitutes for Lys (K) of the position 326, and Trp (W) substitutes for Pro (P) of the position 410 of the wild-type PRPP amidotransferase (G. Zhou et al., J. Biol. Chem., 269, 6784 (1994)).

A purine substance-producing ability can also be imparted or enhanced by reducing activity of an enzyme that catalyzes a reaction branching away from biosynthetic pathway of a purine substance to generate another compound (WO99/

003988). Activity of one kind of enzyme may be reduced, or activities of two or more kinds of enzymes may be reduced. The "enzyme that catalyzes a reaction branching away from biosynthetic pathway of a purine substance to generate another compound" referred to here also includes an enzyme involved in decomposition of a purine substance. Methods for reducing enzymatic activity will be explained later.

Examples of the enzyme that catalyzes a reaction branching away from biosynthetic pathway of a purine substance to generate another compound include, for example, purine nucleoside phosphorylase (deoD, pupG), succinyl-AMP synthase (purA), adenosine deaminase (add), inosine-guanosine kinase (gsk), GMP reductase (guaC), 6-phosphogluconate dehydrase (edd), phophoglucose isomerase (pgi), adenine deaminase (yicP), xanthosine phosphorylase (xapA), and IMP dehydrogenase (guaB). The enzyme of which activity is to be reduced may be chosen according to kind of the target purine substance, and so forth.

A purine substance-producing ability can also be imparted or enhanced by reducing the activity of fructose bisphosphatase (fructose 1,6-bisphosphatase) (fbp) (WO2007/125782).

A purine substance-producing ability can also be imparted or enhanced by reducing the activity of a protein involved in uptake of a purine substance (WO99/003988). Examples of such a protein involved in uptake of a purine substance include, for example, nucleoside permease (nupG) (WO99/003988).

A purine substance-producing ability can also be imparted or enhanced by enhancing the activity of a protein involved in excretion of a purine substance. Examples of such a protein involved in excretion of a purine substance include, for example, proteins encoded by the rhtA (ybiF) gene (Russian Patent No. 2239656), yijE gene (Russian Patent No. 2244003), ydeD gene (Russian Patent No. 2244004), yicM gene (Russian Patent No. 2271391), ydhL gene (Japanese Patent Laid-open (Kohyo) No. 2007-530011), and nepI gene (FEMS Microbiology Letters, Volume 250, Issue 1, pages 39-47, September 2005).

Further, inosinic acid-producing ability can be imparted or enhanced by imparting resistance to an L-glutamine analogue and resistance to a proline analogue to a bacterium (Japanese Patent Laid-open (Kokai) No. 2004-516833). Examples of the L-glutamine analogue include azaserine and 6-diazo-5-oxo-L-norleucine (DON). Examples of the proline analogue include 3,4-dehydroproline, L-azetidine-2-carboxylic acid, L-thiazolidine-4-carboxylic acid, (S)-2,2-dimethyl-4-oxazolide-carboxylic acid, (S)-5,5-dimethyl-4-thiazolide-carboxylic acid, (4S,2RS)-2-ethyl-4-thiazolidine-carboxylic acid, (2S,4S)-4-hydroxy-2-pyrroline-carboxylic acid, 2-piperidine-carboxylic acid, and 2,5-pyrrolidin-edione. Examples of inosinic acid-producing bacteria include, for example, *Corynebacterium ammoniagenes* CJIP009 (KCCM-10226, Japanese Patent Laid-open (Kokai) No. 2004-516833).

Further, xanthylic acid-producing ability can be imparted or enhanced by the methods used for breeding of xanthylic acid-producing bacteria of coryneform bacteria, of which typical example is *Corynebacterium ammoniagenes*. Examples of such methods include, for example, enhancing the PRPP amidotransferase activity (Japanese Patent Laid-open (Kokai) No. 8-168383), imparting resistance to an aliphatic amino acid (Japanese Patent Laid-open (Kokai) No. 4-262790), and imparting resistance to dehydroproline (South Korean Patent Laid-open No. 2003-56490).

Such methods for imparting or enhancing purine substance-producing ability as mentioned above may be used independently, or used as an arbitrary combination of them.

<1-1-3> Protein-Producing Bacteria

Secretory production of proteins can be enabled with coryneform bacteria using a signal peptide that functions in coryneform bacteria. Specifically, secretory production of a target protein can be enabled by making a coryneform bacterium harbor a gene construct comprising a promoter sequence that functions in the coryneform bacterium, a nucleic acid sequence encoding a signal peptide that functions in the coryneform bacterium and ligated downstream of the promoter sequence, and a nucleic acid sequence encoding a target protein and ligated downstream of the nucleic acid sequence encoding a signal peptide, and allowing expression of the target protein. It is sufficient that the nucleic acid sequence encoding the target protein is ligated downstream of the nucleic acid sequence encoding a signal peptide so that a heterogenous protein is expressed as a fused protein with this signal peptide. Examples of coryneform bacteria used for secretory production of proteins include, for example, strains of which the activity of cell surface protein is reduced. Examples of such strains include the *C. glutamicum* YDK010 strain (WO2004/029254), which is a cell surface protein PS2-deficient strain of the *C. glutamicum* AJ12036 strain (FERM BP-734). Further, examples of methods for imparting or enhancing ability of secretory production of protein include, for example, modifying a coryneform bacterium so that the activity of penicillin-binding protein is reduced (WO2013/065869), modifying a coryneform bacterium so that the expression of the gene encoding a metallopeptidase is increased (WO2013/065772), modifying a coryneform bacterium so that the coryneform bacterium harbors a mutant ribosomal protein S1 gene (WO2013/118544), and expressing a target protein with inserting an amino acid sequence containing Gln-Glu-Thr between a signal peptide and the target protein (WO2013/062029). Such methods for imparting or enhancing protein-producing ability as mentioned above may be used independently, or may be used in an arbitrary combination.

<1-2> Xylose Assimilability

The bacterium of the present invention is able to assimilate xylose. The bacterium of the present invention may be a bacterium inherently able to assimilate xylose, or may be a bacterium modified so that it is able to assimilate xylose. A bacterium able to assimilate xylose can be obtained by, for example, imparting the ability to assimilate xylose to such bacteria as mentioned above, or by enhancing the ability to assimilate xylose of such bacteria as mentioned above.

Xylose assimilability can be imparted or enhanced by modifying a bacterium so that activity or activities of one or more kinds of proteins constituting a xylose assimilation pathway are increased. The protein of which activity is to be increased can be appropriately chosen according to type of coryneform bacterium to be used, and so forth.

The following two kinds of pathways can be mentioned as the xylose assimilation pathway. The bacterium of the present invention may have the both pathways, or only one of the pathways.

Pathway 1: Xylose→xylulose→xylulose-5-phosphate

Pathway 2: Xylose→xylonolactone→xylonate→2-keto-3-deoxyxylonate→α-ketoglutaric semialdehyde→α-ketoglutarate The pathway 1 is constituted by xylose isomerase and xylulokinase.

"Xylose isomerase" refers to a protein having an activity of catalyzing the following reaction of isomerizing D-xylose into D-xylulose (EC 5.3.1.5). This activity is also referred to as "xylose isomerase activity".

D-Xylose→D-xylulose

"Xylulokinase" refers to a protein having an activity of catalyzing the following reaction of phosphorylating D-xylulose (EC 2.7.1.17). This activity is also referred to as "xylulokinase activity".

ATP+D-xylulose→ADP+D-xylulose-5-phosphate

Examples of a gene encoding xylose isomerase include the xylA gene. Examples of a gene encoding xylulokinase include the xylB gene. Examples of the xylA gene and xylB gene include the xylA gene and xylB gene of *Escherichia coli*. The nucleotide sequence of the xylAB operon of the *Escherichia coli* K-12 MG1655 strain is shown as SEQ ID NO: 10. In the nucleotide sequence shown as SEQ ID NO: 10, the xylA gene and xylB gene correspond to the sequence of the positions 1 to 1323 and the sequence of the positions 1395 to 2849, respectively. The amino acid sequences of the XylA protein and XylB protein of the *Escherichia coli* K-12 MG1655 strain are shown as SEQ ID NOS: 11 and 12, respectively. Examples of the xylB gene also include the xylB gene of *Corynebacterium glutamicum*. The nucleotide sequence of the xylB gene and the amino acid sequence of XylB protein of *C. glutamicum* ATCC 13869 are shown as SEQ ID NOS: 35 and 36, respectively.

The pathway 2 is constituted by xylose dehydrogenase, xylonolactonase, xylonate dehydratase, 2-keto-3-deoxyxylonate dehydratase, and α-ketoglutaric semialdehyde dehydrogenase. The second half of the pathway 2, i.e., the pathway from xylonate to α-ketoglutarate constituted by xylonate dehydratase, 2-keto-3-deoxyxylonate dehydratase, and α-ketoglutaric semialdehyde dehydrogenase is also called "Weimberg pathway" (J. Biol. Chem., 236:629-636). The whole pathway 2 or Weimberg pathway is also called "NXA (Novel Xylose Assimilation) pathway".

"Xylose dehydrogenase" refers to a protein having an activity of catalyzing the following reaction of oxidizing D-xylose into D-xylonolactone (EC 1.1.1.175 or 1.1.1.179). This activity is also referred to as "xylose dehydrogenase activity".

D-Xylose+NAD(P)$^+$→D-xylonolactone+NAD(P)H+H$^+$

"Xylonolactonase" refers to a protein having an activity of catalyzing the following ring cleavage reaction of D-xylonolactone (EC 3.1.1.68). This activity is also referred to as "xylonolactonase activity".

D-Xylono-1,4-lactone+H$_2$O→D-xylonate

"Xylonate dehydratase" refers to a protein having an activity of catalyzing the following reaction of dehydrating D-xylonate (EC 4.2.1.82). This activity is also referred to as "xylonate dehydratase activity".

D-Xylonate→2-dehydro-3-deoxy-D-xylonate+H$_2$O

"2-Keto-3-deoxyxylonate dehydratase" refers to a protein having an activity of catalyzing the following reaction of dehydrating 2-keto-3-deoxyxylonate (EC 4.2.1.-). This activity is also referred to as "2-keto-3-deoxyxylonate dehydratase activity".

2-Dehydro-3-deoxy-D-xylonate→
i. α-ketoglutaric semialdehyde+H$_2$O

"α-Ketoglutaric semialdehyde dehydrogenase" refers to a protein having an activity of catalyzing the following reaction of oxidizing α-ketoglutaric semialdehyde (EC 1.2.1.26). This activity is also referred to as "α-ketoglutaric semialdehyde dehydrogenase activity".

α-Ketoglutaric semialdehyde+NADP$^+$+H$_2$O→
ii. 2-ketoglutarate+NADPH+2H$^+$

Examples of genes encoding the enzymes constituting the pathway 2 include the genes of the xylXABCD operon. The xylB gene encodes xylose dehydrogenase. The xylC gene encodes xylonolactonase. The xylD gene encodes xylonate dehydratase. The xylX gene encodes 2-keto-3-deoxyxylonate dehydratase. The xylA gene encodes α-ketoglutaric semialdehyde dehydrogenase.

Although the same gene names are used, the xylA gene and xylB gene encoding xylose isomerase and xylulokinase of the pathway 1 are genes different from the xylA gene and xylB gene encoding α-ketoglutaric semialdehyde dehydrogenase and xylose dehydrogenase of the pathway 2, respectively.

Examples of the xylXABCD operon include the xylXABCD operon of the *Caulobacter crescentus*. Examples of *Caulobacter crescentus* include the CB15 strain, NA1000 strain, and K31 strain. The genome sequences of the *Caulobacter crescentus* CB15 strain, NA1000 strain, and K31 strain are registered at the NCBI database as GenBank Accession Nos. AE005673, CP001340, and CP000927, respectively. The xylXABCD genes of the *Caulobacter crescentus* CB15 strain are registered with the gene symbols of CC_0822, CC_0821, CC_0820, CC_0819, and CC_0823, respectively. The xylXABCD genes of the *Caulobacter crescentus* NA1000 strain are registered with the gene symbols of CCNA_00865, CCNA_00864, CCNA_00863, CCNA_00862, and CCNA_00866, respectively. The xylABCD genes (xylX is not identified yet) of the *Caulobacter crescentus* K31 strain are registered with the gene symbols of Caul_4001, Caul_4002, Caul_4003, and Caul_4000, respectively. The nucleotide sequences of the xylXABCD genes of the *Caulobacter crescentus* CB15 strain are shown as SEQ ID NOS: 37, 39, 41, 43, and 45, respectively. The amino acid sequences of the XylXABCD proteins of the *Caulobacter crescentus* CB15 strain are shown as SEQ ID NOS: 38, 40, 42, 44, and 46, respectively.

Examples of xylose dehydrogenase gene also include the xylB gene of *Sphingomonas* or *Pseudomonas* bacteria such as *Sphingomonas elodea* (formerly *Pseudomonas elodea*). The nucleotide sequence of the xylB gene and the amino acid sequence of XylB protein of *Sphingomonas elodea* are shown as SEQ ID NOS: 15 and 16, respectively.

Examples of xylonolactonase gene also include the xylC gene of *Sphingomonas* or *Pseudomonas* bacteria such as *Sphingomonas elodea* (*Pseudomonas elodea*). The nucleotide sequence of the xylC gene and the amino acid sequence of XylC protein of *Sphingomonas elodea* are shown as SEQ ID NOS: 17 and 18, respectively.

Examples of xylonate dehydratase gene also include the yjhG gene and yagF gene of *Escherichia* bacteria such as *Escherichia coli*, as well as xylD gene homologues of *Agrobacterium* bacteria such as *Agrobacterium tumefaciens*, *Herbaspirillum* bacteria such as *Herbaspirillum seropedicae*, *Actinoplanes* bacteria such as *Actinoplanes missouriensis*, and *Aspergillus* microorganisms such as *Aspergillus oryzae*. The nucleotide sequence of the yagF gene and the amino acid sequence of YagF protein of the *Escherichia coli* K-12 MG1655 strain are shown as SEQ ID NOS: 19 and 20, respectively.

Examples of the 2-keto-3-deoxyxylonate dehydratase gene include the xylX gene homologues of *Agrobacterium* bacteria such as *Agrobacterium tumefaciens*, *Sphingomonas* or *Pseudomonas* bacteria such as *Sphingomonas elodea* (*Pseudomonas elodea*), *Zobellia* bacteria such as *Zobellia galactanivorans*, *Thermobacillus* bacteria such as *Thermobacillus composti*, and *Arthrobacter* bacteria such as *Arthrobacter globiformis*. The nucleotide sequence of the xylX gene and the amino acid sequence of XylX protein of *Sphingomonas elodea* are shown as SEQ ID NOS: 21 and 22, respectively.

Examples of the α-ketoglutaric semialdehyde dehydrogenase gene include the xylA gene homologues of *Azospirillum* bacteria such as *Azospirillum brasilense*, and *Halomonas* bacteria such as *Halomonas boliviensis*, as well as the ycbD gene of *Bacillus* bacteria such as *Bacillus subtilis*. The nucleotide sequence of the ycbD gene and the amino acid sequence of YcbD protein of *Bacillus subtilis* are shown as SEQ ID NOS: 23 and 24, respectively.

The activity of each of the proteins constituting the xylose assimilation pathways can be measured according to the descriptions of published references (Non-patent document 3 and Patent document 8).

Further, some of glucose dehydrogenases (EC 1.1.1.47, EC 1.1.1.118, EC 1.1.1.119, EC 1.1.5.2 etc.) catalyze the reaction of oxidizing D-xylose into D-xylonolactone. Therefore, in order to impart or enhance xylose assimilability, the activity of such glucose dehydrogenase may be enhanced in addition to, or instead of the activity of xylose dehydrogenase mentioned above. Examples of such glucose dehydrogenase include the glucose dehydrogenase of *Pseudomonas putida* S12 (Jean-Paul Meijnen et al., Appl. Environ. Microbiol., 2009 May, 75(9):2784-2791). The glucose dehydrogenase of *Pseudomonas putida* S12 catalyzes the reaction of oxidizing D-xylose into D-xylonolactone by using pyrroloquinoline quinone as an electron acceptor.

The genes used for the aforementioned modifications of bacteria, such as the impartation or enhancement of a target substance-producing ability, and impartation or enhancement of xylose assimilability, are not limited to the genes exemplified above or genes having a known nucleotide sequence, but may be a variant thereof, so long as a protein that maintains the original function is encoded. For example, the genes used for the modifications of bacteria may be a gene encoding a protein having an amino acid sequence of known protein, but which includes substitution, deletion, insertion, or addition of one or several amino acid residues at one or several positions. To such variants of genes or proteins, the descriptions concerning variants of the NCgl2954 gene and the proteins encoded thereby mentioned later can be applied, mutatis mutandis.

<1-3> Improvement of Xylose Assimilability by Introduction of Mutation into NCgl2954 Gene In the bacterium of the present invention, xylose assimilability has been improved by introduction of a mutation into the NCgl2954 gene. The bacterium of the present invention can be obtained by introducing a mutation into the NCgl2954 gene of a coryneform bacterium having a target substance-producing ability to improve xylose assimilability of the bacterium. The bacterium of the present invention can also be obtained by introducing a mutation into the NCgl2954 gene of a coryneform bacterium to improve xylose assimilability of the bacterium, and then imparting a target substance-producing ability to the bacterium. The bacterium of the present invention may be a bacterium that acquired a target substance-producing ability as a result of improvement of xylose assimilability provided by introduction of a mutation into the NCgl2954 gene. In the present invention, modifications for constructing the bacterium of the present invention can be performed in an arbitrary order.

Specifically, the xylose assimilability may be improved by improvement of xylose uptake ability. That is, the bacterium of the present invention may be a bacterium in which xylose uptake ability has been improved by introduction of a mutation into the NCgl2954 gene.

Improvement of xylose assimilability (for example, improvement of xylose uptake ability) can be confirmed by, for example, confirming improvement of growth or improvement of xylose consumption in culture of a coryneform bacterium performed in a medium containing xylose as a sole carbon source.

<1-3-1> NCgl2954 Gene and NCgl2954 Protein

The NCgl2954 gene is a gene encoding a transcription factor. The protein encoded by the NCgl2954 gene can also be referred to as NCgl2954 protein. The NCgl2954 gene of *Corynebacterium glutamicum* ATCC 13032 corresponds to the sequence of the positions 3261130 to 3261993 in the genome sequence registered at the NCBI database as GenBank accession NC 003450 (VERSION NC 003450.3 GI: 58036263). The NCgl2954 gene of *Corynebacterium glutamicum* ATCC 13032 is synonymous with Cgl3059. The NCgl2954 protein of *Corynebacterium glutamicum* ATCC 13032 is registered as GenBank accession NP_602251 (version NP_602251.2 GI:23309012). Further, the nucleotide sequence of the NCgl2954 gene and the amino acid sequence of the NCgl2954 protein of *Corynebacterium glutamicum* ATCC 13869 are shown as SEQ ID NOS: 13 and 14, respectively.

The NCgl2954 gene may be a variant of the genes exemplified above, so long as the variant maintains the original function. Similarly, the NCgl2954 protein may be a variant of the proteins exemplified above, so long as the variant maintains the original function. Such a variant that maintains the original function may be referred to as "conservative variant". In the present invention, the term "NCgl2954 gene" includes not only the NCgl2954 genes exemplified above, but also conservative variants thereof. Similarly, the term "NCgl2954 protein" includes not only the NCgl2954 proteins exemplified above, but also conservative variants thereof. Examples of the conservative variants include, for example, homologues and artificially modified genes and proteins of the NCgl2954 genes and NCgl2954 proteins exemplified above.

The expression "variant maintains the original function" means that the variant has a function (such as activity and property) corresponding to the function (such as activity and property) of the original gene or protein. That is, the expression "variant maintains the original function" means that, in the case of the NCgl2954 gene, a variant of the gene has a property that deletion thereof in a coryneform bacterium improves xylose assimilability of the bacterium. Further, the expression "variant maintains the original function" may also mean that, in the case of the NCgl2954 gene, a variant of the gene encodes a protein that maintains the original function. Similarly, the expression "variant maintains the original function" means that, in the case of the NCgl2954 protein, a variant of the protein has a property that deletion thereof in a coryneform bacterium improves xylose assimilability of the bacterium. Specifically, the xylose assimilability may be improved by improvement of xylose uptake ability. That is, "to improve xylose assimilability" may mean to improve xylose uptake ability.

Whether a variant of the gene or protein has the property that deletion thereof in a coryneform bacterium improves xylose assimilability of the bacterium can be confirmed by deleting the gene or a gene encoding the protein in a coryneform bacterium having xylose assimilability, and confirming whether the xylose assimilability is improved or not.

Homologues of the aforementioned NCgl2954 genes can be easily obtained from public databases by, for example, BLAST search or FASTA search using a nucleotide sequence of the NCgl2954 gene mentioned above as a query sequence. Further, homologues of the aforementioned NCgl2954 genes can also be obtained by, for example, PCR using a chromosome of a coryneform bacterium as the template, and oligonucleotides prepared on the basis of a known gene sequence as the primers.

The NCgl2954 gene may encode a protein having any of the aforementioned amino acid sequences, but which includes substitution, deletion, insertion, or addition of one or several amino acid residues at one or several positions, so long as the protein maintains the original function. Although the number of "one or several" mentioned above may differ depending on the positions of amino acid residues in the three-dimensional structure of the protein or types of amino acid residues, specifically, it is, for example, 1 to 50, 1 to 40, or 1 to 30, 1 to 20, 1 to 10, 1 to 5, or 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

The NCgl2954 gene may be a gene encoding a protein showing a homology of, for example, 80% or more, 90% or more, 95% or more, 97% or more, 99% or more, to the total amino acid sequence of any of the amino acid sequences mentioned above, so long as the protein maintains the original function. In this description, "homology" means "identity".

The NCgl2954 gene may also be a DNA that is able to hybridize under stringent conditions with a probe that can be prepared from a known gene sequence, such as a sequence complementary to a partial or entire sequence of any of the aforementioned nucleotide sequences. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned nucleotide sequences as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Further, since the degeneracy of codons differs depending on the host, arbitrary codons in the NCgl2954 gene may be replaced with equivalent codons, so long as the original function is maintained.

The aforementioned descriptions concerning conservative variants of the genes and proteins can be applied mutatis mutandis to variants of arbitrary proteins such as L-amino acid biosynthesis system enzymes and genes encoding them.

<1-3-2> Mutation to be Introduced into NCgl2954 Gene

The expression "a mutation is introduced into the NCgl2954 gene" specifically means that a mutation is introduced into a coding region and/or an expression control region of the NCgl2954 gene on a chromosome. The "expression control region" is a generic term for referring to a site that affects gene expression. Examples of expression control region include promoter, Shine-Dalgarno (SD) sequence (also referred to as ribosome binding site (RBS)), and spacer region between RBS and start codon. Expression control regions can be determined by, for example, using a promoter search vector, or gene analysis software such as GENETYX.

The mutation to be introduced into the NCgl2954 gene is not particularly limited, so long as introduction of the mutation improves xylose assimilability of a coryneform bacterium. Examples of the mutation that improves xylose assimilability of a coryneform bacterium include a mutation that attenuates expression of the NCgl2954 gene and a mutation that disrupts the NCgl2954 gene. That is, the bacterium of the present invention may be, for example, a bacterium of which xylose assimilability has been improved by attenuation of the NCgl2954 gene expression or disruption of the gene.

The phrase "expression of a gene is attenuated" can also mean "expression of a gene is reduced". The phrase "expression of a gene is reduced" can mean that the expression amount of the gene per cell is reduced compared with that observed in a non-modified strain such as wild-type strains and parent strain of the bacterium. The phrase "expression of a gene is reduced" can include when the gene is not expressed at all. Expression of a gene may be reduced to, for example, 50% or less, 20% or less, 10% or less, 5% or less, or 0% of that observed in a non-modifying strain.

A reduction in the expression of a gene may be provided by, for example, a reduction in the transcription efficiency, a reduction in the translation efficiency, or a combination of them. A reduction in the expression of a gene can be attained by, for example, modifying an expression control region of the gene such as promoter, SD sequence (RBS), and spacer region between RBS and the start codon of the gene. When an expression control region is modified, preferably one or more nucleotides, more preferably two or more nucleotides, particularly preferably three or more nucleotides, of the expression control region are modified. Further, a part or the whole of the expression control region may be deleted. A reduction in the expression of a gene can also be attained by, for example, introducing a mutation that reduces the expression of the gene into the coding region of the gene. For example, the expression of a gene can be reduced by replacing a codon in a coding region of a gene with a synonymous codon less frequently used in a host. Further, for example, gene expression itself may be reduced by disruption of a gene as described later.

The expression that "a gene is disrupted" can mean that the gene is modified so that it does not produce a protein that normally functions. The phrase "a protein that normally functions is not produced" can include when the protein is not produced at all from the gene, and when the protein of which function (such as activity and property) per molecule is reduced or eliminated is produced from the gene.

Disruption of a gene can be attained by, for example, deleting a part or the whole of the coding region of the gene on a chromosome. Furthermore, the whole of a gene including sequences upstream and downstream from the gene on a chromosome may be deleted. The sequences upstream and downstream from the gene may contain, for example, an expression control region of the gene. The region to be deleted may be any region such as an N-terminus region, an internal region, or a C-terminus region. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene. Usually, insertion of a longer region can usually more surely inactivate the gene. It is preferred that reading frames of the sequences upstream and downstream from the insertion site are not the same. The other sequence is not particularly limited so long as insertion of the sequence provides disruption of a gene, and examples thereof include, for example, a marker gene such as antibiotic resistance genes, and a gene useful for production of a target substance.

Such modification of a gene on a chromosome as described above can be attained by, for example, preparing a deficient type gene in which a partial sequence of the gene is deleted so that it cannot produce a protein that can normally function, and transforming a host with a recombinant DNA including the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easy. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ, phage (Cho, E. H., Gumport, R. I., Gardner, J. F., J. Bacteriol., 184:5200-5203 (2002)) (refer to WO2005/010175), a method of using a plasmid including a temperature sensitive replication origin, a method of using a plasmid capable of conjugative transfer, a method of utilizing a suicide vector not including a replication origin that functions in a host (U.S. Pat. No. 6,303,383, Japanese Patent Laid-open (Kokai) No. 05-007491), and so forth.

A mutation may also be introduced by, for example, a mutagenesis treatment. Examples of the mutagenesis treatment include usual mutation treatments such as X-ray irradiation, ultraviolet irradiation, and treatment with a mutation agent such as N-methyl-N'-nitro-N-nitrosoguanidine (MNNG), ethyl methanesulfonate (EMS), and methyl methanesulfonate (MMS).

A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA include Northern hybridization, RT-PCR, and so forth (Molecular Cloning, Cold spring Harbor Laboratory Press, Cold Spring Harbor (USA), 2001). The amount of mRNA is preferably decreased to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably decreased to, for example, 50% or less, 20% or less, 10% or less, 5% or less, or 0%, of that observed in a non-modified strain.

Disruption of a gene can be confirmed by determining nucleotide sequence of a part or the whole of the gene, restriction enzyme map, full length, or the like of the gene depending on the means used for the disruption.

Further, specific examples of the mutation to be introduced into the NCgl2954 gene include, for example, the mutations of (1) to (7) mentioned below. By the introduction of any of the mutations of (1) to (7) mentioned below, for example, expression of the NCgl2954 gene may be attenuated, or the NCgl2954 gene may be disrupted. The NCgl2954 gene not having any of the mutations of (1) to (7) mentioned below may also be referred to as "wild-type NCgl2954 gene", and the NCgl2954 gene having any of the mutations of (1) to (7) mentioned below may also be referred to as "mutant NCgl2954 gene". Further, a protein encoded by a wild-type NCgl2954 gene may also be referred to as "wild-type NCgl2954 protein", and a protein encoded by a mutant NCgl2954 gene may also be referred to as "mutant NCgl2954 protein". Examples of the wild-type NCgl2954 gene include the NCgl2954 genes exemplified above, and conservative variants thereof.

(1) Replacing the leucine residue at position 438 of a wild-type NCgl2954 protein with another amino acid residue (2) Replacing the tryptophan residue at position 274 of a wild-type NCgl2954 protein with another amino acid residue (3) Replacing the tyrosine residue at position 377 of a wild-type NCgl2954 protein with another amino acid residue (4) Replacing the leucine residue at position 365 of a wild-type NCgl2954 protein with another amino acid residue (5) Replacing the leucine residue at position 366 of a wild-type NCgl2954 protein with another amino acid residue (6) Replacing the alanine residue at position 367 of a wild-type NCgl2954 protein with another amino acid residue (7) Truncating the N-terminus of the wild-type NCgl2954 protein at position 368.

The "another amino acid residue" (i.e. amino acid residue existing after the substitution) is not particularly limited, so long as it is an amino acid residue other than the amino acid residue existing before the substitution. Specific examples of the "another amino acid residue" include lysine, ornithine, arginine, histidine, isoleucine, alanine, valine, leucine, glycine, threonine, serine, proline, phenylalanine, tyrosine, tryptophan, cysteine, methionine, glutamic acid, aspartic acid, glutamine, and asparagine residues, provided that they must be other than the amino acid residues existing before the substitution. The leucine residue at position 438 may be replaced with, for example, a proline residue. The tryptophan residue at position 274 may be replaced with, for example, an arginine residue. The leucine residue at the position 365 may be replaced with, for example, a serine residue. The leucine residue at the position 366 may be replaced with, for example, an arginine residue. The alanine residue at the position 367 may be replaced with, for example, a phenylalanine residue. The tyrosine residue at the position 377 may be replaced with, for example, an asparagine residue.

A mutant NCgl2954 gene may have one or more mutations selected from these mutations. For example, a mutant NCgl2954 gene may have the mutations of (4) to (7) mentioned above in combination. Specifically, for example, a mutant NCgl2954 gene produced from the wild-type NCgl2954 gene shown as SEQ ID NO: 13 by deletion of GC at the positions 1092 and 1093 encodes a mutant NCgl2954 protein corresponding to the wild-type NCgl2954 protein shown as SEQ ID NO: 14 in which the leucine-leucine-alanine residues at the positions 365 to 367 are replaced with serine-arginine-phenylalanine residues, and the protein is truncated at position 368.

An "amino acid residue at the position X of a wild-type NCgl2954 protein" referred to in the present invention means an amino acid residue corresponding to the amino acid residue at the position X of SEQ ID NO: 14, unless otherwise stated. That is, the mutations of (1) to (7) mentioned above may be described, in other words, as follows.

(1) Replacing an amino acid residue corresponding to the leucine residue at position 438 of SEQ ID NO: 14 with an amino acid residue other than a leucine residue;

(2) Replacing an amino acid residue corresponding to the tryptophan residue at position 274 of SEQ ID NO: 14 with an amino acid residue other than a tryptophan residue (3) Replacing an amino acid residue corresponding to the tyrosine residue at position 377 of SEQ ID NO: 14 with an amino acid residue other than tyrosine residue (4) Replacing an amino acid residue corresponding to the leucine residue at position 365 of SEQ ID NO: 14 with an amino acid residue other than a leucine residue (5) Replacing an amino acid residue corresponding to the leucine residue at position 366 of SEQ ID NO: 14 with an amino acid residue other than a leucine residue (6) Replacing an amino acid residue corresponding to the alanine residue at position 367 of SEQ ID NO: 14 with an amino acid residue other than an alanine residue (7) Truncating the protein the position 368 of SEQ ID NO: 14 and the rest of the N-terminus of the protein.

The "position X" in an amino acid sequence is the X-th position counted from the N-terminus of the amino acid sequence, and the amino acid residue of the N-terminus is the amino acid residue at the position 1. That is, the position of amino acid residue is a relative position, and the absolute position thereof may shift due to deletion, insertion, addition, or the like of an amino acid residue or residues. For example, "the leucine residue at position 438 of a wild-type NCgl2954 protein" means an amino acid residue corresponding to the leucine residue at position 438 of SEQ ID NO: 14. When one amino acid residue is deleted on the N-terminus side with respect to the position 438, the 437th amino acid residue from the N-terminus shall be the "leucine residue at position 438 of a wild-type NCgl2954 protein". Also, when one amino acid residue is inserted on the N-terminus side with respect to the position 438, the 439th amino acid residue counted from the N-terminus shall be the "leucine residue at position 438 of a wild-type NCgl2954 protein".

Which amino acid residue is the "amino acid residue corresponding to the amino acid residue at the position X of SEQ ID NO: 14" in an arbitrary amino acid sequence can be determined by aligning the arbitrary amino acid sequence and the amino acid sequence of SEQ ID NO: 14. The alignment can be performed by, for example, using known gene analysis software. Specific examples of such software include DNASIS produced by Hitachi Solutions, GENETYX produced by Genetyx, and so forth (Elizabeth C. Tyler et al., Computers and Biomedical Research, 24 (1) 72-96, 1991; Barton G. J. et al., Journal of Molecular Biology, 198 (2), 327-37, 1987).

When a wild-type NCgl2954 protein has an amino acid sequence other than the amino acid sequence shown as SEQ ID NO: 14, the amino acid residues for which the mutations of (1) to (7) mentioned above are introduced may be, or may not be conserved in such an amino acid sequence. That is, for example, in a wild-type NCgl2954 protein, the "amino acid residue corresponding to the leucine residue at position 438 of SEQ ID NO: 14" need not be leucine residue. Therefore, for example, the "Replacing an amino acid residue corresponding to the leucine residue at position 438 of SEQ ID NO: 14 with a proline residue" is not limited to a mutation for replacing, in the case that the amino acid residue at that position of the wild-type NCgl2954 protein is leucine residue, the leucine residue with a proline residue, but may also include replacing, in the case that the amino acid residue at that position is not leucine residue, the amino acid residue (not being leucine residue) with a proline residue.

A mutant NCgl2954 gene can be obtained by modifying a wild-type NCgl2954 gene so that the modified gene should have any of the mutations mentioned above. The modification of DNA can be performed by a known method. Specifically, the modification of DNA can be performed by, for example, the site-specific mutagenesis method for introducing an objective mutation into a target site of DNA. Examples of the site-specific mutagenesis method include, for example, a method of using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Further, a mutant NCgl2954 gene can also be obtained by chemical synthesis.

<1-4> Method for Reducing Activity of Protein

Hereafter, the methods for reducing the activity of a protein will be explained.

The expression "the activity of a protein is reduced" means that the activity of the protein per cell is reduced as compared with that of a non-modified strain such as a wild-type strain and parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. Further, the modification for reducing the activity of a protein can also be attained by, for example, disrupting the gene encoding the protein. Further, the modification for reducing the activity of a protein can also be performed by, for example, a mutagenesis treatment. Methods for reducing the expression of a gene, methods for disrupting a gene, and mutagenesis treatment are as described above.

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Further, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein. A reduction in the activity of a protein can also be confirmed by confirming a reduction in the expression of a gene encoding the protein, or by confirming disruption of such a gene.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<1-5> Methods for Increasing Activity of Protein

Hereafter, the methods for increasing the activity of a protein will be explained.

The expression "the activity of a protein is increased" means that the activity of the protein per cell is increased as compared with that of a non-modified strain such as a wild-type strain and parent strain. The state that "the activity of a protein is increased" may also be expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Further, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Further, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased 1.5 times or more, 2 times or more, or 3 times or more, as compared with that of a non-modified strain. Further, when the non-modified strain does not have the activity of the objective protein, it is sufficient that the protein is produced as a result of introduction of the gene encoding the protein, and for example, the protein may be produced to such an extent that the enzymatic activity can be measured.

The modification for increasing the activity of a protein is attained by, for example, increasing the expression of a gene encoding the protein. The state that "the expression of a gene is increased" may also be referred to as "the expression of a gene is enhanced". The expression of a gene may be increased 1.5 times or more, 2 times or more, or 3 times or more, as compared with that of a non-modified strain. Further, the state that "the expression of a gene is increased" includes not only when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the target substance production as a target. Homologous recombination can be performed by, for example, a method of using a linear DNA such as Red-driven integration (Datsenko, K. A., and Wanner, B. L., Proc. Natl. Acad. Sci. USA, 97:6640-6645 (2000)), a method of using a plasmid including a temperature sensitive replication origin, a method of using a plasmid capable of conjugative transfer, a method of using a suicide vector not including a replication origin that functions in a host, or a transduction method using a phage. Further, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Further, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Further, the vector preferably has a marker such as an antibiotic resistance gene for selection of transformant. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799.

When a gene is introduced, it is sufficient that the gene is expressibly harbored by the bacterium of the present invention. Specifically, it is sufficient that the gene is introduced so that it is expressed under control by a promoter sequence that functions in the bacterium of the present invention. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in the bacterium of the present invention. The terminator may be a terminator derived from the host, or a heterogenous terminator. The terminator may be the native terminator of the gene to be introduced, or a terminator of another gene. Specific examples of the terminator include, for example, trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Further, when two or more genes are introduced, it is sufficient that the genes each are expressibly harbored by the bacterium of the present invention. For example, all the genes may be carried by a single expression vector or a chromosome. Further, the genes may be separately carried by two or more expression vectors, or separately carried by a single or two or more expression vectors and a chromosome. An operon constituted by two or more genes may also be introduced. The case of "introducing two or more genes" include, for example, cases of introducing respective genes encoding two or more kinds of enzymes, introducing respective genes encoding two or more subunits constituting a single enzyme complex, and a combination of the foregoing cases.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)).

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of genes that encode the subunits may be enhanced. It is usually preferable to enhance the expression of all of the genes encoding the subunits. Further, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Further, the expression of a gene can be increased by improving the transcription efficiency of the gene. The transcription efficiency of a gene can be improved by, for example, replacing the promoter of the gene on a chromosome with a stronger promoter. The "stronger promoter" means a promoter providing an improved transcription of a gene compared with an inherently existing wild-type promoter of the gene. Examples of stronger promoters usable in coryneform bacteria include the artificially modified P54-6 promoter (Appl. Microbiol. Biotechnolo., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Further, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Further, the expression of a gene can be increased by improving the translation efficiency of the gene. The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Further, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

These expression control sequences can be modified by, for example, a method of using a temperature sensitive vector, or the Red driven integration method (WO2005/010175).

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess amount of rare codons, a translational problem may arise. According to the recent researches, it is suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a synonymous codon more frequently used. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of a protein can also be attained by, for example, enhancing the specific activity of the enzyme. Enhancement of the specific activity also includes desensitization to feedback inhibition. That is, when a protein is subject to feedback inhibition by a metabolite, the activity of the protein can be increased by making the bacterium harbor a gene encoding a mutant protein that has been desensitized to the feedback inhibition. In the present invention, "desensitization to feedback inhibition" includes attenuation and elimination of the feedback inhibition. A protein showing an enhanced specific activity can be obtained by, for example, searching various organisms. Further, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Further, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-

1933). Further, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins.

<2> Method for Producing Target Substance

<2-1> Method for Producing Target Substance

The method of the present invention is a method for producing a target substance that includes culturing the bacterium of the present invention in a medium containing xylose to produce and accumulate the target substance in the medium or cells of the bacterium, and collecting the target substance from the medium or cells. In the present invention, one kind of target substance may be produced, or two or more kinds of target substances may be produced.

The medium to be used is not particularly limited, so long as it contains xylose, the bacterium of the present invention can proliferate in it, and a target substance can be produced. As the medium, for example, a usual medium used for culture of bacteria and so forth can be used. The medium may contain, in addition to xylose, carbon source, nitrogen source, phosphate source, and sulfur source, as well as components selected from other various organic components and inorganic components as required. Types and concentrations of the medium components may be appropriately determined according to various conditions such as type of the bacterium to be used and type of the target substance to be produced.

As xylose, pure xylose such as purified xylose may be used, or a mixture containing xylose and other components may be used. Examples of such a mixture include hydrolysates of plant biomass. Such plant biomass is not particularly limited so long as it contains xylose as a constituent sugar. Examples of plant biomass include wood biomass and herb biomass. Specific examples of plant biomass include, for example, rice straw, chaff, and sugarcane bagasse. By subjecting the plant biomass to such a treatment as hydrothermal decomposition treatment, concentrated acid hydrolysis, diluted acid hydrolysis, hydrolysis with an enzyme such as cellulase, and alkaline treatment, a processed product containing xylose can be obtained. Such a processed product can be used as the carbon source, as it is, or after it is subjected to purification etc., appropriately.

As the method for treating plant biomass, hydrothermal decomposition treatment is preferred. Plant biomass may be subjected to a treatment such as hydrothermal decomposition treatment, as it is, or after it is subjected to pretreatment such as steaming and blasting, appropriately. For example, plant biomass may be ground into a size of 5 mm or smaller, and then subjected to a treatment such as hydrothermal decomposition treatment. The hydrothermal decomposition can be performed by using, for example, pressurized hot water of preferably 175 to 240° C., more preferably 200 to 230° C. Since hemicellulose components, cellulose, and lignin components dissolve at temperatures around 140° C. or higher, around 230° C. or higher, and around 140° C. or higher, respectively, a temperature within the aforementioned ranges is preferred for sufficiently dissolving the hemicellulose components.

The aforementioned hydrothermal decomposition treatment can be performed by countercurrently contacting plant biomass with pressurized hot water. Such a treatment can be performed by using the apparatuses disclosed in Japanese Patent Nos. 4436429, 4524351, and 4427583. By the hydrothermal decomposition treatment of plant biomass, the lignin components and hemicellulose components are transferred into hot water from the plant biomass, and cellulose components remain as solid content.

The reaction pressure of the hydrothermal decomposition treatment is preferably higher than the saturation vapor pressure of water at the selected temperature by 0.1 to 0.5 MPa, so that water in the inside of the apparatus becomes pressurized hot water. Reaction time is usually 20 minutes or shorter, preferably 3 to 15 minutes.

Then, the hot water is separated from the solid content, and hemicellulose contained in the hot water is subjected to a saccharification treatment. The saccharification of hemicellulose can be performed by enzymatic decomposition using a saccharification enzyme, or by sulfuric acid decomposition using sulfuric acid. In the present invention, enzymatic decomposition is preferred.

The saccharification enzyme is not particularly limited so long as a saccharification enzyme that can decompose hemicellulose to generate xylose is chosen. Specific examples of the saccharification enzyme include hemicellulase. Hemicellulase is a generic term for referring to enzymes that catalyze hydrolysis of glycosidic bonds contained in hemicellulose. Hemicellulose means polysaccharides constituting cell walls of land plant cells except for cellulose and pectin, and the main component of hemicellulose is xylan. Xylan is a heteropolysaccharide consisting of a backbone comprising xylose as a constituent sugar, and side chains comprising arabinose etc. and binding to the backbone. The main components of hemicellulase are endo-1,4-β-xylanase (EC 3.2.1.8), β-1,4-xylosidase (EC 3.2.1.37), and so forth, but hemicellulase also contains other glycosidic bond hydrolysis enzymes. Examples of commercially available hemicellulase include Cellic Htec (Novozymes), and so forth. Spezyme CP (Genencor, derived from *Trichoderma reesei*), which is a cellulase, Novozyme 188 (Novozyme, derived from *Aspergillus niger*), which is a β-glucosidase, and so forth may also be used as hemicellulase. If these enzymes are made to act on hemicellulose, xylose, arabinose, and so forth are generated. Further, not only hemicellulose, but also cellulose may be transferred into or contaminate the hot water, and therefore glucose may be generated by the saccharification treatment. In the present invention, such by-products as glucose obtained by the saccharification treatment may also be used as a carbon source, in addition to xylose.

The enzymatic reaction can be performed in an appropriate aqueous solvent such as water and buffers. The solvent used for the enzymatic reaction may be water used for the hydrothermal treatment itself. The reaction conditions, such as reaction temperature and pH, may be as described in descriptions attached to commercially available enzymes, or appropriately determined by performing preliminary experiments etc. For example, when Spezyme CP or Novozyme 188 mentioned above is used, examples of the reaction conditions are conditions of 45 to 60° C. and pH 4.5 to 6.5. Amount of the enzyme may usually be 20 to 120 FPU (filter paper unit) based on the substrate solid amount, and the reaction time may usually be, for example, 24 to 144 hours. The enzymatic reaction may be statically performed, or it may be performed with stirring. Further, in advance of the enzymatic reaction, a pretreatment such as delignification and partial decomposition of hemicellulose may be performed.

When the saccharification is performed by sulfuric acid decomposition, sulfuric acid concentration may be usually 0.1 to 5% by weight, preferably 1 to 4% by weight. The decomposition temperature may be usually 100 to 140° C., preferably around 120° C. The decomposition time may be usually 30 minutes to 3 hours, preferably around 1 hour. After the decomposition, sulfuric acid can be removed by an ion exchange resin treatment, or the like.

The sugar solution containing xylose obtained by the saccharification treatment may be used as the carbon source, as it is, or after it is subjected to such a treatment as concentration, dilution, drying, fractionation, and purification, appropriately. For example, a component such as xylose may be purified from the sugar solution to a desired extent, and then used as the carbon source.

The sugar solution obtained by the saccharification treatment may contain substances that inhibit growth and metabolism of microorganisms. Such inhibitory substances are mainly nonvolatile non-saccharide substances having a molecular weight of 3000 or smaller. Therefore, it is preferred that the sugar solution be subjected to a treatment for removing such inhibitory substances, and then used as the carbon source. Examples of the treatment for removing such inhibitory substances include adsorbent treatment, gel filtration, membrane treatment, and so forth. The sugar solution may be subjected to a treatment for removing inhibitory substances, as it is, or after it is subjected to concentration or dilution, appropriately.

Examples of adsorbent that can be used for the adsorbent treatment include, for example, activated carbon, ion exchange resins, synthetic adsorptive resins, zeolite, and silica gel. The adsorbent is preferably an adsorbent that selectively adsorbs such inhibitory substances as mentioned above. Although the adsorbent treatment can be performed as a batch treatment or by using a column, it is preferable to use a column. In the case of the batch treatment, the adsorbent is put into a vessel containing the sugar solution, and then the adsorbent and the sugar solution are separated. When a column is used, the sugar solution is flown through a column filled with the adsorbent, a washing solution is flown through the column if needed, and flow-through solution (non-adsorbed fraction) is collected. The adsorbent treatment may be performed only once, or may be repeated twice or more. Also, one kind of adsorbent may be used, or two or more kinds of adsorbents may be used in combination for the adsorbent treatment.

The sugar solution from which inhibitory substances are removed can be used as the carbon source, as it is, or after it is subjected to concentration, dilution, drying, fractionation, purification, etc., appropriately.

Various components generated by the saccharification treatment may be further subjected to isomerization, decomposition, or the like by a chemical reaction or enzymatic reaction depending on type of use.

The solid content remained after the hot water was separated from a biomass raw material subjected to the hydrothermal treatment may also be used. That is, if cellulose in such solid content is enzymatically treated with cellulase or the like, a sugar solution containing hexoses such as glucose can be obtained. In addition to xylose, such a sugar solution or a processed product thereof may be used as the carbon source.

In the method of the present invention, xylose may be or may not be used as a sole carbon source. That is, in the method of the present invention, in addition to xylose, another carbon source may be used together. The other carbon source is not particularly limited, so long as the bacterium of the present invention can utilize, and a target substance can be produced. Specific examples of the other carbon source include, for example, saccharides such as glucose, fructose, sucrose, lactose, galactose, arabinose, blackstrap molasses, hydrolysate of starch, and hydrolysate of biomass, organic acids such as acetic acid, fumaric acid, citric acid, succinic acid, and malic acid, alcohols such as glycerol, crude glycerol, and ethanol, and aliphatic acids. When another carbon source is used, ratio of xylose in the total carbon source may be, for example, 5% by weight or more, 10% by weight or more, or 20% by weight or more, preferably 30% by weight or more, more preferably 50% by weight or more. As the other carbon source, one kind of carbon source may be used, or two or more kinds of carbon sources may be used in combination.

The concentration of the carbon source in the medium is not particularly limited, so long the bacterium of the present invention can proliferate in the medium, and a target substance can be produced. The concentration of the carbon source in the medium is preferably made as high as possible in such a range that the production of the target substance is not inhibited. The initial concentration of the carbon source in the medium may be, for example, usually 1 to 30% (W/V), preferably 3 to 10% (W/V). Along with consumption of the carbon source accompanying advance of the fermentation, the carbon source may be supplementarily added.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid or the like for growth thereof is used, it is preferable to supplement a required nutrient to the medium. For example, in many of L-lysine-producing bacteria, the L-lysine biosynthetic pathway is enhanced and the L-lysine degrading ability is attenuated. Therefore, when such an L-lysine-producing bacterium is cultured, for example, one or more kinds of amino acids selected from L-threonine, L-homoserine, L-isoleucine, and L-methionine are preferably added to the medium.

Further, when L-glutamic acid is produced by using a coryneform bacterium, it is preferable to, for example, restrict the amount of biotin in the medium, or add a surfactant or penicillin to the medium. It is also preferable to add an appropriate amount of a commercially available antifoam to the medium in order to suppress foaming at the time of the culture.

Culture conditions are not particularly limited, so long as the bacterium of the present invention can proliferate, and a target substance can be produced. The culture can be performed with, for example, usual conditions used for culture of coryneform bacteria. The culture conditions may be appropriately determined depending on various conditions such as type of bacterium to be used and type of target substance to be produced.

The culture can be performed by using a liquid medium. At the time of the culture, the bacterium of the present invention cultured on a solid medium such as agar medium may be directly inoculated into a liquid medium, or the bacterium of the present invention cultured in a liquid medium as seed culture may be inoculated into a liquid medium for main culture. That is, the culture may be performed as separate seed culture and main culture. In such a case, the culture conditions of the seed culture and the main culture may be or may not be the same. Amount of the bacterium of the present invention contained in the medium at the time of the start of the culture is not particularly limited. For example, a seed culture broth showing an OD660 of 4 to 8 may be added to a medium for main culture at a ratio of 0.1 to 30 mass %, or 1 to 10 mass %, at the time of the start of the culture.

The culture can be performed as batch culture, fed-batch culture, continuous culture, or a combination of these. The medium used at the time of the start of the culture is also referred to as "starting medium". The medium supplied to a culture system (fermentation tank) in fed-batch culture or continuous culture is also referred to as "feed medium". Further, to supply a feed medium to a culture system in fed-batch culture or continuous culture is also referred to as to "feed". Further, when the culture is performed as separate seed culture and main culture, for example, both the seed culture and the main culture may be performed as batch culture. Alternatively, for example, the seed culture may be performed as batch culture, and the main culture may be performed as fed-batch culture or continuous culture.

In the present invention, the medium components each may be contained in the starting medium, feed medium, or the both. The types of the components contained in the starting medium may be or may not be the same as the types of the components contained in the feed medium. The concentration of each component contained in the starting medium may be or may not be the same as the concentration of the component contained in the feed medium. Further, two or more kinds of feed media containing different types and/or different concentrations of components may be used. For example, when medium is intermittently fed a plurality of times, the types and/or concentrations of components contained in the feed media may be or may not be the same.

The concentration of xylose in the medium is not particularly limited, so long as the bacterium of the present invention can use xylose as the carbon source. Xylose may be contained in the medium at a concentration of, for example, 10 w/v % or lower, 5 w/v % or lower, or 2 w/v % or lower. Also, xylose may be contained in the medium at a concentration of, for example, 0.2 w/v % or higher, 0.5 w/v % or higher, or 1.0 w/v % or higher. Xylose may be contained in the starting medium, feed medium, or the both at a concentration within the range exemplified above.

When xylose is contained in the feed medium, xylose may be contained in the feed medium at such a concentration that, for example, the xylose concentration in the medium after feeding is 5 w/v % or lower, 2 w/v % or lower, or 1 w/v % or lower. When xylose is contained in the feed medium, xylose may be contained in the feed medium at such a concentration that, for example, the xylose concentration in the medium after feeding is 0.01 w/v % or higher, 0.02 w/v % or higher, or 0.05 w/v % or higher.

When xylose is used as a sole carbon source, xylose may be contained at a concentration within the range exemplified above. When another carbon source is used together, xylose may also be contained at a concentration within the range exemplified above. When another carbon source is used together, xylose may also be contained at a concentration within a range defined by appropriately modifying the range exemplified above on the basis of, for example, ratio of xylose in the total carbon source, or the like.

Xylose may be or may not be contained within a certain range over the whole period of culture. For example, xylose may run short during a partial period of culture. The term "run short" means that the amount of xylose is smaller than the required amount, and it may means, for example, that the concentration in the medium becomes zero. The term "partial period of culture" may refer to, for example, 1% or less, 5% or less, 10% or less, 20% or less, 30% or less, or 50% or less of the whole period of the culture. When the culture is performed as separate seed culture and main culture, the term "whole period of the culture" may mean the whole period of the main culture. It is preferred that, during a period when xylose runs short, another carbon source exists in a sufficient amount. Even if xylose runs short during a partial period of culture as described above, culture performed under such a condition is included in the scope of the expression "culture of a bacterium in a medium containing xylose", so long as there is a culture period where the culture is performed in a medium containing xylose.

Concentration of various components such as xylose can be measured by gas chromatography (Hashimoto, K. et al., Biosci. Biotechnol. Biochem., 1996, 70:22-30) or HPLC (Lin, J. T. et al., J. Chromatogr. A., 1998, 808:43-49).

The culture can be, for example, aerobically performed. For example, the culture can be performed as aeration culture or shaking culture. The oxygen concentration can be controlled to be, for example, 5 to 50%, or about 10%, of the saturated oxygen concentration. pH of the medium may be, for example, 3 to 10, preferably 4.0 to 9.5. During the culture, pH of the medium can be adjusted as required. pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., preferably 25 to 37° C. The culture period may be, for example, 10 to 120 hours. The culture may be continued, for example, until the carbon source contained in the medium is consumed, or until the bacterium of the present invention loses the activity. By culturing the bacterium of the present invention under such conditions as described above, a target substance is accumulated in cells of the bacterium and/or the medium.

In the fed-batch culture or continuous culture, feeding of the feed medium may be continued over the whole period of the culture or only during a partial period of the culture. In the fed-batch culture or continuous culture, feeding may be intermittently performed a plurality of times.

When feeding is intermittently performed a plurality of times, the feeding may be repeatedly started and stopped so that the period for one time of feeding is, for example, 30% or shorter, 20% or shorter, or 10% or shorter, of the total period of the feeding of the plurality of times.

Further, when feeding is intermittently performed a plurality of times, the carbon source concentration in the fermentation medium can also be automatically maintained at a low level by controlling the feeding so that the second and following feedings are started when the carbon source in the fermentation medium is depleted in the non-feeding periods immediately before the respective feedings (U.S. Pat. No. 5,912,113). Depletion of the carbon source can be detected on the basis of, for example, elevation of pH, or elevation of dissolved oxygen concentration.

In the continuous culture, extraction of the culture medium may be continued over the whole period of the culture or only during a partial period of the culture. Further, in the continuous culture, extraction of the culture medium may be intermittently performed a plurality of times. Extraction and feeding of the culture medium may be or may not be simultaneously performed. For example, after extracting the culture medium, feeding may be performed, or after performing feeding, the culture medium may be extracted. It is preferred that the volume of the culture medium to be extracted is equal to the volume of the medium to be fed. The expression "the volume of the culture medium to be extracted is equal to the volume of the medium to be fed equal volume" mentioned above may mean that the volume of the culture medium to be extracted is, for example, 93 to 107% of the volume of the medium to be fed.

When the culture medium is continuously extracted, the extraction is preferably started at the same time as or after the start of the feeding. For example, within 5 hours, preferably 3 hours, more preferably 1 hour, after the start of the feeding, the extraction can be started.

When the culture medium is intermittently extracted, it is preferred that, when the target substance concentration reaches a predetermined level, a part of the culture medium is extracted to collect the target substance, and then a fresh medium is fed to continue the culture.

Further, after the target substance is collected from the extracted culture medium, the cells can be reused by recycling filtration residue containing the cells into the fermentation tank (French Patent No. 2669935).

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated include, for example, pH 5.0 to 3.0, preferably pH 4.9 to 3.5, more preferably pH 4.9 to 4.0, particularly preferably around pH 4.7 (EP 1078989 A). The culture may be performed at a pH value within the aforementioned ranges over the whole period of culture, or only during a partial period of culture. The term "partial period of culture" may refer to, for example, 50% or more, 70% or more, 80% or more, 90% or more, 95% or more, or 99% or more, of the whole period of culture.

When a basic amino acid such as L-lysine is produced, there may be employed a method in which the basic amino acid is produced by fermentation using bicarbonate ions and/or carbonate ions as major counter ions for the basic amino acid (Japanese Patent Laid-open (Kokai) No. 2002-65287, U.S. Patent Published Application No. 20020025564, EP 1813677 A). By such a method, a basic amino acid can be produced while reducing the amount(s) of sulfate ions and/or chloride ions to be used, which have been conventionally used as counter ions for a basic amino acid.

Production of the target substance can be confirmed by known methods used for detection or identification of compounds. Examples of such methods include, for example, HPLC, LC/MS, GC/MS, and NMR. These methods can be used in an appropriate combination.

The produced target substance can be collected by known methods used for separation and purification of compounds. Examples of such methods include, for example, ion-exchange resin method, membrane treatment, precipitation, and crystallization. These methods can be used in an appropriate combination. When the target substance is accumulated in bacterial cells, the bacterial cells can be disrupted with, for example, ultrasonic waves or the like, and then the target substance can be collected by the ion exchange resin method or the like from the supernatant obtained by removing the cells from the cell-disrupted suspension by centrifugation. The target substance to be collected may be a free compound, a salt thereof, or a mixture thereof. Examples of the salt include, for example, sulfate, hydrochloride, carbonate, ammonium salt, sodium salt, and potassium salt. For example, L-lysine may be free L-lysine, L-lysine sulfate, L-lysine hydrochloride, L-lysine carbonate, or a mixture of these. Also, for example, L-glutamic acid may be free L-glutamic acid, sodium L-glutamate (monosodium L-glutamate, MSG), ammonium L-glutamate (monoammonium L-glutamate), or a mixture of these. For example, in the case of L-glutamic acid, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). Also, for example, specific examples of salt of inosinic acid include sodium inosinate (5'-IMP disodium salt). Also, for example, specific examples of salt of guanylic acid include sodium guanylate (5'-GMP disodium salt).

When the target substance is precipitated in the medium, it can be collected by centrifugation, filtration, or the like. The target substance precipitated in the medium may also be isolated together with the target substance dissolving in the medium, after the target substance dissolving in the medium is crystallized.

The collected target substance may contain such components as bacterial cells, medium components, moisture, and by-product metabolites of the bacterium in addition to the target substance. Purity of the collected target substance may be, for example, 30% (w/w) or higher, 50% (w/w) or higher, 70% (w/w) or higher, 80% (w/w) or higher, 90% (w/w) or higher, or 95% (w/w) or higher.

When the L-amino acid is L-glutamic acid, for example, the monosodium L-glutamate crystal can be used as an umami seasoning. The monosodium L-glutamate crystal can be used as a seasoning in combination with a nucleic acid such as 5'-GMP disodium salt and 5'-IMP disodium salt, which also have umami taste.

<2-2> Method for Producing Purine Nucleotide

When a purine nucleoside is produced by the bacterium of the present invention, a purine nucleotide can be produced by using the purine nucleoside. The present invention thus provides a method for producing a purine nucleotide comprising culturing the bacterium of the present invention having a purine nucleoside-producing ability in a medium to produce and accumulate the purine nucleoside in the medium, phosphorylating the purine nucleoside to generate a purine nucleotide, and collecting the purine nucleotide.

In this method, a purine nucleotide corresponding to the purine nucleoside to be used is produced. That is, for example, inosinic acid can be produced from inosine, guanylic acid can be produced from guanosine, xanthylic acid can be produced from xanthosine, and adenylic acid can be produced from adenosine. In the present invention, one kind of purine nucleotide may be produced, or two or more kinds of purine nucleotides may be produced.

The purine nucleoside may be phosphorylated in a state that it is contained in the medium, or phosphorylated after it is collected from the medium. The purine nucleoside may also be phosphorylated after being subjected to a pretreatment, appropriately. Examples of the pretreatment include, for example, purification, dilution, concentration, crystallization, drying, grinding, dissolution, and so forth. These pretreatments may be performed in an appropriate combination. For example, a culture broth containing a purine nucleoside may be used as it is for the phosphorylation, or a purine nucleoside purified to a desired extent from such a culture broth may be used for the phosphorylation.

The method for phosphorylating the purine nucleoside is not particularly limited. The phosphorylation can be performed by, for example, known methods.

The phosphorylation can be performed, for example, chemically. Such chemical phosphorylation can be performed by using a phosphorylating agent such as phosphoryl chloride (POC13) (Yoshikawa et al., Studies of phosphorylation, III, Selective phosphorylation of unprotected nucleosides, Bull. Chem. Soc. Jpn., 1969, 42:3505-3508).

The phosphorylation can also be performed by using, for example, a microorganism or enzyme. That is, by allowing a microorganism having a nucleoside-5'-phosphate-producing ability to act on a purine nucleoside and a phosphate donor, a purine nucleotide can be produced (Japanese Patent Laid-open (Kolai) No. 07-231793). Further, by allowing a phosphorylation enzyme to act on a purine nucleoside and a phosphate donor, a purine nucleotide can be produced.

Specific examples of microorganisms having a nucleoside-5'-phosphate-producing ability include, for example, such strains as mentioned below (Japanese Patent Laid-open (Kokai) No. 07-231793).

Escherichia blattae JCM 1650
Serratia ficaria ATCC 33105
Klebsiella planticola IFO 14939 (ATCC 33531)
Klebsiella pneumoniae IFO 3318 (ATCC 8724)
Klebsiella terrigena IFO 14941 (ATCC 33257)
Morganella morganii IFO 3168
Enterobacter aerogenes IFO 12010
Enterobacter aerogenes IFO 13534 (ATCC 13048)
Chromobacterium fluviatile IAM 13652
Chromobacterium violaceum IFO 12614
Cedecea lapagei JCM 1684
Cedecea davisiae JCM 1685
Cedecea neteri JCM 5909

Examples of the phosphorylation enzyme include, for example, phosphatase, nucleoside kinase, and nucleoside phosphotransferase. The phosphorylation enzyme may be or may not be a purified enzyme. For example, a fraction containing a phosphorylation enzyme, such as culture of a microorganism that produces the phosphorylation enzyme, culture supernatant separated from the culture, cells separated from the culture, processed product of the cells of the microorganism, and partially purified products of these, may be used as the phosphorylation enzyme.

Examples of the nucleoside kinase include, for example, inosine-guanosine kinase. Specific examples of a method using inosine-guanosine kinase include, for example, the method for producing a purine nucleotide using an *Escherichia* bacterium introduced with a gene encoding inosine-guanosine kinase of *Escherichia coli* (WO91/08286), and the method for producing a purine nucleotide using *Corynebacterium ammoniagenes* introduced with a gene encoding inosine-guanosine kinase of *Exiguobacterium acetylicum* (WO96/30501).

Examples of the phosphatase include, for example, acid phosphatase. Examples of acid phosphatase include, for example, the acid phosphatase disclosed in Japanese Patent Laid-open (Kokai) No. 2002-000289. Preferred examples of acid phosphatase include, for example, the mutant acid phosphatase showing increased affinity for nucleosides (Japanese Patent Laid-open (Kokai) No. 10-201481), the mutant acid phosphatase showing reduced nucleotidase activity (WO96/37603), and the mutant acid phosphatase showing reduced phosphoric acid ester hydrolysis activity (Japanese Patent Laid-open (Kokai) No. 2001-245676).

Examples of the phosphate donor include, for example, polyphosphoric acid, phenyl phosphate, acetyl phosphate, carbamyl phosphate, ATP, and dATP (deoxy-ATP). Examples of polyphosphoric acid include, for example, pyrophosphoric acid, tripolyphosphoric acid, trimetaphosphoric acid, tetrametaphosphoric acid, and hexametaphosphoric acid. The phosphate donors each may be a free compound, a salt thereof, or a mixture of them. Examples of the salt include, for example, sodium salt and potassium salt. The phosphate donor can be appropriately chosen depending on type of the microorganism to be used and type of the phosphorylation enzyme to be used, etc. Further, when ATP or dATP is used as the phosphate donor, a recycling system therefor can also be used in combination (WO91/08286, WO96/30501).

Production of a purine nucleotide can be confirmed by known methods used for detection or identification of compounds. Examples of such methods include, for example, HPLC, LC/MS, GC/MS, and NMR. These methods can be used in an appropriate combination.

The produced purine nucleotide can be collected by known methods used for separation and purification of compounds. Examples of such methods include, for example, ion-exchange resin method, membrane treatment, precipitation, and crystallization. These methods can be used in an appropriate combination. The collected purine nucleotide may be a free compound, a salt thereof, or a mixture of them. The collected purine nucleotide may contain such components as phosphorylation enzyme, phosphate donor, bacterial cells, medium components, moisture, and by-product metabolites of the bacterium, in addition to the purine nucleotide. The purine nucleotide may be purified in a desired degree. Purity of the purine nucleotide may be, for example, 30% (w/w) or higher, 50% (w/w) or higher, 70% (w/w) or higher, 80% (w/w) or higher, 90% (w/w) or higher, or 95% (w/w) or higher.

EXAMPLES

Hereafter, the present invention will be more specifically explained with reference to the following non-limiting examples.

(1) Media

Compositions and preparation methods of the media used in this example are shown below.

LB Medium

The LB medium contained 10 g/L of polypeptone, 5 g/L of yeast extract, and 5 g/L of NaCl. The medium was adjusted to pH 7.0 with NaOH. The LB agar medium further contained 15 g/L of agar.

CM-Dex Medium

The CM-Dex medium contained 10 g/L of polypeptone, 10 g/L of yeast extract, 5 g/L of glucose, 1 g/L of $KH_2PO_4$, 3 g/L of urea, 0.4 g/L of $MgSO_4.7H_2O$, 0.01 g/L of $FeSO_4.7H_2O$, 0.01 g/L of $MnSO_4.5H_2O$, and 1.2 g/L (T-N) of bean filtrate (soybean hydrolysate). The medium was adjusted to pH 7.5 with KOH. The CM-Dex agar medium further contained 15 g/L of agar.

S10 Agar Medium

The S10 medium contained 100 g/L of sucrose, 10 g/L of polypeptone, 10 g/L of yeast extract, 1 g/L of $KH_2PO_4$, 3 g/L of urea, 0.4 g/L of $MgSO_4.7H_2O$, 0.01 g/L of $FeSO_4.7H_2O$, 0.01 g/L of $MnSO_4.5H_2O$, 1.2 g/L (T-N) of bean filtrate, and 10 µg/L of biotin. The medium was adjusted to pH 7.5 with KOH. The S10 agar medium further contained 15 g/L of agar.

Xylose Minimal Medium

The xylose minimal medium contained 2.5 g/L, 5.0 g/L, or 10 g/L of xylose, 2.5 g/L of $(NH_4)_2SO_4$, 0.5 g/L of $KH_2PO_4$, 0.25 g/L of $MgSO_4.7H_2O$, 2 g/L of urea, 10 mg/L of $MnSO_4.4H_2O$, 50 µg/L of biotin, 100 µg/L of vitamin B1-HCl, 15 mg/L of protocatechuic acid, 0.02 mg/L of $CuSO_4$, 10 mg/L of $CaCl_2$), and 40 g/L of MOPS. The medium was adjusted to pH 7.0 with KOH.

Seed Medium

The seed medium contained 60 g/L of glucose, 1.45 g/L of K3PO4, 1.45 g/L of KOH, 0.9 g/L of $MgSO_4.7H_2O$, 0.01 g/L of $FeSO_4.7H_2O$, 2 g/L of sodium succinate.$6H_2O$, 8.55 mg/L of para-aminobenzoic acid, 8.55 mg/L of ascorbic acid, 200 µg/L of vitamin B1-HCl, 60 µg/L of biotin, 1.54 g/L (T-N) of bean filtrate, 0.28 g/L of DL-methionine, 5 mL/L of Fermol, and 25 mg/L of kanamycin. The medium was adjusted to pH 7.2 with ammonia gas.

Glucose Main Medium

The glucose main medium contained 90 g/L of glucose, 3.46 g/L of $KH_2PO_4$, 1 g/L of $MgSO_4.7H_2O$, 0.01 g/L of $FeSO_4.7H_2O$, 0.01 g/L of $MnSO_4.5H_2O$, 23 mg/L of vitamin B1-HCl, 0.35 g/L (T-N) of bean filtrate, 15 mL/L of Fermol, and 25 mg/L of kanamycin. The medium was adjusted to pH 7.2 with ammonia gas.

Xylose Main Medium

The xylose main medium was the same as the glucose main medium, except 90 g/L of glucose was replaced with 100 g/L of xylose.

Glucose/Xylose Main Medium

The glucose/xylose main medium was the same as the glucose main medium, except 90 g/L of glucose was replaced with 45 g/L of glucose and 45 g/L of xylose.

(2) Construction of *C. glutamicum* that is Able to Assimilate Xylose

By transforming the *C. glutamicum* ATCC 13869 strain with a plasmid pVK9Peftu_xylAB carrying the xylAB genes encoding the xylose isomerase and xylulokinase of *E. coli*, a xylose assimilability-imparted strain, *C. glutamicum* ATCC13869/pVK9Peftu_xylAB strain, was constructed. The procedures are shown below.

(2-1) Construction of pVK9Peftu_xylAB

An expression plasmid pVK9Peftu_xylAB for the xylAB genes of *E. coli* was constructed as follows. pVK9Peftu_xylAB contains a sequence consisting of a promoter sequence of the elongation factor Tu (EF-Tu) gene tuf of *C. glutamicum* (WO2008/114721, henceforth referred to as "Peftu"), and the xylAB genes of *E. coli* ligated downstream of the promoter sequence.

By PCR using the chromosomal DNA of the *E. coli* MG1655 strain as the template, as well as the primers xylA_SP(2)_4691-80-12 (SEQ ID NO: 1) and xylA-B_ASP_4691-80-13 (SEQ ID NO: 2), a DNA fragment containing the xylAB genes (xylAB fragment) was obtained. Further, by PCR using the chromosomal DNA of the *C. glutamicum* ATCC 13869 strain as the template, as well as the primers EFTU_SP_4691-80-1 (SEQ ID NO: 3) and EFTU_ASP_4691-80-2 (SEQ ID NO: 4), a DNA fragment containing Peftu (Peftu fragment) was obtained. PrimeSTAR HS DNA Polymerase (Takara Bio) was used for PCR, and the reactions were performed according to the protocol attached to the enzyme.

The xylAB fragment and Peftu fragment obtained as described above were mixed with pVK9 (Japanese Patent Laid-open (Kokai) No. 2007-97573, Published U.S. Patent Application No. 20050196846) treated with XbaI, and used for in-fusion reaction with Clontech In-Fusion HD Cloning Kit (Takara Bio) according to the protocol attached to the kit, and *E. coli* JM109 was transformed with the reaction mixture. The transformants were subjected to selection by culturing them overnight at 37° C. on the LB agar medium (containing 40 mg/L of kanamycin). The objective plasmid pVK9Peftu_xylAB was obtained from an obtained transformant. The nucleotide sequences of the cloned EF-Tu promoter (Peftu) and xylAB genes are shown as SEQ ID NOS: 9 and 10, respectively.

(2-2) Transformation of *C. glutamicum*

By the electric pulse method (Japanese Patent Laid-open (Kokai) No. 2-207791), the *C. glutamicum* ATCC 13869 strain was transformed with pVK9Peftu_xylAB. The transformants were subjected to selection by culturing them overnight at 31.5° C. on the CM-Dex agar medium (containing 25 mg/L of kanamycin) to obtain a xylose assimilability-imparted strain, C. glutamicum ATCC13869/pVK9Peftu_xylAB strain.

(3) Growth of C. glutamicum that is Able to Assimilate Xylose in Xylose Minimal Medium The C. glutamicum ATCC13869/pVK9Peftu_xylAB strain as described above, was cultured in the minimal medium containing xylose as a sole carbon source (xylose minimal medium).

The cells of the C. glutamicum ATCC13869/pVK9Peftu_xylAB strain were spread on the CM-Dex agar medium (containing 25 mg/L kanamycin), and cultured overnight at 31.5° C. After the culture, the cells in about 1-cm square on the agar medium were scraped together, suspended in 1 mL of the 0.25% (w/v) xylose minimal medium, and inoculated in 5 mL of each of the 0.25% (w/v), 0.5% (w/v), and 1.0% (w/v) xylose minimal media (all containing 25 mg/L of kanamycin) contained in a culture tube so as to obtain an absorbance of 0.01 at a wavelength of 660 nm (OD660). Culture was performed at a culture temperature of 31.5° C. with shaking at a velocity of 70 rpm by using a small shaking culture apparatus, TVS062CA (Advantec Toyo), and OD660 was measured over time.

The growth patterns in the respective media are shown in FIG. 1. Up to about 40 hours after the start of the culture, there was observed a tendency that the cells showed lower proliferation rate in a medium of lower xylose concentration. However, in the 0.25% (w/v) xylose minimal medium of the lowest xylose concentration, whilst proliferation of the cells was hardly observed up to about 40 hours after the start of the culture, the cells rapidly proliferated thereafter.

(4) Acquisition of Mutant Strain Showing Improved Proliferation Rate in Xylose Minimal Medium The culture broth by the culture for 60 hours in the 0.25% (w/v) xylose minimal medium obtained in (3) mentioned above (FIG. 1) was spread on the CM-Dex agar medium (containing 25 mg/L kanamycin), and culture was performed overnight at 31.5° C. to allow colony formation. The obtained colonies were scraped, and separately sub-cultured on the CM-Dex agar medium (containing 25 mg/L kanamycin) to obtain single clones.

Figure 2:
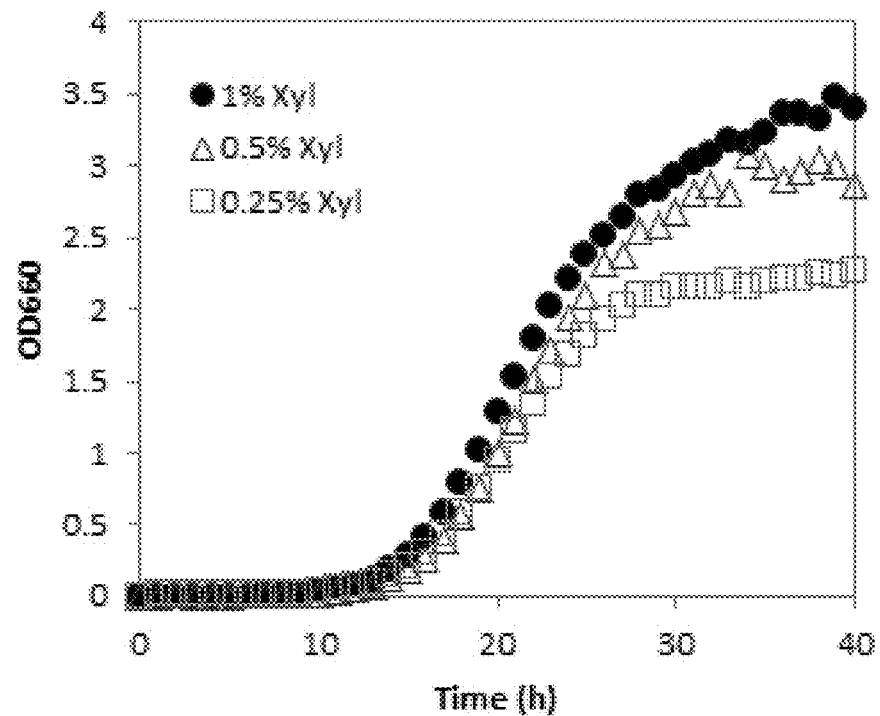
FIG. 2 shows a proliferation profile of the *C. glutamicum* XM strain obtained in the xylose medium.

As a result of culturing some clones obtained as described above in the xylose minimal medium in the same manner as that of (3) mentioned above, there was obtained a mutant strain (XM strain) of which proliferation rate did not significantly reduce even in a medium of low xylose concentration (FIG. 2). This XM strain also showed a markedly improved proliferation rate in the 1.0% (w/v) xylose minimal medium compared with the parent strain (C. glutamicum ATCC13869/pVK9Peftu_xylAB strain) (FIG. 4 (to be explained later)).

(5) Analysis of Mutation Point of Xylose Assimilability-Improved Mutant Strain

Six mutant strains, including the XM strain, showing improved proliferation rate in the xylose minimal medium were obtained by the same test as that of (4) mentioned above. The nucleotide sequences of the chromosomal DNAs of the obtained 6 mutant strains were compared with that of the parent strain by using MiSeq 2000 (Illumina). As a result, a mutation causing mutation of translated amino acid was detected in the NCgl2954 gene on the chromosome for all the mutant strains (Table 1).

TABLE 1

Table 1: Mutations in NCgl2954 genes of mutant strains showing improved proliferation rate in xylose minimal medium

| Mutant strain | Mutation site (Position from start codon) | Type of mutation | Amino acid mutation |
|---|---|---|---|
| XM | 1313 | T → C | L438P |
| 1 | 1092-1093 | Deletion of GC | 495aa → 367aa * |
| 2 | 1092-1093 | Deletion of GC | 495aa → 367aa * |
| 3 | 820 | T → C | W274R |
| 4 | 1129 | T → A | Y377N |
| 5 | 1092-1093 | Deletion of GC | 495aa → 367aa * |

* The mutation of the mutant strains 1, 2, and 5 was a mutation for replacing the leucine residue at the position 365 with a serine residue, the leucine residue at the position 366 with an arginine residue, and the alanine residue at the position 367 with a phenylalanine residue, and truncating the N-terminus of the protein beginning at position 368.

(6) Construction of NCgl2954 Gene-Deficient Strain of C. glutamicum (6-1) Construction of Plasmid pBS4SΔNCgl2954 for Deletion of NCgl2954 Gene A plasmid pBS4SΔNCgl2954 for deletion of the NCgl2954 gene was prepared as follows.

First, PCR was performed by using the chromosomal DNA of the C. glutamicum ATCC 13869 strain as the template, as well as the primers delta_2954_F1 (SEQ ID NO: 5) and delta_2954_MR (SEQ ID NO: 6) to amplify a DNA fragment containing a NCgl2954 gene upstream region. Further, PCR was performed by similarly using the chromosomal DNA of the C. glutamicum ATCC 13869 strain as the template, as well as the primers delta_2954_MF (SEQ ID NO: 7) and delta_2954_R1 (SEQ ID NO: 8) to amplify a DNA fragment containing a NCgl2954 gene downstream region. PrimeSTAR HS DNA Polymerase was used for PCR, and the reactions were performed according to the protocol attached to the enzyme.

The two DNA fragments obtained above were mixed with the plasmid pBS4S (Japanese Patent Laid-open (Kokai) No. 2007-97573, U.S. Published Patent Application No. 20050196846) treated with XbaI, and used for in-fusion reaction with Clontech In-Fusion HD Cloning Kit (Takara Bio) according to the protocol attached to the kit, and E. coli JM109 was transformed with the reaction mixture. The transformants were subjected to selection by culturing them overnight at 37° C. on the LB agar medium (containing 40 mg/L of kanamycin). A plasmid pBS4SΔNCgl2954 corresponding to pBS4S in which the upstream and downstream sequences of the NCgl2954 gene were inserted was obtained from an obtained transformant.

(6-2) Acquisition of NCgl2954 Gene-Deficient Strain

The C. glutamicum ATCC 13869 strain was transformed with pBS4SΔNCgl2954 by the electric pulse method, and cultured at 31.5° C. for two nights on the CM-Dex agar medium (containing 25 mg/L kanamycin) to obtain a one-time recombinant in which pBS4SΔNCgl2954 was incorporated into the chromosome. The obtained one-time recombinant was subcultured on the S10 agar medium to obtain a two-time recombinant C. glutamicum ATCC13869ΔNCgl2954 strain deficient in the NCgl2954 gene region.

(7) Growth of NCgl2954 Gene-Deficient Strain in Xylose Minimal Medium

In the same manner as that of (2-2) mentioned above, the C. glutamicum ATCC13869ΔNCgl2954 strain was transformed with pVK9Peftu_xylAB to obtain a xylose assimilability-imparted and NCgl2954 gene-deficient strain (C. glutamicum ATCC13869ΔNCgl2954/pVK9Peftu_xylAB strain). Growth of this strain in the 0.25% (w/v), 0.5% (w/v), and 1.0% (w/v) xylose minimal media was verified in the same manner as that of (3) mentioned above.

Figure 3:
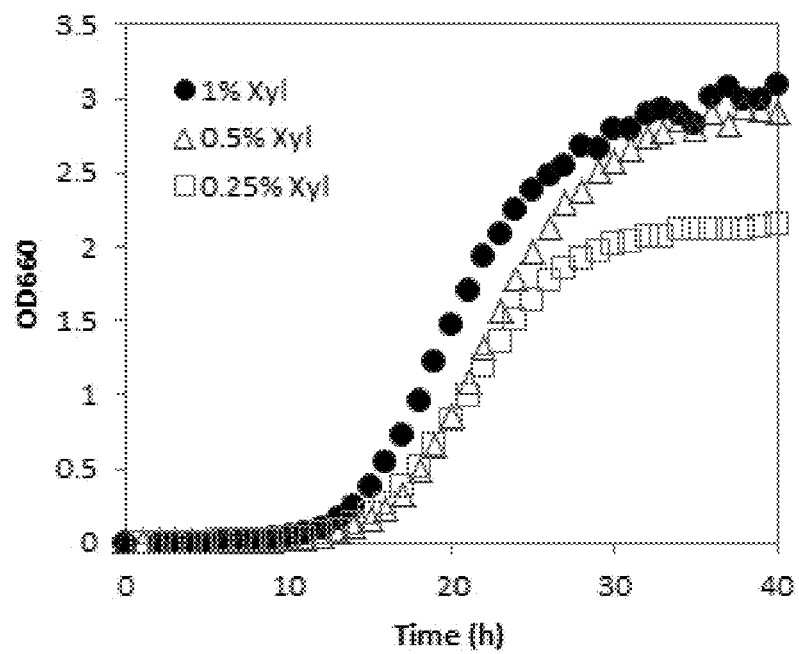
FIG. 3 shows a proliferation profile of the *C. glutamicum* ATCC13869ΔNCgl2954/pVK9Peftu_xylAB strain obtained in the xylose medium.
Figure 4:
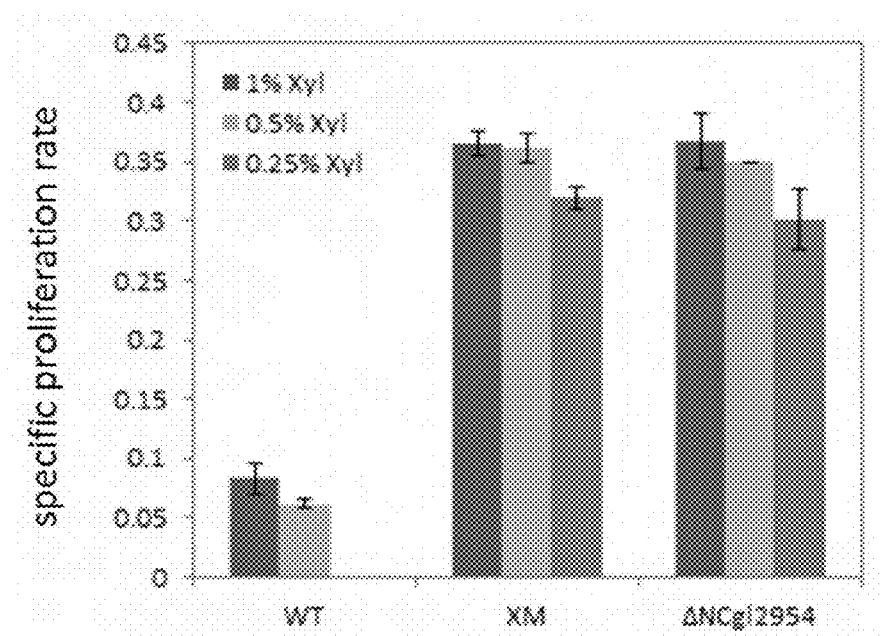
FIG. 4 shows maximum specific proliferation rates observed in 40 hours after the start of the culture in the xylose medium. "WT" represents the *C. glutamicum* ATCC13869/pVK9Peftu_xylAB strain, "XM" represents the *C. glutamicum* XM strain, and "ΔNCgl2954" represents *C. glutamicum* ATCC13869ΔNCgl2954/pVK9Peftu_xylAB strain.

The NCgl2954 gene-deficient strain did not show such marked reduction of proliferation rate as that shown by the wild-type strain (C. glutamicum ATCC13869/ pVK9Peftu_xylAB strain) even in a low concentration xylose minimal medium, and showed a specific proliferation rate comparable to that of the XM strain (FIGS. 3 and 4). On the basis of the above results, it was strongly suggested that the factor for the improvement in the proliferation rate of the XM strain in the xylose minimal medium is inactivation or attenuation of the NCgl2954 gene. By this verification, it was revealed that deletion of the NCgl2954 gene provides improvement in the xylose assimilability.

(8) Influence of Deficiency of NCgl2954 Gene on Glutamic Acid Production Using Xylose as Carbon Source A glutamic acid fermentation test was performed with the NCgl2954 gene-deficient strain (C. glutamicum ATCC13869ΔNCgl2954/pVK9Peftu_xylAB strain) and the wild-type strain (C. glutamicum ATCC13869/ pVK9Peftu_xylAB strain) under biotin limitation in a medium containing xylose to verify influence of deficiency of the NCgl2954 gene on glutamic acid production using xylose as the carbon source.

(8-1) Culture Conditions and Analysis Conditions

The glutamic acid fermentation test was performed by using a jar fermenter. Each strain was cultured overnight at 31.5° C. on the CM-Dex agar medium (containing 25 mg/L kanamycin). After the culture, the cells in 1-cm square on the agar medium were scraped together, and inoculated to 250 mL of the seed medium contained in the jar fermenter. Culture was performed at a culture temperature of 31.5° C., pH 7.2 (adjusted by addition of ammonia gas), aeration rate of 250 mL/min, and stirring number of 700 rpm, and continued until glucose in the medium was completely consumed. Each seed culture broth obtained as described above was inoculated (10% (v/v)) to each of the main media (glucose, xylose, and glucose/xylose) so as to obtain a final volume of 250 mL, and culture was performed at a culture temperature of 31.5° C., pH 7.2 (adjusted by addition of ammonia gas), aeration rate of 250 mL/minute, and stirring number of 700 rpm.

The culture broth was sampled over time, and OD620 of the culture broth, glucose concentration, xylose concentration, and glutamic acid concentration of the culture supernatant were measured. OD620 of the culture broth was measured by using U-2900 (Hitachi High-Technologies). The glutamic acid concentration and glucose concentration in the culture supernatant were measured by using Biotech Analyzer AS-310 (Sakura SI). The xylose concentration in the culture supernatant was measured by using an HPLC system (Pump L-7100, Autosampler L-7200 (both from Hitachi High-Technologies), and Column oven CO 705 (GL Sciences)). The HPLC analysis conditions were as follows: column, SHODEX (SUGAR-G and SUGAR SH1011 (Showa Denko)); column temperature, 50° C.; eluent, $H_2O$; flow rate, 1.0 mL/minute; and detection, RI Detector (Hitachi High-Technologies).

(8-2) Results of Glutamic Acid Production in Glucose Medium

Figure 5A:
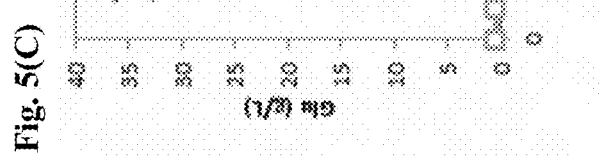
FIG. 5(A)-(C) shows the results of glutamic acid fermentation performed in the glucose medium, specifically 5(A) shows turbidity (OD620) of the culture broth.
Figure 5B:
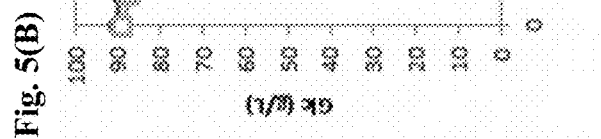
Figure 5C:
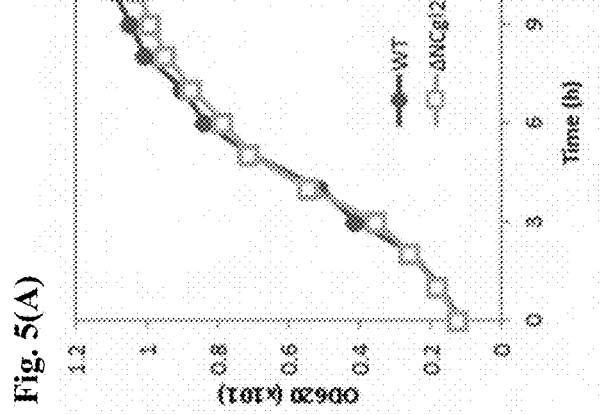

In the glucose medium, both the wild-type strain and the NCgl2954 gene-deficient strain completely consumed glucose contained in the medium after the culture of 11 hours, and difference in glucose consumption rate or glutamic acid productivity was not observed between both the strains (FIG. 5).

(8-3) Results of glutamic acid production in xylose medium

Figure 6A:
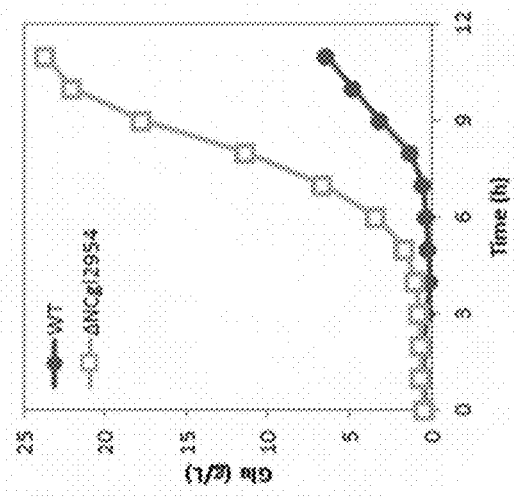
FIG. 6(A)-(C) shows results of glutamic acid fermentation performed in the xylose medium, specifically
Figure 6B:
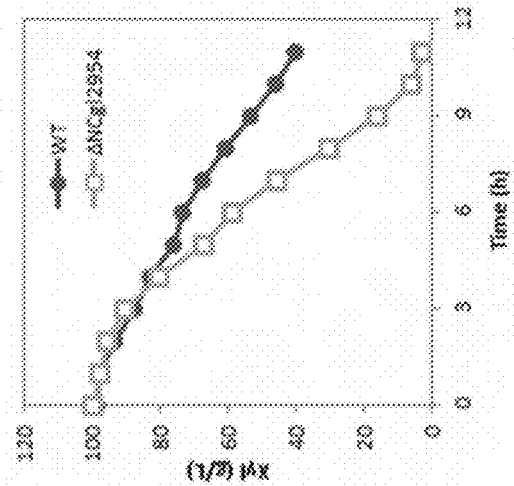
Figure 6C:
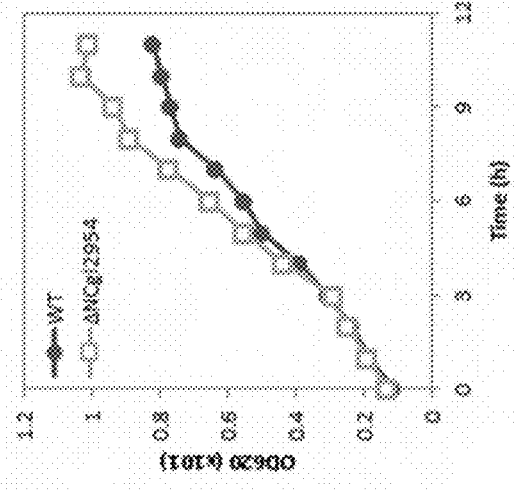
Figure 7A:
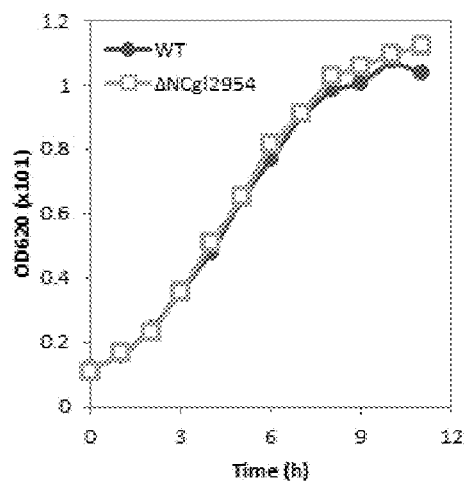
FIG. 7(A)-(D) shows results of glutamic acid fermentation performed in the glucose/xylose medium, specifically 7(A) shows turbidity (OD620) of culture broth, 7(B) shows glucose concentration in the culture supernatant, 7(C) shows xylose concentration in the culture supernatant, and 7(D) shows glutamic acid concentration in the culture supernatant. "WT" represents the *C. glutamicum* ATCC13869/pVK9Peftu_xylAB strain, and "ΔNCgl2954" represents the *C. glutamicum* ATCC13869ΔNCgl2954/pVK9Peftu_xylAB strain.
Figure 7B:
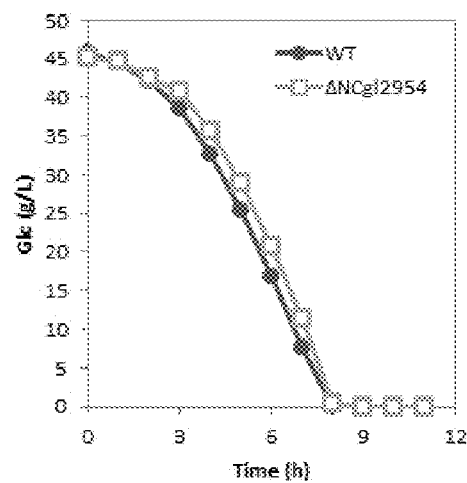
Figure 7C:
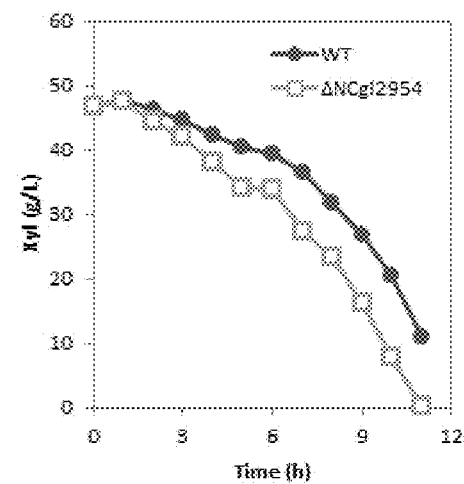
Figure 7D:
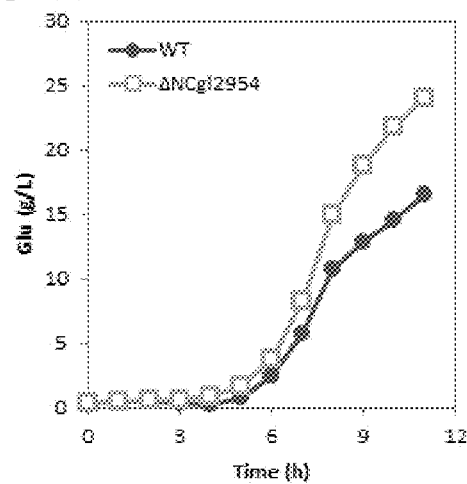

In the xylose medium, the wild-type strain left 40 g/L of xylose in the medium even after the culture of 11 hours, and the amount of the accumulated glutamic acid at that time was 6.4 g/L (FIG. 6). That is, it was confirmed that the xylose assimilation rate of the wild-type strain was markedly lower than the glucose assimilation rate thereof. In contrast, the NCgl2954 gene-deficient strain substantially completely consumed xylose contained in the medium after the culture of 11 hours, and accumulated 23.6 g/L of glutamic acid (FIG. 6). It was thereby revealed that, by the deletion of the NCgl2954 gene, the assimilation rate of xylose was improved, and the productivity of glutamic acid was also improved.

(8-4) Results of Glutamic Acid Production in Glucose/ Xylose Medium

In the glucose/xylose medium, the wild-type strain left 11 g/L of xylose in the medium even after the culture of 11 hours, and the glutamic acid accumulation amount at that time was 16.5 g/L (FIG. 7). In contrast, the NCgl2954 gene-deficient strain completely consumed glucose and xylose after the culture of 11 hours, and accumulated 24.1 g/L of glutamic acid (FIG. 7). As described above, the NCgl2954 gene-deficient strain showed improvement of the xylose consumption rate, especially, even under the presence of glucose, compared with the wild-type strain, and therefore it was demonstrated that the deletion of the NCgl2954 is also effective for simultaneous assimilation of glucose and xylose.

(9) Construction of NXA Pathway-Introduced C. glutamicum

C. glutamicum into which the genes of the NXA pathway have been introduced can be obtained by transformation with the plasmid pVK9Peftu_ccrNXA (WO2013/ 069634A1). pVK9Peftu_ccrNXA contains a sequence consisting of the EF-Tu promoter (Peftu) of C. glutamicum, and the xylXABCD genes encoding the NXA pathway of C. crescentus CB15 (ATCC 19089) and ligated downstream of the promoter. The yagF gene encoding the xylonate dehydratase of E. coli was introduced into the chromosomes of C. glutamicum ATCC 13869 and ATCC13869ΔNCgl2954, and the resultant strains were further transformed with pVK9Peftu_ccrNXA to construct strains that can produce L-glutamic acid from xylose through the NXA pathway. The procedures are shown below.

(9-1) Construction of pBS4SΔxylB_yagF

In order to introduce the yagF gene encoding the xylonate dehydratase of E. coli into the xylB gene region encoding xylulokinase on the chromosome of C. glutamicum ATCC 13869 strain, plasmid pBS4SΔxylB_yagF was constructed as follows.

First, PCR was performed by using the chromosomal DNA of the C. glutamicum ATCC 13869 strain as the template, as well as the primers xylB_F1 (SEQ ID NO: 27) and xylB_MR (SEQ ID NO: 28) to amplify a DNA fragment containing a xylB gene upstream region. PCR was performed by similarly using the chromosomal DNA of the C. glutamicum ATCC 13869 strain as the template, as well as the primers xylB (SEQ ID NO: 29) and xylB_R1 (SEQ ID NO: 30) to amplify a DNA fragment containing a xylB gene downstream region. PrimeSTAR HS DNA Polymerase (Takara Bio) was used for PCR, and the reactions were performed according to the protocol attached to the enzyme.

The two DNA fragments obtained above were mixed with the plasmid pBS4S (Japanese Patent Laid-open (Kokai) No. 2007-97573, U.S. Published Patent Application No.

20050196846) treated with XbaI, and used for in-fusion reaction with Clontech In-Fusion HD Cloning Kit according to the protocol attached to the kit, and the *E. coli* DH5α strain was transformed with the reaction mixture. The transformants were subjected to selection by culturing them overnight at 37° C. on the LB agar medium (containing 40 mg/L of kanamycin). Plasmids were extracted from the obtained transformants, and a plasmid pBS4SΔxylB corresponding to pBS4S in which the upstream and downstream sequences of the xylB gene were inserted was obtained. In pBS4SΔxylB, the XbaI recognition sequence was inserted between the upstream and downstream sequences of the xylB gene.

Then, PCR was performed by using the chromosomal DNA of the *E. coli* MG1655 strain as the template, as well as the primers PcspB_yagF_fw (SEQ ID NO: 31) and yagF_xylB_rv (SEQ ID NO: 32) to amplify a DNA fragment containing the yagF gene. PCR was also performed by using the chromosomal DNA of the *C. glutamicum* ATCC 13869 strain as the template, as well as the primers xylB_PcspB_fw (SEQ ID NO: 33) and PcspB_rv (SEQ ID NO: 34) to amplify a DNA fragment containing the promoter region of the cspB gene (henceforth referred to as "PcspB"). PrimeSTAR HS DNA Polymerase (Takara Bio) was used for PCR, and the reactions were performed according to the protocol attached to the enzyme.

The two DNA fragments obtained above were mixed with the plasmid pBS4SΔxylB treated with XbaI, and used for in-fusion reaction with Clontech In-Fusion HD Cloning Kit (Takara Bio) according to the protocol attached to the kit, and the *E. coli* DH5α strain was transformed with the reaction mixture. The transformants were subjected to selection by culturing them overnight at 37° C. on the LB agar medium (containing 40 mg/L of kanamycin). Plasmids were extracted from the obtained transformants, and a plasmid pBS4SΔxylB_yagF in which a sequence consisting of PcspB and the yagF gene ligated downstream from PcspB was inserted between the upstream and downstream sequences of the xylB gene was obtained. The nucleotide sequences of the cloned cspB promoter (PcspB) and yagF gene are shown as SEQ ID NOS: 47 and 19, respectively.

(2-2) Transformation of *C. glutamicum*

The *C. glutamicum* ATCC 13869 strain was transformed with pBS4SΔxylB_yagF by the electric pulse method, and cultured at 31.5° C. for two nights on the CM-Dex agar medium (containing 25 mg/L kanamycin) to obtain a one-time recombinant in which pBS4SΔxylB_yagF was incorporated into the chromosome. The obtained one-point recombinant was subcultured on the S10 agar medium, and a strain into which the yagF gene was introduced as intended was selected by PCR from strains that grew on the S10 agar medium and showed kanamycin sensitivity. The strain obtained as described above was designated as ATCC13869+D strain. In this strain, the xylB gene region on the chromosome is replaced with the yagF gene.

Then, the ATCC13869+D strain was transformed with pVK9Peftu_ccrNXA, and by selection of the transformants on the CM-Dex agar medium (containing 25 mg/L kanamycin), an NXA pathway-introduced strain, ATCC13869+D/pVK9Peftu_ccrNXA strain, was obtained.

The same procedures as described above were used for the ATCC13869ΔNCgl2954 strain to obtain ATCC13869ΔNCgl2954+D strain in which the yagF gene was introduced into the chromosome, and this strain was transformed with pVK9Peftu_ccrNXA to obtain an NXA pathway-introduced strain, ATCC13869ΔNCgl2954+D/pVK9Peftu_ccrNXA strain.

(10) Influence of Deficiency of NCgl2954 Gene on Glutamic Acid Production Via NXA Pathway In order to confirm effect of deficiency of the NCgl2954 gene on glutamic acid production from xylose via the NXA pathway, a glutamic acid fermentation test under biotin limitation was performed. The culture conditions and analysis conditions are as shown in (8-1).

As a result of culture in the xylose medium, the NCgl2954 gene-deficient strain was able to consume xylose and produce glutamic acid at improved rates, as compared with the strain having an intact NCgl2954 gene (FIG. 8). On the basis of these results, it was demonstrated that deletion of the NCgl2954 gene improves productivity of glutamic acid from xylose not only via the pathway including xylose isomerase and xylulokinase, but also via the NXA pathway.

INDUSTRIAL APPLICABILITY

According to the present invention, xylose assimilability of coryneform bacteria can be improved, and a target substance such as L-amino acids and nucleic acids can be efficiently produced from a raw material containing xylose.

Explanation of Sequence Listing

SEQ ID NO: 1, Primer xylA_SP(2)_4691-80-12
SEQ ID NO: 2, Primer xylAB_ASP_4691-80-13
SEQ ID NO: 3, Primer EFTU_SP_4691-80-1
SEQ ID NO: 4, Primer EFTU_ASP_4691-80-2
SEQ ID NO: 5, Primer delta_2954_F1
SEQ ID NO: 6, Primer delta_2954_MR
SEQ ID NO: 7, Primer delta_2954_MF
SEQ ID NO: 8, Primer delta_2954_R1
SEQ ID NO: 9, Nucleotide sequence of EF-Tu promoter (Peftu)
SEQ ID NO: 10, Nucleotide sequence of xylose operon (xylAB operon) of *E. coli* K-12 MG1655 strain
SEQ ID NO: 11, Amino acid sequence of XylA protein of *E. coli* K-12 MG1655 strain
SEQ ID NO: 12, Amino acid sequence of XylB protein of *E. coli* K-12 MG1655 strain
SEQ ID NO: 13, Nucleotide sequence of NCgl2954 gene of *C. glutamicum* ATCC 13869 strain
SEQ ID NO: 14, Amino acid sequence of protein encoded by NCgl2954 gene of *C. glutamicum* ATCC 13869 strain
SEQ ID NO: 15, Nucleotide sequence of xylB gene of *Sphingomonas elodea*
SEQ ID NO: 16, Amino acid sequence of XylB protein of *Sphingomonas elodea*
SEQ ID NO: 17, Nucleotide sequence of xylC gene of *Sphingomonas elodea*
SEQ ID NO: 18, Amino acid sequence of XylC protein of *Sphingomonas elodea*
SEQ ID NO: 19, Nucleotide sequence of yagF gene of *Escherichia coli* K-12 MG1655 strain
SEQ ID NO: 20, Amino acid sequence of YagF protein of *Escherichia coli* K-12 MG1655 strain
SEQ ID NO: 21, Nucleotide sequence of xylX gene of *Sphingomonas elodea*
SEQ ID NO: 22, Amino acid sequence of XylX protein of *Sphingomonas elodea*
SEQ ID NO: 23, Nucleotide sequence of ycbD gene of *Bacillus subtilis*
SEQ ID NO: 24, Amino acid sequence of YcbD protein of *Bacillus subtilis*
SEQ ID NO: 25, Nucleotide sequence of the yggB gene of *C. glutamicum* ATCC 13869 strain
SEQ ID NO: 26, Amino acid sequence of YggB protein of *C. glutamicum* ATCC 13869 strain SEQ ID NOS: 27 to 34, Primers
SEQ ID NO: 35, Nucleotide sequence of xylB gene of *C. glutamicum* ATCC 13869 strain
SEQ ID NO: 36, Amino acid sequence of XylB protein of *C. glutamicum* ATCC 13869 strain
SEQ ID NO: 37, Nucleotide sequence of xylX gene of *Caulobacter crescentus* CB15 strain
SEQ ID NO: 38, Amino acid sequence of XylX protein of *Caulobacter crescentus* CB15 strain
SEQ ID NO: 39, Nucleotide sequence of xylA gene of *Caulobacter crescentus* CB15 strain
SEQ ID NO: 40, Amino acid sequence of XylA protein of *Caulobacter crescentus* CB15 strain
SEQ ID NO: 41, Nucleotide sequence of xylB gene of *Caulobacter crescentus* CB15 strain
SEQ ID NO: 42, Amino acid sequence of XylB protein of *Caulobacter crescentus* CB15 strain
SEQ ID NO: 43, Nucleotide sequence of xylC gene of *Caulobacter crescentus* CB15 strain
SEQ ID NO: 44, Amino acid sequence of XylC protein of *Caulobacter crescentus* CB15 strain
SEQ ID NO: 45, Nucleotide sequence of xylD gene of *Caulobacter crescentus* CB15 strain
SEQ ID NO: 46, Amino acid sequence of XylD protein of *Caulobacter crescentus* CB15 strain
SEQ ID NO: 47, Nucleotide sequence of cspB promoter (PcspB)

The invention claimed is:

1. A method for producing a target substance comprising:
    culturing a coryneform bacterium having an ability to produce a target substance in a medium containing xylose to produce and accumulate the target substance in the medium; and
    collecting the target substance from the medium,
wherein the bacterium has been modified so that the ability of the bacterium to assimilate xylose is improved as compared with a non-modified bacterium by attenuation of expression or disruption of the NCgl2954 gene on the chromosome of the bacterium.

2. The method according to claim 1, wherein the ability of the bacterium to assimilate xylose has been improved by improving the ability of the bacterium to take up xylose.

3. The method according to claim 1, wherein the NCgl2954 gene is a DNA encoding a protein selected from the group consisting of:
    (A) a protein comprising the amino acid sequence of SEQ ID NO: 14;
    (B) a protein comprising the amino acid sequence of SEQ ID NO: 14, but which includes substitution, deletion, insertion, or addition of one or several amino acid residues, and wherein when said protein is deleted from the coryneform bacterium, the bacterium has an improved ability to assimilate xylose; and
    (C) a protein comprising an amino acid sequence having an identity of 90% or higher to the amino acid sequence of SEQ ID NO: 14, and wherein when said protein is deleted from the coryneform bacterium, the bacterium has an improved ability to assimilate xylose.

4. The method according to claim 1, wherein said attenuation of expression or disruption is attained by introduction of a mutation into a coding region and/or an expression control region of the NCgl2954 gene that results in a mutation of the encoded amino acid sequence, and wherein the mutation of the encoded amino acid sequence is selected from the group consisting of:
    (1) replacement of an amino acid residue corresponding to the proline leucine residue at position 438 of SEQ ID NO: 14 with an amino acid residue other than a leucine residue;
    (2) replacement of an amino acid residue corresponding to the tryptophan residue at position 274 of SEQ ID NO: 14 with an amino acid residue other than a tryptophan residue;
    (3) replacement of an amino acid residue corresponding to the tyrosine residue at position 377 of SEQ ID NO: 14 with an amino acid residue other than a tyrosine residue;
    (4) replacement of an amino acid residue corresponding to the leucine residue at position 365 of SEQ ID NO: 14 with an amino acid residue other than a leucine residue;
    (5) replacement of an amino acid residue corresponding to the leucine residue at position 366 of SEQ ID NO: 14 with an amino acid residue other than a leucine residue;
    (6) replacement of an amino acid residue corresponding to the alanine residue at position 367 of SEQ ID NO: 14 with an amino acid residue other than an alanine residue;
    (7) truncation of the N-terminus amino acid residues beginning with the amino acid residue at position 368 of SEQ ID NO: 14; and
    (8) combinations thereof.

5. The method according to claim 4, wherein:
    said amino acid residue other than a leucine residue at position 438 of SEQ ID NO: 14 is proline;
    said amino acid residue other than a tryptophan residue is arginine;
    said amino acid residue other than a tyrosine residue is asparagine;

said amino acid residue other than a leucine residue at position 365 of SEQ ID NO: 14 is serine;

said amino acid residue other than a leucine residue at position 366 of SEQ ID NO: 14 is arginine; and said amino acid residue other than an alanine residue is phenylalanine.

6. The method according to claim 1, wherein the bacterium has been further modified so that activities or activity of xylose isomerase and/or xylulokinase is increased.

7. The method according to claim 6, wherein the xylose isomerase is a protein selected from the group consisting of:
   (A) a protein comprising the amino acid sequence of SEQ ID NO: 11;
   (B) a protein comprising the amino acid sequence of SEQ ID NO: 11, but which includes substitution, deletion, insertion, or addition of one or several amino acid residues, and wherein said protein has xylose isomerase activity; and
   (C) a protein comprising an amino acid sequence having an identity of 90% or higher to the amino acid sequence of SEQ ID NO: 11, and wherein said protein has xylose isomerase activity.

8. The method according to claim 6, wherein the xylulokinase is a protein selected from the group consisting of:
   (A) a protein comprising the amino acid sequence of SEQ ID NO: 12;
   (B) a protein comprising the amino acid sequence of SEQ ID NO: 12, but which includes substitution, deletion, insertion, or addition of one or several amino acid residues, and wherein said protein has xylulokinase activity; and
   (C) a protein comprising an amino acid sequence having an identity of 90% or higher to the amino acid sequence of SEQ ID NO: 12, and wherein said protein has xylulokinase activity.

9. The method according to claim 1, wherein the bacterium has been further modified so that activity or activities of an enzyme selected from the group consisting of xylose dehydrogenase, xylonolactonase, xylonate dehydratase, 2-keto-3-deoxyxylonate dehydratase, α-ketoglutaric semialdehyde dehydrogenase, and combinations thereof is/are increased.

10. The method according to claim 9, wherein the xylonate dehydratase, 2-keto-3-deoxyxylonate dehydratase, and α-ketoglutaric semialdehyde dehydrogenase are derived from an *Escherichia* bacterium, *Sphingomonas* bacterium, and *Bacillus* bacterium, respectively.

11. The method according to claim 9, wherein the xylose dehydrogenase is a protein selected from the group consisting of:
   (A) a protein comprising the amino acid sequence of SEQ ID NO: 16 or 42;
   (B) a protein comprising the amino acid sequence of SEQ ID NO: 16 or 42, but which includes substitution, deletion, insertion, or addition of one or several amino acid residues, and wherein said protein has xylose dehydrogenase activity; and
   (C) a protein comprising an amino acid sequence having an identity of 90% or higher to the amino acid sequence of SEQ ID NO: 16 or 42, and wherein said protein has xylose dehydrogenase activity.

12. The method according to claim 9, wherein the xylonolactonase is a protein selected from the group consisting of:
   (A) a protein comprising the amino acid sequence of SEQ ID NO: 18 or 44;
   (B) a protein comprising the amino acid sequence of SEQ ID NO: 18 or 44, but which includes substitution, deletion, insertion, or addition of one or several amino acid residues, and wherein said protein has xylonolactonase activity; and
   (C) a protein comprising an amino acid sequence having an identity of 90% or higher to the amino acid sequence of SEQ ID NO: 18 or 44, and wherein said protein has xylonolactonase activity.

13. The method according to claim 9, wherein the xylonate dehydratase is a protein selected from the group consisting of:
   (A) a protein comprising the amino acid sequence of SEQ ID NO: 20 or 46;
   (B) a protein comprising the amino acid sequence of SEQ ID NO: 20 or 46, but which includes substitution, deletion, insertion, or addition of one or several amino acid residues, and wherein said protein has xylonate dehydratase activity; and
   (C) a protein comprising an amino acid sequence having an identity of 90% or higher to the amino acid sequence of SEQ ID NO: 20 or 46, and wherein said protein has xylonate dehydratase activity.

14. The method according to claim 9, wherein the 2-keto-3-deoxyxylonate dehydratase is a protein selected from the group consisting of:
   (A) a protein comprising the amino acid sequence of SEQ ID NO: 22 or 38;
   (B) a protein comprising the amino acid sequence of SEQ ID NO: 22 or 38, but which includes substitution, deletion, insertion, or addition of one or several amino acid residues, and wherein said protein has 2-keto-3-deoxyxylonate dehydratase activity; and
   (C) a protein comprising an amino acid sequence having an identity of 90% or higher to the amino acid sequence of SEQ ID NO: 22 or 38, and wherein said protein has 2-keto-3-deoxyxylonate dehydratase activity.

15. The method according to claim 9, wherein the α-ketoglutaric semialdehyde dehydrogenase is a protein selected from the group consisting of:
   (A) a protein comprising the amino acid sequence of SEQ ID NO: 24 or 40;
   (B) a protein comprising the amino acid sequence of SEQ ID NO: 24 or 40, but which includes substitution, deletion, insertion, or addition of one or several amino acid residues, and wherein said protein has α-ketoglutaric semialdehyde dehydrogenase activity; and
   (C) a protein comprising an amino acid sequence having an identity of 90% or higher to the amino acid sequence of SEQ ID NO: 24 or 40, and wherein said protein has α-ketoglutaric semialdehyde dehydrogenase activity.

16. The method according to claim 1, wherein the target substance is selected from the group consisting of an amino acid, nucleic acid, and peptide.

17. The method according to claim 16, wherein the target substance is an amino acid selected from the group consisting of L-glutamic acid, L-glutamine, L-arginine, and L-lysine.

18. The method according to claim 16, wherein the target substance is a purine nucleoside selected from the group consisting of inosine, xanthosine, guanosine, and adenosine.

19. The method according to claim 16, wherein the target substance is a purine nucleotide selected from the group consisting of inosinic acid, xanthylic acid, and guanylic acid.

20. The method according to claim 1, wherein the bacterium is a *Corynebacterium* bacterium.

21. The method according to claim 20, wherein the bacterium is *Corynebacterium glutamicum*.

\* \* \* \* \*

```
                             SEQUENCE LISTING

<160> NUMBER OF SEQ IDS NOS: 47

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
ccaggaggac atacaatgca agcctatttt gacca                              35

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
gcaggtcgac tctagttacg ccattaatgg cagaa                              35

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
ccggggatcc tctagagatc gtttagatcc gaagg                              35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
aaaataggct tgcattgtat gtcctcctgg acttc                              35

<210> SEQ ID NO 5
<211> LENGTH: 39
<212> TYPE: DNA
<213> ORGANISM: Artificial Sequence
<220> FEATURE:
<223> OTHER INFORMATION: primer

<400> SEQUENCE: 5
tacccgggga tcctctagca ataactccgt gtagggtga                          39
```

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
tgctctagaa tttgatccgt ttttctaaag gttg                          34

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
tcaaattcta gagcaattca ttgacgtaca aagtg                         35

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
tgcaggtcga ctctagctgt ggccatcctt gacggga                       37

<210> SEQ ID NO 9
<211> LENGTH: 362
<212> TYPE: DNA
<213> ORGANISM: Corynebacterium glutamicum

<400> SEQUENCE: 9
agatcgttta gatccgaagg aaaacgtcga aaagcaattt gcttttcgac gccccacccc    60
gcgcgtttta gcgtgtcagt aggcgcgtag ggtaagtggg gtagcggctt gttagatatc   120
ttgaaatcgg ctttcaacag cattgatttc gatgtattta gctggccgtt accctgcgaa   180
tgtccacagg gtagctggta gtttgaaaat caacgccgtt gcccttagga ttcagtaact   240
ggcacatttt gtaatgcgct agatctgtgt gctcagtctt ccaggctgct tatcacagtg   300
aaagcaaaac caattcgtgg ctgcgaaagt cgtagccacc acgaagtcca ggaggacata   360
ca                                                                  362

<210> SEQ ID NO 10
<211> LENGTH: 2849
<212> TYPE: DNA
<213> ORGANISM: Escherichia coli
<220> FEATURE:
<221> NAME/KEY: CDS
<222> LOCATION: (1)..(1323)
<220> FEATURE:
<221> NAME/KEY: CDS
<222> LOCATION: (1395)..(2849)

<400> SEQUENCE: 10 atg caa gcc tat ttt gac cag ctc gat cgc gtt cgt tat gaa ggc tca      48
Met Gln Ala Tyr Phe Asp Gln Leu Asp Arg Val Arg Tyr Glu Gly Ser
1               5                   10                  15 aaa tcc tca aac ccg tta gca ttc cgt cac tac aat ccc gac gaa ctg      96
Lys Ser Ser Asn Pro Leu Ala Phe Arg His Tyr Asn Pro Asp Glu Leu

```
                    20                  25                  30
gtg ttg ggt aag cgt atg gaa gag cac ttg cgt ttt gcc gcc tgc tac    144
Val Leu Gly Lys Arg Met Glu Glu His Leu Arg Phe Ala Ala Cys Tyr
         35                  40                  45 tgg cac acc ttc tgc tgg aac ggg gcg gat atg ttt ggt gtg ggg gcg    192
Trp His Thr Phe Cys Trp Asn Gly Ala Asp Met Phe Gly Val Gly Ala
 50                  55                  60 ttt aat cgt ccg tgg cag cag cct ggt gag gca ctg gcg ttg gcg aag    240
Phe Asn Arg Pro Trp Gln Gln Pro Gly Glu Ala Leu Ala Leu Ala Lys
 65                  70                  75                  80 cgt aaa gca gat gtc gca ttt gag ttt ttc cac aag tta cat gtg cca    288
Arg Lys Ala Asp Val Ala Phe Glu Phe Phe His Lys Leu His Val Pro
                     85                  90                  95 ttt tat tgc ttc cac gat gtg gat gtt tcc cct gag ggc gcg tcg tta    336
Phe Tyr Cys Phe His Asp Val Asp Val Ser Pro Glu Gly Ala Ser Leu
                100                 105                 110 aaa gag tac atc aat aat ttt gcg caa atg gtt gat gtc ctg gca ggc    384
Lys Glu Tyr Ile Asn Asn Phe Ala Gln Met Val Asp Val Leu Ala Gly
                115                 120                 125 aag caa gaa gag agc ggc gtg aag ctg ctg tgg gga acg gcc aac tgc    432
Lys Gln Glu Glu Ser Gly Val Lys Leu Leu Trp Gly Thr Ala Asn Cys
130                 135                 140 ttt aca aac cct cgc tac ggc gcg ggt gcg gcg acg aac cca gat cct    480
Phe Thr Asn Pro Arg Tyr Gly Ala Gly Ala Ala Thr Asn Pro Asp Pro
145                 150                 155                 160 gaa gtc ttc agc tgg gcg gca acg caa gtt gtt aca gcg atg gaa gca    528
Glu Val Phe Ser Trp Ala Ala Thr Gln Val Val Thr Ala Met Glu Ala
                165                 170                 175 acc cat aaa ttg ggc ggt gaa aac tat gtc ctg tgg ggc ggt cgt gaa    576
Thr His Lys Leu Gly Gly Glu Asn Tyr Val Leu Trp Gly Gly Arg Glu
                180                 185                 190 ggt tac gaa acg ctg tta aat acc gac ttg cgt cag gag cgt gaa caa    624
Gly Tyr Glu Thr Leu Leu Asn Thr Asp Leu Arg Gln Glu Arg Glu Gln
                195                 200                 205 ctg ggc cgc ttt atg cag atg gtg gtt gag cat aaa cat aaa atc ggt    672
Leu Gly Arg Phe Met Gln Met Val Val Glu His Lys His Lys Ile Gly
210                 215                 220 ttc cag ggc acg ttg ctt atc gaa ccg aaa ccg caa gaa ccg acc aaa    720
Phe Gln Gly Thr Leu Leu Ile Glu Pro Lys Pro Gln Glu Pro Thr Lys
225                 230                 235                 240 cat caa tat gat tac gat gcc gcg acg gtc tat ggc ttc ctg aaa cag    768
His Gln Tyr Asp Tyr Asp Ala Ala Thr Val Tyr Gly Phe Leu Lys Gln
                245                 250                 255 ttt ggt ctg gaa aaa gag att aaa ctg aac att gaa gct aac cac gcg    816
Phe Gly Leu Glu Lys Glu Ile Lys Leu Asn Ile Glu Ala Asn His Ala
                260                 265                 270 acg ctg gca ggt cac tct ttc cat cat gaa ata gcc acc gcc att gcg    864
Thr Leu Ala Gly His Ser Phe His His Glu Ile Ala Thr Ala Ile Ala
                275                 280                 285 ctt ggc ctg ttc ggt tct gtc gac gcc aac cgt ggc gat gcg caa ctg    912
Leu Gly Leu Phe Gly Ser Val Asp Ala Asn Arg Gly Asp Ala Gln Leu
                290                 295                 300 ggc tgg gac acc gac cag ttc ccg aac agt gtg gaa gag aat gcg ctg    960
Gly Trp Asp Thr Asp Gln Phe Pro Asn Ser Val Glu Glu Asn Ala Leu
305                 310                 315                 320 gtg atg tat gaa att ctc aaa gca ggc ggt ttc acc acc ggt ggt ctg   1008
Val Met Tyr Glu Ile Leu Lys Ala Gly Gly Phe Thr Thr Gly Gly Leu
                325                 330                 335 aac ttc gat gcc aaa gta cgt cgt caa agt act gat aaa tat gat ctg   1056
Asn Phe Asp Ala Lys Val Arg Arg Gln Ser Thr Asp Lys Tyr Asp Leu
```

```
                Asn Phe Asp Ala Lys Val Arg Arg Gln Ser Thr Asp Lys Tyr Asp Leu
                            340                 345                 350 ttt tac ggt cat atc ggc gcg atg gat acg atg gca ctg gcg ctg aaa          1104
Phe Tyr Gly His Ile Gly Ala Met Asp Thr Met Ala Leu Ala Leu Lys
            355                 360                 365 att gca gcg cgc atg att gaa gat ggc gag ctg gat aaa cgc atc gcg          1152
Ile Ala Ala Arg Met Ile Glu Asp Gly Glu Leu Asp Lys Arg Ile Ala
370                 375                 380 cag cgt tat tcc ggc tgg aat agc gaa ttg ggc cag caa atc ctg aaa          1200
Gln Arg Tyr Ser Gly Trp Asn Ser Glu Leu Gly Gln Gln Ile Leu Lys
385                 390                 395                 400 ggc caa atg tca ctg gca gat tta gcc aaa tat gct cag gaa cat cat          1248
Gly Gln Met Ser Leu Ala Asp Leu Ala Lys Tyr Ala Gln Glu His His
                405                 410                 415 ttg tct ccg gtg cat cag agt ggt cgc cag gaa caa ctg gaa aat ctg          1296
Leu Ser Pro Val His Gln Ser Gly Arg Gln Glu Gln Leu Glu Asn Leu
            420                 425                 430 gta aac cat tat ctg ttc gac aaa taa cggctaactg tgcagtccgt                1343
Val Asn His Tyr Leu Phe Asp Lys
        435                 440 tggcccggtt atcggtagcg ataccgggca ttttttaag gaacgatcga t atg tat          1400
                                                         Met Tyr atc ggg ata gat ctt ggc acc tcg ggc gta aaa gtt att ttg ctc aac          1448
Ile Gly Ile Asp Leu Gly Thr Ser Gly Val Lys Val Ile Leu Leu Asn
            445                 450                 455 gag cag ggt gag gtg gtt gct gcg caa acg gaa aag ctg acc gtt tcg          1496
Glu Gln Gly Glu Val Val Ala Ala Gln Thr Glu Lys Leu Thr Val Ser
460                 465                 470 cgc ccg cat cca ctc tgg tcg gaa caa gac ccg gaa cag tgg tgg cag          1544
Arg Pro His Pro Leu Trp Ser Glu Gln Asp Pro Glu Gln Trp Trp Gln
475                 480                 485                 490 gca act gat cgc gca atg aaa gct ctg ggc gat cag cat tct ctg cag          1592
Ala Thr Asp Arg Ala Met Lys Ala Leu Gly Asp Gln His Ser Leu Gln
                495                 500                 505 gac gtt aaa gca ttg ggt att gcc ggc cag atg cac gga gca acc ttg          1640
Asp Val Lys Ala Leu Gly Ile Ala Gly Gln Met His Gly Ala Thr Leu
            510                 515                 520 ctg gat gct cag caa cgg gtg tta cgc cct gcc att ttg tgg aac gac          1688
Leu Asp Ala Gln Gln Arg Val Leu Arg Pro Ala Ile Leu Trp Asn Asp
                525                 530                 535 ggg cgc tgt gcg caa gag tgc act ttg ctg gaa gcg cga gtt ccg caa          1736
Gly Arg Cys Ala Gln Glu Cys Thr Leu Leu Glu Ala Arg Val Pro Gln
540                 545                 550 tcg cgg gtg att acc ggc aac ctg atg atg ccc gga ttt act gcg cct          1784
Ser Arg Val Ile Thr Gly Asn Leu Met Met Pro Gly Phe Thr Ala Pro
555                 560                 565                 570 aaa ttg cta tgg gtt cag cgg cat gag ccg gag ata ttc cgt caa atc          1832
Lys Leu Leu Trp Val Gln Arg His Glu Pro Glu Ile Phe Arg Gln Ile
            575                 580                 585 gac aaa gta tta tta ccg aaa gat tac ttg cgt ctg cgt atg acg ggg          1880
Asp Lys Val Leu Leu Pro Lys Asp Tyr Leu Arg Leu Arg Met Thr Gly
            590                 595                 600 gag ttt gcc agc gat atg tct gac gca gct ggc acc atg tgg ctg gat          1928
Glu Phe Ala Ser Asp Met Ser Asp Ala Ala Gly Thr Met Trp Leu Asp
            605                 610                 615 gtc gca aag cgt gac tgg agt gac gtc atg ctg cag gct tgc gac tta          1976
Val Ala Lys Arg Asp Trp Ser Asp Val Met Leu Gln Ala Cys Asp Leu
            620                 625                 630 tct cgt gac cag atg ccc gca tta tac gaa ggc agc gaa att act ggt          2024
```

```
Ser Arg Asp Gln Met Pro Ala Leu Tyr Glu Gly Ser Glu Ile Thr Gly
635                 640                 645                 650 gct ttg tta cct gaa gtt gcg aaa gcg tgg ggt atg gcg acg gtg cca    2072
Ala Leu Leu Pro Glu Val Ala Lys Ala Trp Gly Met Ala Thr Val Pro
                655                 660                 665 gtt gtc gca ggc ggt ggc gac aat gca gct ggt gca gtt ggt gtg gga    2120
Val Val Ala Gly Gly Gly Asp Asn Ala Ala Gly Ala Val Gly Val Gly
            670                 675                 680 atg gtt gat gct aat cag gca atg tta tcg ctg ggg acg tcg ggg gtc    2168
Met Val Asp Ala Asn Gln Ala Met Leu Ser Leu Gly Thr Ser Gly Val
        685                 690                 695 tat ttt gct gtc agc gaa ggg ttc tta agc aag cca gaa agc gcc gta    2216
Tyr Phe Ala Val Ser Glu Gly Phe Leu Ser Lys Pro Glu Ser Ala Val
    700                 705                 710 cat agc ttt tgc cat gcg cta ccg caa cgt tgg cat tta atg tct gtg    2264
His Ser Phe Cys His Ala Leu Pro Gln Arg Trp His Leu Met Ser Val
715                 720                 725                 730 atg ctg agt gca gcg tcg tgt ctg gat tgg gcc gcg aaa tta acc ggc    2312
Met Leu Ser Ala Ala Ser Cys Leu Asp Trp Ala Ala Lys Leu Thr Gly
                735                 740                 745 ctg agc aat gtc cca gct tta atc gct gca gct caa cag gct gat gaa    2360
Leu Ser Asn Val Pro Ala Leu Ile Ala Ala Ala Gln Gln Ala Asp Glu
            750                 755                 760 agt gcc gag cca gtt tgg ttt ctg cct tat ctt tcc ggc gag cgt acg    2408
Ser Ala Glu Pro Val Trp Phe Leu Pro Tyr Leu Ser Gly Glu Arg Thr
        765                 770                 775 cca cac aat aat ccc cag gcg aag ggg gtt ttc ttt ggt ttg act cat    2456
Pro His Asn Asn Pro Gln Ala Lys Gly Val Phe Phe Gly Leu Thr His
    780                 785                 790 caa cat ggc ccc aat gaa ctg gcg cga gca gtg ctg gaa ggc gtg ggt    2504
Gln His Gly Pro Asn Glu Leu Ala Arg Ala Val Leu Glu Gly Val Gly
795                 800                 805                 810 tat gcg ctg gca gat ggc atg gat gtc gtg cat gcc tgc ggt att aaa    2552
Tyr Ala Leu Ala Asp Gly Met Asp Val Val His Ala Cys Gly Ile Lys
                815                 820                 825 ccg caa agt gtt acg ttg att ggg ggc ggg gcg cgt agt gag tac tgg    2600
Pro Gln Ser Val Thr Leu Ile Gly Gly Gly Ala Arg Ser Glu Tyr Trp
            830                 835                 840 cgt cag atg ctg gcg gat atc agc ggt cag cag ctc gat tac cgt acg    2648
Arg Gln Met Leu Ala Asp Ile Ser Gly Gln Gln Leu Asp Tyr Arg Thr
        845                 850                 855 ggg ggt gat gtg ggg cca gca ctg ggc gca gca agg ctg gcg cag atc    2696
Gly Gly Asp Val Gly Pro Ala Leu Gly Ala Ala Arg Leu Ala Gln Ile
    860                 865                 870 gcg gcg aat cca gag aaa tcg ctc att gaa ttg ttg ccg caa cta ccg    2744
Ala Ala Asn Pro Glu Lys Ser Leu Ile Glu Leu Leu Pro Gln Leu Pro
875                 880                 885                 890 tta gaa cag tcg cat cta cca gat gcg cag cgt tat gcc gct tat cag    2792
Leu Glu Gln Ser His Leu Pro Asp Ala Gln Arg Tyr Ala Ala Tyr Gln
                895                 900                 905 cca cga cga gaa acg ttc cgt cgc ctc tat cag caa ctt ctg cca tta    2840
Pro Arg Arg Glu Thr Phe Arg Arg Leu Tyr Gln Gln Leu Leu Pro Leu
            910                 915                 920 atg gcg taa                                                        2849
Met Ala

<210> SEQ ID NO 11
<211> LENGTH: 440
<212> TYPE: PRT
<213> ORGANISM: Escherichia coli
```

-continued

```
<400> SEQUENCE: 11

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
    370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
```

```
                         405                 410                 415
Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 12
<211> LENGTH: 484
<212> TYPE: PRT
<213> ORGANISM: Escherichia coli

<400> SEQUENCE: 12

Met Tyr Ile Gly Ile Asp Leu Gly Thr Ser Gly Val Lys Val Ile Leu
1               5                   10                  15

Leu Asn Glu Gln Gly Glu Val Ala Ala Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
    210                 215                 220

Val Pro Val Val Ala Gly Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285

Ser Val Met Leu Ser Ala Ala Ser Cys Leu Asp Trp Ala Ala Lys Leu
    290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335
```

```
Arg Thr Pro His Asn Asn Pro Gln Ala Lys Gly Val Phe Phe Gly Leu
                340                 345                 350
Thr His Gln His Gly Pro Asn Glu Leu Ala Arg Ala Val Leu Glu Gly
            355                 360                 365
Val Gly Tyr Ala Leu Ala Asp Gly Met Asp Val Val His Ala Cys Gly
        370                 375                 380
Ile Lys Pro Gln Ser Val Thr Leu Ile Gly Gly Ala Arg Ser Glu
385                 390                 395                 400
Tyr Trp Arg Gln Met Leu Ala Asp Ile Ser Gln Gln Leu Asp Tyr
                405                 410                 415
Arg Thr Gly Gly Asp Val Gly Pro Ala Leu Gly Ala Ala Arg Leu Ala
            420                 425                 430
Gln Ile Ala Ala Asn Pro Glu Lys Ser Leu Ile Glu Leu Leu Pro Gln
        435                 440                 445
Leu Pro Leu Glu Gln Ser His Leu Pro Asp Ala Gln Arg Tyr Ala Ala
    450                 455                 460
Tyr Gln Pro Arg Arg Glu Thr Phe Arg Arg Leu Tyr Gln Gln Leu Leu
465                 470                 475                 480
Pro Leu Met Ala

<210> SEQ ID NO 13
<211> LENGTH: 1485
<212> TYPE: DNA
<213> ORGANISM: Corynebacterium glutamicum
<220> FEATURE:
<221> NAME/KEY: CDS
<222> LOCATION: (1)..(1485)

<400> SEQUENCE: 13 atg caa acc att cag cta ctc acc aaa gca gga ctt tta gta gac gca     48
Met Gln Thr Ile Gln Leu Leu Thr Lys Ala Gly Leu Leu Val Asp Ala
1               5                   10                  15 ctt tcg gca ggg cca aat act cat tct gag ctg gca aaa cag tta aat     96
Leu Ser Ala Gly Pro Asn Thr His Ser Glu Leu Ala Lys Gln Leu Asn
            20                  25                  30 gag ccg aga tcg tca atc tat cga ata acg tct tcg tta gag gaa gtc    144
Glu Pro Arg Ser Ser Ile Tyr Arg Ile Thr Ser Ser Leu Glu Glu Val
        35                  40                  45 ggg tac gtc aac atc acc agc agt ggc ttg tta ggg ctt ggc gta aac    192
Gly Tyr Val Asn Ile Thr Ser Ser Gly Leu Leu Gly Leu Gly Val Asn
    50                  55                  60 atc ctc cac ctg ggc gaa agt gcc gtt gac gcc ctg ctt aac aga act    240
Ile Leu His Leu Gly Glu Ser Ala Val Asp Ala Leu Leu Asn Arg Thr
65                  70                  75                  80 tta ttg cgg gaa aaa tta ggc tgg ctc cgc gat cag ctg ggc atg acc    288
Leu Leu Arg Glu Lys Leu Gly Trp Leu Arg Asp Gln Leu Gly Met Thr
                85                  90                  95 gct ttc ttt tgc acc ctc caa gat gac cgc atc atc agt ctg gat tgg    336
Ala Phe Phe Cys Thr Leu Gln Asp Asp Arg Ile Ile Ser Leu Asp Trp
            100                 105                 110 cag gag ggc gca gat att gat ctg att tac ctc gcc cct ggc cgc acg    384
Gln Glu Gly Ala Asp Ile Asp Leu Ile Tyr Leu Ala Pro Gly Arg Thr
        115                 120                 125 ctc ccg tcc caa aaa ggt gca gtc tcc cat gtg ctc cag ggc aaa gac    432
Leu Pro Ser Gln Lys Gly Ala Val Ser His Val Leu Gln Gly Lys Asp
    130                 135                 140 ctg cgc aaa ggg tgg agt att gat cac ggc gag ctc acc gtt gga gtg    480
Leu Arg Lys Gly Trp Ser Ile Asp His Gly Glu Leu Thr Val Gly Val
145                 150                 155                 160
```

```
                                                                      -continued tca tcc tta gct gtc gcg gtg aaa aac gct aac ggc gac gtc tta ggt           528
Ser Ser Leu Ala Val Ala Val Lys Asn Ala Asn Gly Asp Val Leu Gly
                165                 170                 175 gca gtg gcg gta gct ggg ctg agt gca agc gtt gag agc aaa atc gac           576
Ala Val Ala Val Ala Gly Leu Ser Ala Ser Val Glu Ser Lys Ile Asp
        180                 185                 190 acc atc cgg gac acg ttg aag gaa act gcg tgc gca atc gca aac atg           624
Thr Ile Arg Asp Thr Leu Lys Glu Thr Ala Cys Ala Ile Ala Asn Met
        195                 200                 205 ccg cca gcc aaa acg cag gaa ttc gat cca tca cga atc aag gaa ccc           672
Pro Pro Ala Lys Thr Gln Glu Phe Asp Pro Ser Arg Ile Lys Glu Pro
        210                 215                 220 aat tca cct tcg gta atc acc aaa gcg gca acg ctc atg gat gtg ctc           720
Asn Ser Pro Ser Val Ile Thr Lys Ala Ala Thr Leu Met Asp Val Leu
225                 230                 235                 240 cgc act gaa ggt ccc acc aac tcc gct cgc cta gct gag gtg ctg ggg           768
Arg Thr Glu Gly Pro Thr Asn Ser Ala Arg Leu Ala Glu Val Leu Gly
                245                 250                 255 gag ccg atc agt tcg gtg tac aga atg ctc cac acc tta acc gcg atc           816
Glu Pro Ile Ser Ser Val Tyr Arg Met Leu His Thr Leu Thr Ala Ile
                260                 265                 270 ggg tgg gtt gag cag gac gga aag cgc ggc tcc tat cgc gtt ggc cta           864
Gly Trp Val Glu Gln Asp Gly Lys Arg Gly Ser Tyr Arg Val Gly Leu
        275                 280                 285 gcc atg ctc aca ctt gcc gaa tcg caa ttg cgc cat atg gat ctc cgc           912
Ala Met Leu Thr Leu Ala Glu Ser Gln Leu Arg His Met Asp Leu Arg
        290                 295                 300 aag atc gcc gca ctg acc atg cgg aaa att cac gca ctc act ggt gaa           960
Lys Ile Ala Ala Leu Thr Met Arg Lys Ile His Ala Leu Thr Gly Glu
305                 310                 315                 320 acc aca ttt ttg tgt gtc cgc cac ggc att cgc gcg gtg tgc atc gag          1008
Thr Thr Phe Leu Cys Val Arg His Gly Ile Arg Ala Val Cys Ile Glu
                325                 330                 335 cga gtt gat ggc gat cgc gtg aat agt cga gtt ctc caa ttg gga acc          1056
Arg Val Asp Gly Asp Arg Val Asn Ser Arg Val Leu Gln Leu Gly Thr
                340                 345                 350 tcg ctg ccc ctt cat gtc ggt gcc gca ccg cgc gcg ctt ctc gct ttt          1104
Ser Leu Pro Leu His Val Gly Ala Ala Pro Arg Ala Leu Leu Ala Phe
        355                 360                 365 gag gga cgc cgg gcc tgg gaa acg tat gcc aca aac tta gga ttc gag          1152
Glu Gly Arg Arg Ala Trp Glu Thr Tyr Ala Thr Asn Leu Gly Phe Glu
370                 375                 380 ggc cac aac tgg tct aaa ggt ccg tcc agg gcc gag ctg ttc cag cac          1200
Gly His Asn Trp Ser Lys Gly Pro Ser Arg Ala Glu Leu Phe Gln His
385                 390                 395                 400 ttg gat gag gac cgt gac aag gga ttt tgc ctg gta gac aat gaa att          1248
Leu Asp Glu Asp Arg Asp Lys Gly Phe Cys Leu Val Asp Asn Glu Ile
                405                 410                 415 act ccc gga atc gct gct gtg gga gca ccc att tac aac cac cgt ggt          1296
Thr Pro Gly Ile Ala Ala Val Gly Ala Pro Ile Tyr Asn His Arg Gly
                420                 425                 430 gaa gtc gtg gca agc ctg tcc atg agt gga ctg cgg gac ggc atc ctc          1344
Glu Val Val Ala Ser Leu Ser Met Ser Gly Leu Arg Asp Gly Ile Leu
                435                 440                 445 agc gat acc acc gac tac tcg gcc gtg gaa ctg atc ctg cag ggg tct          1392
Ser Asp Thr Thr Asp Tyr Ser Ala Val Glu Leu Ile Leu Gln Gly Ser
        450                 455                 460 gcg gag att tcc caa gcg ctg gga gcg gcc att gag cac aac ggg ggc          1440
Ala Glu Ile Ser Gln Ala Leu Gly Ala Ala Ile Glu His Asn Gly Gly
```

```
                465                 470                 475                 480
aac caa aaa cta ccc cag gta acc cct ctg agc att gtg gtt taa              1485
Asn Gln Lys Leu Pro Gln Val Thr Pro Leu Ser Ile Val Val
                        485                 490
```

<210> SEQ ID NO 14
<211> LENGTH: 494
<212> TYPE: PRT
<213> ORGANISM: Corynebacterium glutamicum

<400> SEQUENCE: 14

```
Met Gln Thr Ile Gln Leu Leu Thr Lys Ala Gly Leu Val Asp Ala
1               5                   10                  15

Leu Ser Ala Gly Pro Asn Thr His Ser Glu Leu Ala Lys Gln Leu Asn
                20                  25                  30

Glu Pro Arg Ser Ser Ile Tyr Arg Ile Thr Ser Ser Leu Glu Glu Val
                35                  40                  45

Gly Tyr Val Asn Ile Thr Ser Ser Gly Leu Leu Gly Leu Gly Val Asn
            50                  55                  60

Ile Leu His Leu Gly Glu Ser Ala Val Asp Ala Leu Leu Asn Arg Thr
65              70                  75                  80

Leu Leu Arg Glu Lys Leu Gly Trp Leu Arg Asp Gln Leu Gly Met Thr
                85                  90                  95

Ala Phe Phe Cys Thr Leu Gln Asp Asp Arg Ile Ile Ser Leu Asp Trp
                100                 105                 110

Gln Glu Gly Ala Asp Ile Asp Leu Ile Tyr Leu Ala Pro Gly Arg Thr
                115                 120                 125

Leu Pro Ser Gln Lys Gly Ala Val Ser His Val Leu Gln Gly Lys Asp
            130                 135                 140

Leu Arg Lys Gly Trp Ser Ile Asp His Gly Leu Thr Val Gly Val
145                 150                 155                 160

Ser Ser Leu Ala Val Ala Val Lys Asn Ala Asn Gly Asp Val Leu Gly
                165                 170                 175

Ala Val Ala Val Ala Gly Leu Ser Ala Ser Val Glu Ser Lys Ile Asp
                180                 185                 190

Thr Ile Arg Asp Thr Leu Lys Glu Thr Ala Cys Ala Ile Ala Asn Met
                195                 200                 205

Pro Pro Ala Lys Thr Gln Glu Phe Asp Pro Ser Arg Ile Lys Glu Pro
            210                 215                 220

Asn Ser Pro Ser Val Ile Thr Lys Ala Ala Thr Leu Met Asp Val Leu
225                 230                 235                 240

Arg Thr Glu Gly Pro Thr Asn Ser Ala Arg Leu Ala Glu Val Leu Gly
                245                 250                 255

Glu Pro Ile Ser Ser Val Tyr Arg Met Leu His Thr Leu Thr Ala Ile
                260                 265                 270

Gly Trp Val Glu Gln Asp Gly Lys Arg Gly Ser Tyr Arg Val Gly Leu
            275                 280                 285

Ala Met Leu Thr Leu Ala Glu Ser Gln Leu Arg His Met Asp Leu Arg
    290                 295                 300

Lys Ile Ala Ala Leu Thr Met Arg Lys Ile His Ala Leu Thr Gly Glu
305                 310                 315                 320

Thr Thr Phe Leu Cys Val Arg His Gly Ile Arg Ala Val Cys Ile Glu
                325                 330                 335

Arg Val Asp Gly Asp Arg Val Asn Ser Arg Val Leu Gln Leu Gly Thr
                340                 345                 350
```

-continued

```
Ser Leu Pro Leu His Val Gly Ala Ala Pro Arg Ala Leu Leu Ala Phe
        355                 360                 365

Glu Gly Arg Arg Ala Trp Glu Thr Tyr Ala Thr Asn Leu Gly Phe Glu
    370                 375                 380

Gly His Asn Trp Ser Lys Gly Pro Ser Arg Ala Glu Leu Phe Gln His
385                 390                 395                 400

Leu Asp Glu Asp Arg Asp Lys Gly Phe Cys Leu Val Asp Asn Glu Ile
                405                 410                 415

Thr Pro Gly Ile Ala Ala Val Gly Ala Pro Ile Tyr Asn His Arg Gly
                420                 425                 430

Glu Val Val Ala Ser Leu Ser Met Ser Gly Leu Arg Asp Gly Ile Leu
            435                 440                 445

Ser Asp Thr Thr Asp Tyr Ser Ala Val Glu Leu Ile Leu Gln Gly Ser
        450                 455                 460

Ala Glu Ile Ser Gln Ala Leu Gly Ala Ala Ile Glu His Asn Gly Gly
465                 470                 475                 480

Asn Gln Lys Leu Pro Gln Val Thr Pro Leu Ser Ile Val Val
                485                 490
```

```
<210> SEQ ID NO 15
<211> LENGTH: 798
<212> TYPE: DNA
<213> ORGANISM: Sphingomonas elodea
<220> FEATURE:
<221> NAME/KEY: CDS
<222> LOCATION: (1)..(798)

<400> SEQUENCE: 15
```

```
atg tcg caa gcc gat ctc cag cag ggg ccg att ccg gcc gcc cag cgc      48
Met Ser Gln Ala Asp Leu Gln Gln Gly Pro Ile Pro Ala Ala Gln Arg
1               5                   10                  15 gcc gtc tat ccg agc ctg aag ggc aag cgg gtc ctg ata acc ggc ggt      96
Ala Val Tyr Pro Ser Leu Lys Gly Lys Arg Val Leu Ile Thr Gly Gly
                20                  25                  30 ggt tcg ggc atc ggc gcc ggg ttg gtc gaa ggc ttc gtc cgc cag ggc     144
Gly Ser Gly Ile Gly Ala Gly Leu Val Glu Gly Phe Val Arg Gln Gly
            35                  40                  45 gcg gac gtg acc ttc ttc gac atc gcc gag gcg gat tcg cag gcg ctg     192
Ala Asp Val Thr Phe Phe Asp Ile Ala Glu Ala Asp Ser Gln Ala Leu
        50                  55                  60 gtc gcc agc ctg acc gac gcg gcg atc gcg ccg cgc ttc tat cgt gtc     240
Val Ala Ser Leu Thr Asp Ala Ala Ile Ala Pro Arg Phe Tyr Arg Val
65                  70                  75                  80 gat ctc acc gac att ccc gcc gcg cag gcg cag gtg cag gcg ctg atc     288
Asp Leu Thr Asp Ile Pro Ala Ala Gln Ala Gln Val Gln Ala Leu Ile
                85                  90                  95 gag gcc gag ggc ggc ttc gac gtg ctg ctg aac aac gcc gcc aat gac     336
Glu Ala Glu Gly Gly Phe Asp Val Leu Leu Asn Asn Ala Ala Asn Asp
                100                 105                 110 gat cgc cac acg atc gag cag gtg acc ccg gaa tat tgg gac aac cgc     384
Asp Arg His Thr Ile Glu Gln Val Thr Pro Glu Tyr Trp Asp Asn Arg
            115                 120                 125 ctc aac gtg aac ctg cgc cac cag ttc ttc ctg gcg cag gcg gtg att     432
Leu Asn Val Asn Leu Arg His Gln Phe Phe Leu Ala Gln Ala Val Ile
        130                 135                 140 ccg gcg atg aag gcc aag cgc gcc ggc gtg atc atc aac ctc ggc tcg     480
Pro Ala Met Lys Ala Lys Arg Ala Gly Val Ile Ile Asn Leu Gly Ser
145                 150                 155                 160
```

```
atc tcg tgg cac ctc gcc ctg gag gag ctg acg ctc tac cag acc gcc    528
Ile Ser Trp His Leu Ala Leu Glu Glu Leu Thr Leu Tyr Gln Thr Ala
            165                 170                 175 aag gcg gcg atc gag ggc ctg acc cgc agc ctg gcg cgc gag ctg ggc    576
Lys Ala Ala Ile Glu Gly Leu Thr Arg Ser Leu Ala Arg Glu Leu Gly
        180                 185                 190 ccg gac ggc atc cgc tcg gtc tgc atc gtc ccc ggc aac gtc aag acg    624
Pro Asp Gly Ile Arg Ser Val Cys Ile Val Pro Gly Asn Val Lys Thr
    195                 200                 205 ccg cgc cag atg aag tgg tac acg ccc gag ggc gag gcc gag atc gtc    672
Pro Arg Gln Met Lys Trp Tyr Thr Pro Glu Gly Glu Ala Glu Ile Val
210                 215                 220 aag gcg cag tgc ctg ccc ggc cgc ctg gtg ccg gac gac atc gcc gcg    720
Lys Ala Gln Cys Leu Pro Gly Arg Leu Val Pro Asp Asp Ile Ala Ala
225                 230                 235                 240 ctg gcg ctg ttc ctt gca tcc gac gat gcc cgg ctg ata acg agc cac    768
Leu Ala Leu Phe Leu Ala Ser Asp Asp Ala Arg Leu Ile Thr Ser His
                245                 250                 255 gaa ttc ttc gtg gat gca ggc tgg aga taa                            798
Glu Phe Phe Val Asp Ala Gly Trp Arg
            260                 265

<210> SEQ ID NO 16
<211> LENGTH: 265
<212> TYPE: PRT
<213> ORGANISM: Sphingomonas elodea

<400> SEQUENCE: 16

Met Ser Gln Ala Asp Leu Gln Gln Gly Pro Ile Pro Ala Ala Gln Arg
1               5                   10                  15

Ala Val Tyr Pro Ser Leu Lys Gly Lys Arg Val Leu Ile Thr Gly Gly
            20                  25                  30

Gly Ser Gly Ile Gly Ala Gly Leu Val Glu Gly Phe Val Arg Gln Gly
        35                  40                  45

Ala Asp Val Thr Phe Phe Asp Ile Ala Glu Ala Asp Ser Gln Ala Leu
    50                  55                  60

Val Ala Ser Leu Thr Asp Ala Ala Ile Ala Pro Arg Phe Tyr Arg Val
65                  70                  75                  80

Asp Leu Thr Asp Ile Pro Ala Ala Gln Ala Gln Val Gln Ala Leu Ile
                85                  90                  95

Glu Ala Glu Gly Gly Phe Asp Val Leu Leu Asn Ala Ala Asn Asp
            100                 105                 110

Asp Arg His Thr Ile Glu Gln Val Thr Pro Glu Tyr Trp Asp Asn Arg
        115                 120                 125

Leu Asn Val Asn Leu Arg His Gln Phe Phe Leu Ala Gln Ala Val Ile
    130                 135                 140

Pro Ala Met Lys Ala Lys Arg Ala Gly Val Ile Ile Asn Leu Gly Ser
145                 150                 155                 160

Ile Ser Trp His Leu Ala Leu Glu Glu Leu Thr Leu Tyr Gln Thr Ala
                165                 170                 175

Lys Ala Ala Ile Glu Gly Leu Thr Arg Ser Leu Ala Arg Glu Leu Gly
            180                 185                 190

Pro Asp Gly Ile Arg Ser Val Cys Ile Val Pro Gly Asn Val Lys Thr
        195                 200                 205

Pro Arg Gln Met Lys Trp Tyr Thr Pro Glu Gly Glu Ala Glu Ile Val
    210                 215                 220

Lys Ala Gln Cys Leu Pro Gly Arg Leu Val Pro Asp Asp Ile Ala Ala
```

```
                        225                 230                 235                 240
Leu Ala Leu Phe Leu Ala Ser Asp Asp Ala Arg Leu Ile Thr Ser His
                        245                 250                 255

Glu Phe Phe Val Asp Ala Gly Trp Arg
                260                 265

<210> SEQ ID NO 17
<211> LENGTH: 894
<212> TYPE: DNA
<213> ORGANISM: Sphingomonas elodea
<220> FEATURE:
<221> NAME/KEY: CDS
<222> LOCATION: (1)..(894)

<400> SEQUENCE: 17 atg acc gac aag gtg gtg gtt tcg gcg ccg gag agc gtg tgg ggg ctc    48
Met Thr Asp Lys Val Val Val Ser Ala Pro Glu Ser Val Trp Gly Leu
1               5                   10                  15 agc gcc ccg ctt ctc gaa ggc ccg gta tgg gtg gag cgc gat gcc gcg    96
Ser Ala Pro Leu Leu Glu Gly Pro Val Trp Val Glu Arg Asp Ala Ala
            20                  25                  30 ctt tgg ttc gtc gac atc aag agc cac aag atc cac cgc tat gat ccc    144
Leu Trp Phe Val Asp Ile Lys Ser His Lys Ile His Arg Tyr Asp Pro
        35                  40                  45 gcc acc ggc gac aag gcg agc tgg gac gcg ccg gcg cag gtg ggc ttc    192
Ala Thr Gly Asp Lys Ala Ser Trp Asp Ala Pro Ala Gln Val Gly Phe
    50                  55                  60 gcg ctg ccg gcg gcg agc ggc ggc ttc gtc gcg ggg ctg cag acc ggg    240
Ala Leu Pro Ala Ala Ser Gly Gly Phe Val Ala Gly Leu Gln Thr Gly
65                  70                  75                  80 ctc gcc agg ttc gat ccg acg gac ggc agc ttc gtg ccc ctg gtc gat    288
Leu Ala Arg Phe Asp Pro Thr Asp Gly Ser Phe Val Pro Leu Val Asp
                85                  90                  95 ccc gaa ccc gaa ctg ccc ggc aac cgg ctg aac gac ggc acc gtc gat    336
Pro Glu Pro Glu Leu Pro Gly Asn Arg Leu Asn Asp Gly Thr Val Asp
            100                 105                 110 tcg gaa ggc cgc ctg tgg ttc ggc acg atg gac gac ggc gag agc gcg    384
Ser Glu Gly Arg Leu Trp Phe Gly Thr Met Asp Asp Gly Glu Ser Ala
        115                 120                 125 gcc acc ggc acc atc tat cgc ctg gca gcg gac ggc agc tgc gtg ccc    432
Ala Thr Gly Thr Ile Tyr Arg Leu Ala Ala Asp Gly Ser Cys Val Pro
    130                 135                 140 tcc agc ccc aag gta tcg atc acc aac ggc ccg gcg gtc tcg ccc gac    480
Ser Ser Pro Lys Val Ser Ile Thr Asn Gly Pro Ala Val Ser Pro Asp
145                 150                 155                 160 ggc aag acg ctc tac cat gtc gat acg ctc ggc gcg gtg gtc tat gcc    528
Gly Lys Thr Leu Tyr His Val Asp Thr Leu Gly Ala Val Val Tyr Ala
                165                 170                 175 tgc gac atc gat ccg gac ggc gcg ctg gtg aac cgc cgc gag ttc gtg    576
Cys Asp Ile Asp Pro Asp Gly Ala Leu Val Asn Arg Arg Glu Phe Val
            180                 185                 190 cgc atc gcc gag ggc gaa ggc ttc ccg gac ggc ccg tgc gtc gac agc    624
Arg Ile Ala Glu Gly Glu Gly Phe Pro Asp Gly Pro Cys Val Asp Ser
        195                 200                 205 gag ggc tat gtg tgg gtg agc ctg tac gtc ggc tcg gag gtg cgt cgc    672
Glu Gly Tyr Val Trp Val Ser Leu Tyr Val Gly Ser Glu Val Arg Arg
    210                 215                 220 tac tcg cct gcg ggc gag ctg gtc gag acg gtg ccc ttc ccc gtc gat    720
Tyr Ser Pro Ala Gly Glu Leu Val Glu Thr Val Pro Phe Pro Val Asp
225                 230                 235                 240
```

```
gcg atc acc aag atc gcg ttc ggc ggc ccg gac ctg aag acg gtc ttc    768
Ala Ile Thr Lys Ile Ala Phe Gly Gly Pro Asp Leu Lys Thr Val Phe
            245                 250                 255 gcc acc acc gcg aac aag cac ctt tcg gcc gaa gac aag gcc gca cgg    816
Ala Thr Thr Ala Asn Lys His Leu Ser Ala Glu Asp Lys Ala Ala Arg
        260                 265                 270 ccg agt tcg ggc gac ctg ttc cgc ttc cgc gtg acg gtg gcc ggt cag    864
Pro Ser Ser Gly Asp Leu Phe Arg Phe Arg Val Thr Val Ala Gly Gln
    275                 280                 285 ccg acc gcg atg atc cgc atc ggg gcc tga                            894
Pro Thr Ala Met Ile Arg Ile Gly Ala
290                 295

<210> SEQ ID NO 18
<211> LENGTH: 297
<212> TYPE: PRT
<213> ORGANISM: Sphingomonas elodea

<400> SEQUENCE: 18

Met Thr Asp Lys Val Val Ser Ala Pro Glu Ser Val Trp Gly Leu
1               5                   10                  15

Ser Ala Pro Leu Leu Glu Gly Pro Val Trp Val Glu Arg Asp Ala Ala
                20                  25                  30

Leu Trp Phe Val Asp Ile Lys Ser His Lys Ile His Arg Tyr Asp Pro
            35                  40                  45

Ala Thr Gly Asp Lys Ala Ser Trp Asp Ala Pro Ala Gln Val Gly Phe
        50                  55                  60

Ala Leu Pro Ala Ala Ser Gly Gly Phe Val Ala Gly Leu Gln Thr Gly
65                  70                  75                  80

Leu Ala Arg Phe Asp Pro Thr Asp Gly Ser Phe Val Pro Leu Val Asp
                85                  90                  95

Pro Glu Pro Glu Leu Pro Gly Asn Arg Leu Asn Asp Gly Thr Val Asp
            100                 105                 110

Ser Glu Gly Arg Leu Trp Phe Gly Thr Met Asp Asp Gly Glu Ser Ala
        115                 120                 125

Ala Thr Gly Thr Ile Tyr Arg Leu Ala Ala Asp Gly Ser Cys Val Pro
    130                 135                 140

Ser Ser Pro Lys Val Ser Ile Thr Asn Gly Pro Ala Val Ser Pro Asp
145                 150                 155                 160

Gly Lys Thr Leu Tyr His Val Asp Thr Leu Gly Ala Val Val Tyr Ala
                165                 170                 175

Cys Asp Ile Asp Pro Asp Gly Ala Leu Val Asn Arg Arg Glu Phe Val
            180                 185                 190

Arg Ile Ala Glu Gly Glu Gly Phe Pro Asp Gly Pro Cys Val Asp Ser
        195                 200                 205

Glu Gly Tyr Val Trp Val Ser Leu Tyr Val Gly Ser Glu Val Arg Arg
    210                 215                 220

Tyr Ser Pro Ala Gly Glu Leu Val Glu Thr Val Pro Phe Pro Val Asp
225                 230                 235                 240

Ala Ile Thr Lys Ile Ala Phe Gly Gly Pro Asp Leu Lys Thr Val Phe
                245                 250                 255

Ala Thr Thr Ala Asn Lys His Leu Ser Ala Glu Asp Lys Ala Ala Arg
            260                 265                 270

Pro Ser Ser Gly Asp Leu Phe Arg Phe Arg Val Thr Val Ala Gly Gln
        275                 280                 285

Pro Thr Ala Met Ile Arg Ile Gly Ala
```

<210> SEQ ID NO 19
<211> LENGTH: 1968
<212> TYPE: DNA
<213> ORGANISM: Escherichia coli
<220> FEATURE:
<221> NAME/KEY: CDS
<222> LOCATION: (1)..(1968)

<400> SEQUENCE: 19

| | | | | | | | | | | | | | | | | |
|---|---|---|---|---|---|---|---|---|---|---|---|---|---|---|---|---|
| atg | acc | att | gag | aaa | att | ttc | acc | ccg | cag | gac | gac | gcg | ttt | tat | gcg | 48 |
| Met | Thr | Ile | Glu | Lys | Ile | Phe | Thr | Pro | Gln | Asp | Asp | Ala | Phe | Tyr | Ala | |
| 1 | | | | 5 | | | | | 10 | | | | | 15 | | |
| gtg | atc | acc | cac | gcg | gcg | ggg | ccg | cag | ggc | gct | ctg | ccg | ctg | acc | ccg | 96 |
| Val | Ile | Thr | His | Ala | Ala | Gly | Pro | Gln | Gly | Ala | Leu | Pro | Leu | Thr | Pro | |
| | | | 20 | | | | | 25 | | | | | 30 | | | |
| cag | atg | ctg | atg | gaa | tct | ccc | agc | ggc | aac | ctg | ttc | ggc | atg | acg | cag | 144 |
| Gln | Met | Leu | Met | Glu | Ser | Pro | Ser | Gly | Asn | Leu | Phe | Gly | Met | Thr | Gln | |
| | 35 | | | | | 40 | | | | | 45 | | | | | |
| aac | gcc | ggg | atg | ggc | tgg | gac | gcc | aac | aag | ctc | acc | ggc | aaa | gag | gtg | 192 |
| Asn | Ala | Gly | Met | Gly | Trp | Asp | Ala | Asn | Lys | Leu | Thr | Gly | Lys | Glu | Val | |
| 50 | | | | | 55 | | | | | 60 | | | | | | |
| ctg | att | atc | ggc | act | cag | ggc | ggc | atc | cgc | gcc | gga | gac | gga | cgc | cca | 240 |
| Leu | Ile | Ile | Gly | Thr | Gln | Gly | Gly | Ile | Arg | Ala | Gly | Asp | Gly | Arg | Pro | |
| 65 | | | | | 70 | | | | | 75 | | | | | 80 | |
| atc | gcg | ctg | ggc | tac | cac | acc | ggg | cat | tgg | gag | atc | ggc | atg | cag | atg | 288 |
| Ile | Ala | Leu | Gly | Tyr | His | Thr | Gly | His | Trp | Glu | Ile | Gly | Met | Gln | Met | |
| | | | | 85 | | | | | 90 | | | | | 95 | | |
| cag | gcg | gcg | gcg | aag | gag | atc | acc | cgc | aat | ggc | ggg | atc | ccg | ttc | gcg | 336 |
| Gln | Ala | Ala | Ala | Lys | Glu | Ile | Thr | Arg | Asn | Gly | Gly | Ile | Pro | Phe | Ala | |
| | | | 100 | | | | | 105 | | | | | 110 | | | |
| gcc | ttc | gtc | agc | gat | ccg | tgc | gac | ggg | cgc | tcg | cag | ggc | acg | cac | ggt | 384 |
| Ala | Phe | Val | Ser | Asp | Pro | Cys | Asp | Gly | Arg | Ser | Gln | Gly | Thr | His | Gly | |
| | | 115 | | | | | 120 | | | | | 125 | | | | |
| atg | ttc | gat | tcc | ctg | ccg | tac | cgc | aac | gac | gcg | gcg | atc | gtg | ttt | cgc | 432 |
| Met | Phe | Asp | Ser | Leu | Pro | Tyr | Arg | Asn | Asp | Ala | Ala | Ile | Val | Phe | Arg | |
| 130 | | | | | 135 | | | | | 140 | | | | | | |
| cgc | ctg | atc | cgc | tcc | ctg | ccg | acg | cgg | cgg | gcg | gtg | atc | ggc | gta | gcg | 480 |
| Arg | Leu | Ile | Arg | Ser | Leu | Pro | Thr | Arg | Arg | Ala | Val | Ile | Gly | Val | Ala | |
| 145 | | | | | 150 | | | | | 155 | | | | | 160 | |
| acc | tgc | gat | aaa | ggg | ctg | ccc | gcc | acc | atg | att | gcg | ctg | gcc | gcg | atg | 528 |
| Thr | Cys | Asp | Lys | Gly | Leu | Pro | Ala | Thr | Met | Ile | Ala | Leu | Ala | Ala | Met | |
| | | | | 165 | | | | | 170 | | | | | 175 | | |
| cac | gac | ctg | ccg | act | att | ctg | gtg | ccg | ggc | ggg | gcg | acg | ctg | ccg | ccg | 576 |
| His | Asp | Leu | Pro | Thr | Ile | Leu | Val | Pro | Gly | Gly | Ala | Thr | Leu | Pro | Pro | |
| | | | 180 | | | | | 185 | | | | | 190 | | | |
| acc | gtc | ggg | gaa | gac | gcg | ggc | aag | gtg | cag | acc | atc | ggc | gcg | cgt | ttc | 624 |
| Thr | Val | Gly | Glu | Asp | Ala | Gly | Lys | Val | Gln | Thr | Ile | Gly | Ala | Arg | Phe | |
| | 195 | | | | | 200 | | | | | 205 | | | | | |
| gcc | aac | cac | gaa | ctc | tcc | ctg | cag | gag | gcc | gcc | gaa | ctg | ggc | tgt | cgc | 672 |
| Ala | Asn | His | Glu | Leu | Ser | Leu | Gln | Glu | Ala | Ala | Glu | Leu | Gly | Cys | Arg | |
| 210 | | | | | 215 | | | | | 220 | | | | | | |
| gcc | tgc | gcc | tcg | ccg | ggc | ggc | ggg | tgt | cag | ttc | ctc | ggc | acg | gcg | ggc | 720 |
| Ala | Cys | Ala | Ser | Pro | Gly | Gly | Gly | Cys | Gln | Phe | Leu | Gly | Thr | Ala | Gly | |
| 225 | | | | | 230 | | | | | 235 | | | | | 240 | |
| acc | tcg | cag | gtg | gtc | gcg | gag | gcg | ctg | ggt | ctg | gcg | ctg | ccg | cac | tcc | 768 |
| Thr | Ser | Gln | Val | Val | Ala | Glu | Ala | Leu | Gly | Leu | Ala | Leu | Pro | His | Ser | |
| | | | | 245 | | | | | 250 | | | | | 255 | | |
| gcg | ctg | gcg | ccg | tcc | ggg | cag | gcg | gtg | tgg | ctg | gag | atc | gcc | cgc | cag | 816 |
| Ala | Leu | Ala | Pro | Ser | Gly | Gln | Ala | Val | Trp | Leu | Glu | Ile | Ala | Arg | Gln | |

-continued

```
                260                 265                 270
tcg gcg cgc gcg gtc agc gag ctg gat agc cgc ggc atc acc acg cgg         864
Ser Ala Arg Ala Val Ser Glu Leu Asp Ser Arg Gly Ile Thr Thr Arg
            275                 280                 285 gat atc ctc tcc gat aaa gcc atc gaa aac gcg atg gtg atc cac gcg         912
Asp Ile Leu Ser Asp Lys Ala Ile Glu Asn Ala Met Val Ile His Ala
    290                 295                 300 gcg ttc ggc ggc tcc acc aat tta ctg ctg cac att ccg gcc atc gcc         960
Ala Phe Gly Gly Ser Thr Asn Leu Leu Leu His Ile Pro Ala Ile Ala
305                 310                 315                 320 cac gcg gcg ggc tgc acg atc ccg gac gtt gag cac tgg acg cgc atc        1008
His Ala Ala Gly Cys Thr Ile Pro Asp Val Glu His Trp Thr Arg Ile
                325                 330                 335 aac cgt aaa gtg ccg cgt ctg gtg agc gtg ctg ccc aac ggc ccg gac        1056
Asn Arg Lys Val Pro Arg Leu Val Ser Val Leu Pro Asn Gly Pro Asp
        340                 345                 350 tat cac ccg acc gtg cgc gcc ttc ctc gcg ggc ggc gtg ccg gag gtg        1104
Tyr His Pro Thr Val Arg Ala Phe Leu Ala Gly Gly Val Pro Glu Val
                355                 360                 365 atg ctc cac ctg cgc gac ctc ggc ctg ctg cat ctg gac gcc atg acc        1152
Met Leu His Leu Arg Asp Leu Gly Leu Leu His Leu Asp Ala Met Thr
    370                 375                 380 gtg acc ggc cag acg gtg ggc gag aac ctt gaa tgg tgg cag gcg tcc        1200
Val Thr Gly Gln Thr Val Gly Glu Asn Leu Glu Trp Trp Gln Ala Ser
385                 390                 395                 400 gag cgc cgg gcg cgc ttc cgc cag tgc ctg cgc gag cag gac ggc gta        1248
Glu Arg Arg Ala Arg Phe Arg Gln Cys Leu Arg Glu Gln Asp Gly Val
                405                 410                 415 gag ccg gat gac gtg atc ctg ccg ccg gag aag gca aaa gcg aaa ggg        1296
Glu Pro Asp Asp Val Ile Leu Pro Pro Glu Lys Ala Lys Ala Lys Gly
        420                 425                 430 ctg acc tcg acg gtc tgc ttc ccg acg ggc aac atc gct ccg gaa ggt        1344
Leu Thr Ser Thr Val Cys Phe Pro Thr Gly Asn Ile Ala Pro Glu Gly
                435                 440                 445 tcg gtg atc aag gcc acg gcg atc gac ccg tcg gtg gtg ggc gaa gat        1392
Ser Val Ile Lys Ala Thr Ala Ile Asp Pro Ser Val Val Gly Glu Asp
    450                 455                 460 ggc gta tac cac cac acc ggc cgg gtg cgg gtg ttt gtc tcg gaa gcg        1440
Gly Val Tyr His His Thr Gly Arg Val Arg Val Phe Val Ser Glu Ala
465                 470                 475                 480 cag gcg atc aag gcg atc aag cgg gaa gag att gtg cag ggc gat atc        1488
Gln Ala Ile Lys Ala Ile Lys Arg Glu Glu Ile Val Gln Gly Asp Ile
                485                 490                 495 atg gtg gtg atc ggc ggc ggg ccg tcc ggc acc ggc atg gaa gag acc        1536
Met Val Val Ile Gly Gly Gly Pro Ser Gly Thr Gly Met Glu Glu Thr
        500                 505                 510 tac cag ctc acc tcc gcg cta aag cat atc tcg tgg ggc aag acg gtg        1584
Tyr Gln Leu Thr Ser Ala Leu Lys His Ile Ser Trp Gly Lys Thr Val
                515                 520                 525 tcg ctc atc acc gat gcg cgc ttc tcg ggc gtg tcg acg ggc gcc tgc        1632
Ser Leu Ile Thr Asp Ala Arg Phe Ser Gly Val Ser Thr Gly Ala Cys
    530                 535                 540 ttc ggc cac gtg tcg ccg gag gcg ctg gcg ggc ggg ccg att ggc aag        1680
Phe Gly His Val Ser Pro Glu Ala Leu Ala Gly Gly Pro Ile Gly Lys
545                 550                 555                 560 ctg cgc gat aac gac atc atc gag att gcc gtg gat cgt ctg acg tta        1728
Leu Arg Asp Asn Asp Ile Ile Glu Ile Ala Val Asp Arg Leu Thr Leu
                565                 570                 575 act ggc agc gtg aac ttc atc ggc acc gcg gac aac ccg ctg acg ccg        1776
```

```
Thr Gly Ser Val Asn Phe Ile Gly Thr Ala Asp Asn Pro Leu Thr Pro
            580                 585                 590 gaa gag ggc gcg cgc gag ctg gcg cgg cgg cag acg cac ccg gac ctg      1824
Glu Glu Gly Ala Arg Glu Leu Ala Arg Arg Gln Thr His Pro Asp Leu
        595                 600                 605 cac gcc cac gac ttt ttg ccg gac gac acc cgg ctg tgg gcg gca ctg      1872
His Ala His Asp Phe Leu Pro Asp Asp Thr Arg Leu Trp Ala Ala Leu
610                 615                 620 cag tcg gtg agc ggc ggc acc tgg aaa ggc tgt att tat gac acc gat      1920
Gln Ser Val Ser Gly Gly Thr Trp Lys Gly Cys Ile Tyr Asp Thr Asp
625                 630                 635                 640 aaa att atc gag gta att aac gcc ggt aaa aaa gcg ctc gga att taa      1968
Lys Ile Ile Glu Val Ile Asn Ala Gly Lys Lys Ala Leu Gly Ile
                645                 650                 655

<210> SEQ ID NO 20
<211> LENGTH: 655
<212> TYPE: PRT
<213> ORGANISM: Escherichia coli

<400> SEQUENCE: 20

Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
                20                  25                  30

Gln Met Leu Met Glu Ser Pro Ser Gly Asn Leu Phe Gly Met Thr Gln
            35                  40                  45

Asn Ala Gly Met Gly Trp Asp Ala Asn Lys Leu Thr Gly Lys Glu Val
        50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220

Ala Cys Ala Ser Pro Gly Gly Gly Cys Gln Phe Leu Gly Thr Ala Gly
225                 230                 235                 240

Thr Ser Gln Val Val Ala Glu Ala Leu Gly Leu Ala Leu Pro His Ser
                245                 250                 255

Ala Leu Ala Pro Ser Gly Gln Ala Val Trp Leu Glu Ile Ala Arg Gln
            260                 265                 270

Ser Ala Arg Ala Val Ser Glu Leu Asp Ser Arg Gly Ile Thr Thr Arg
```

```
                275                 280                 285
Asp Ile Leu Ser Asp Lys Ala Ile Glu Asn Ala Met Val Ile His Ala
            290                 295                 300
Ala Phe Gly Gly Ser Thr Asn Leu Leu His Ile Pro Ala Ile Ala
305                 310                 315                 320
His Ala Ala Gly Cys Thr Ile Pro Asp Val Glu His Trp Thr Arg Ile
                325                 330                 335
Asn Arg Lys Val Pro Arg Leu Val Ser Val Leu Pro Asn Gly Pro Asp
            340                 345                 350
Tyr His Pro Thr Val Arg Ala Phe Leu Ala Gly Gly Val Pro Glu Val
                355                 360                 365
Met Leu His Leu Arg Asp Leu Gly Leu Leu His Leu Asp Ala Met Thr
            370                 375                 380
Val Thr Gly Gln Thr Val Gly Glu Asn Leu Glu Trp Trp Gln Ala Ser
385                 390                 395                 400
Glu Arg Arg Ala Arg Phe Arg Gln Cys Leu Arg Glu Gln Asp Gly Val
                405                 410                 415
Glu Pro Asp Asp Val Ile Leu Pro Pro Glu Lys Ala Lys Ala Lys Gly
            420                 425                 430
Leu Thr Ser Thr Val Cys Phe Pro Thr Gly Asn Ile Ala Pro Glu Gly
                435                 440                 445
Ser Val Ile Lys Ala Thr Ala Ile Asp Pro Ser Val Val Gly Glu Asp
            450                 455                 460
Gly Val Tyr His His Thr Gly Arg Val Arg Val Phe Val Ser Glu Ala
465                 470                 475                 480
Gln Ala Ile Lys Ala Ile Lys Arg Glu Glu Ile Val Gln Gly Asp Ile
                485                 490                 495
Met Val Val Ile Gly Gly Pro Ser Gly Thr Gly Met Glu Glu Thr
            500                 505                 510
Tyr Gln Leu Thr Ser Ala Leu Lys His Ile Ser Trp Gly Lys Thr Val
                515                 520                 525
Ser Leu Ile Thr Asp Ala Arg Phe Ser Gly Val Ser Thr Gly Ala Cys
            530                 535                 540
Phe Gly His Val Ser Pro Glu Ala Leu Ala Gly Gly Pro Ile Gly Lys
545                 550                 555                 560
Leu Arg Asp Asn Asp Ile Ile Glu Ile Ala Val Asp Arg Leu Thr Leu
                565                 570                 575
Thr Gly Ser Val Asn Phe Ile Gly Thr Ala Asp Asn Pro Leu Thr Pro
            580                 585                 590
Glu Glu Gly Ala Arg Glu Leu Ala Arg Arg Gln Thr His Pro Asp Leu
                595                 600                 605
His Ala His Asp Phe Leu Pro Asp Asp Thr Arg Leu Trp Ala Ala Leu
            610                 615                 620
Gln Ser Val Ser Gly Gly Thr Trp Lys Gly Cys Ile Tyr Asp Thr Asp
625                 630                 635                 640
Lys Ile Ile Glu Val Ile Asn Ala Gly Lys Lys Ala Leu Gly Ile
                645                 650                 655

<210> SEQ ID NO 21
<211> LENGTH: 1113
<212> TYPE: DNA
<213> ORGANISM: Sphingomonas elodea
<220> FEATURE:
<221> NAME/KEY: CDS
<222> LOCATION: (1)..(1113)
```

```
<400> SEQUENCE: 21 atg ctg cct gcc gat cat gcg cag gcg att ctg gtc ggc cgt gtg cag    48
Met Leu Pro Ala Asp His Ala Gln Ala Ile Leu Val Gly Arg Val Gln
1               5                   10                  15 acc ccg gcg ggc ccg agc ccc gtt ctc ctc cgc gat ggc cag gtg atc    96
Thr Pro Ala Gly Pro Ser Pro Val Leu Leu Arg Asp Gly Gln Val Ile
            20                  25                  30 gac gtt tcg gcg atc gcg ccg acc gtc gcc gac ctg ctg gaa cgc gac   144
Asp Val Ser Ala Ile Ala Pro Thr Val Ala Asp Leu Leu Glu Arg Asp
        35                  40                  45 gac atc gcg acg ctg agc ggc acg gtg ctg tgc agc gtc gac gcg ctc   192
Asp Ile Ala Thr Leu Ser Gly Thr Val Leu Cys Ser Val Asp Ala Leu
    50                  55                  60 ggc acc gag tcg gcg ccg cag gtg ctg gct ccg gtc gac ctg cag tgc   240
Gly Thr Glu Ser Ala Pro Gln Val Leu Ala Pro Val Asp Leu Gln Cys
65                  70                  75                  80 gtg aag gcc gcc ggc gtc acc ttc gcc gtc tcg gcg ctg gag cgc gtg   288
Val Lys Ala Ala Gly Val Thr Phe Ala Val Ser Ala Leu Glu Arg Val
                85                  90                  95 atc gag gaa cgc gcc cgc ggc gat tcc gcc aag gcc gcc gag att cgc   336
Ile Glu Glu Arg Ala Arg Gly Asp Ser Ala Lys Ala Ala Glu Ile Arg
            100                 105                 110 ggc gac ctc gaa gcc aag gtg ggt tcg ggc atc cgc tcg gtc gtc ccc   384
Gly Asp Leu Glu Ala Lys Val Gly Ser Gly Ile Arg Ser Val Val Pro
        115                 120                 125 ggt acc gcc gag gcc gcg gcg ctc aag gcc gcg ctg atc gag gcg ggc   432
Gly Thr Ala Glu Ala Ala Ala Leu Lys Ala Ala Leu Ile Glu Ala Gly
    130                 135                 140 atg tgg tcg caa tat ctc gaa gtg gcg atc ggg ccg gac gcg gag gtg   480
Met Trp Ser Gln Tyr Leu Glu Val Ala Ile Gly Pro Asp Ala Glu Val
145                 150                 155                 160 ttc acc aag gcg ccg gtt ctg tcg gcg atg ggc tgg ggc gcc gag atc   528
Phe Thr Lys Ala Pro Val Leu Ser Ala Met Gly Trp Gly Ala Glu Ile
                165                 170                 175 ggc atc cgc tcg gac agc gac tgg aac aat ccg gag ccg gaa gtg gtg   576
Gly Ile Arg Ser Asp Ser Asp Trp Asn Asn Pro Glu Pro Glu Val Val
            180                 185                 190 ctg gtg gtc gac cgg aat ggt gcg atc aag ggc gcg acg ctc ggc aac   624
Leu Val Val Asp Arg Asn Gly Ala Ile Lys Gly Ala Thr Leu Gly Asn
        195                 200                 205 gac gtc aac ctg cgc gac ttc gag ggc cgc agc gcg ctg ctg ctg ggc   672
Asp Val Asn Leu Arg Asp Phe Glu Gly Arg Ser Ala Leu Leu Leu Gly
    210                 215                 220 aag gcg aag gac aac aat gcc tct acc gcg atc ggc ccg ttc atc cgc   720
Lys Ala Lys Asp Asn Asn Ala Ser Thr Ala Ile Gly Pro Phe Ile Arg
225                 230                 235                 240 ctg ttc gat gac ggc ttc acg atg gac gac gtg cgt agc gcg gtg gtc   768
Leu Phe Asp Asp Gly Phe Thr Met Asp Asp Val Arg Ser Ala Val Val
                245                 250                 255 gac ctc acc atc gac ggg ccg gag ggc tat cgc ctc tcg ggc acc aac   816
Asp Leu Thr Ile Asp Gly Pro Glu Gly Tyr Arg Leu Ser Gly Thr Asn
            260                 265                 270 aag atg agc gag atc agc cga gat ccg acc gag ctc gtg cgc cag acg   864
Lys Met Ser Glu Ile Ser Arg Asp Pro Thr Glu Leu Val Arg Gln Thr
        275                 280                 285 ctg agc gag cac cag tat ccg gac ggc ttc gcg ctg ttc ctc ggc acg   912
Leu Ser Glu His Gln Tyr Pro Asp Gly Phe Ala Leu Phe Leu Gly Thr
    290                 295                 300
```

```
ctg ttc gcg ccg gtg cag gat cgc gac cat ccc ggc cgc ggc ttc act    960
Leu Phe Ala Pro Val Gln Asp Arg Asp His Pro Gly Arg Gly Phe Thr
305                 310                 315                 320 cac aag ccc ggc gat att gtc cgc att tcc acg ccg aag ctc ggc acg   1008
His Lys Pro Gly Asp Ile Val Arg Ile Ser Thr Pro Lys Leu Gly Thr
                325                 330                 335 ctc gtc aac cgc gtc acc acg tcc aag gcc gcc gcg ccc tgg acg ttc   1056
Leu Val Asn Arg Val Thr Thr Ser Lys Ala Ala Ala Pro Trp Thr Phe
            340                 345                 350 ggc atc cgc gat ctg atg cgc aat ctc gcc gcc cgc ggc ctt ctc tcg   1104
Gly Ile Arg Asp Leu Met Arg Asn Leu Ala Ala Arg Gly Leu Leu Ser
        355                 360                 365 cat tcc taa                                                       1113
His Ser
    370

<210> SEQ ID NO 22
<211> LENGTH: 370
<212> TYPE: PRT
<213> ORGANISM: Sphingomonas elodea

<400> SEQUENCE: 22

Met Leu Pro Ala Asp His Ala Gln Ala Ile Leu Val Gly Arg Val Gln
1               5                   10                  15

Thr Pro Ala Gly Pro Ser Pro Val Leu Leu Arg Asp Gly Gln Val Ile
            20                  25                  30

Asp Val Ser Ala Ile Ala Pro Thr Val Ala Asp Leu Leu Glu Arg Asp
        35                  40                  45

Asp Ile Ala Thr Leu Ser Gly Thr Val Leu Cys Ser Val Asp Ala Leu
    50                  55                  60

Gly Thr Glu Ser Ala Pro Gln Val Leu Ala Pro Val Asp Leu Gln Cys
65                  70                  75                  80

Val Lys Ala Ala Gly Val Thr Phe Ala Val Ser Ala Leu Glu Arg Val
                85                  90                  95

Ile Glu Glu Arg Ala Arg Gly Asp Ser Ala Lys Ala Ala Glu Ile Arg
            100                 105                 110

Gly Asp Leu Glu Ala Lys Val Gly Ser Gly Ile Arg Ser Val Val Pro
        115                 120                 125

Gly Thr Ala Glu Ala Ala Leu Lys Ala Ala Leu Ile Glu Ala Gly
    130                 135                 140

Met Trp Ser Gln Tyr Leu Glu Val Ala Ile Gly Pro Asp Ala Glu Val
145                 150                 155                 160

Phe Thr Lys Ala Pro Val Leu Ser Ala Met Gly Trp Gly Ala Glu Ile
                165                 170                 175

Gly Ile Arg Ser Asp Ser Asp Trp Asn Asn Pro Glu Pro Glu Val Val
            180                 185                 190

Leu Val Val Asp Arg Asn Gly Ala Ile Lys Gly Ala Thr Leu Gly Asn
        195                 200                 205

Asp Val Asn Leu Arg Asp Phe Glu Gly Arg Ser Ala Leu Leu Leu Gly
    210                 215                 220

Lys Ala Lys Asp Asn Asn Ala Ser Thr Ala Ile Gly Pro Phe Ile Arg
225                 230                 235                 240

Leu Phe Asp Asp Gly Phe Thr Met Asp Asp Val Arg Ser Ala Val Val
                245                 250                 255

Asp Leu Thr Ile Asp Gly Pro Glu Gly Tyr Arg Leu Ser Gly Thr Asn
            260                 265                 270
```

```
Lys Met Ser Glu Ile Ser Arg Asp Pro Thr Glu Leu Val Arg Gln Thr
        275                 280                 285

Leu Ser Glu His Gln Tyr Pro Asp Gly Phe Ala Leu Phe Leu Gly Thr
    290                 295                 300

Leu Phe Ala Pro Val Gln Asp Arg Asp His Pro Gly Arg Gly Phe Thr
305                 310                 315                 320

His Lys Pro Gly Asp Ile Val Arg Ile Ser Thr Pro Lys Leu Gly Thr
                325                 330                 335

Leu Val Asn Arg Val Thr Thr Ser Lys Ala Ala Ala Pro Trp Thr Phe
            340                 345                 350

Gly Ile Arg Asp Leu Met Arg Asn Leu Ala Ala Arg Gly Leu Leu Ser
        355                 360                 365

His Ser
    370

<210> SEQ ID NO 23
<211> LENGTH: 1467
<212> TYPE: DNA
<213> ORGANISM: Bacillus subtilis
<220> FEATURE:
<221> NAME/KEY: CDS
<222> LOCATION: (1)..(1467)

<400> SEQUENCE: 23 atg tct gtg atc acg gaa caa aac acg tac ctc aac ttt att aac gga      48
Met Ser Val Ile Thr Glu Gln Asn Thr Tyr Leu Asn Phe Ile Asn Gly
1               5                   10                  15 gag tgg gtt aag tct caa tca ggc gat atg gtc aaa gtc gaa aac cct      96
Glu Trp Val Lys Ser Gln Ser Gly Asp Met Val Lys Val Glu Asn Pro
            20                  25                  30 gcc gat gtg aat gat att gtc gga tat gta cag aat tca acg gct gaa     144
Ala Asp Val Asn Asp Ile Val Gly Tyr Val Gln Asn Ser Thr Ala Glu
        35                  40                  45 gat gtg gaa cgt gcc gtc acc gcc gcc aat gaa gcc aaa acg gct tgg     192
Asp Val Glu Arg Ala Val Thr Ala Ala Asn Glu Ala Lys Thr Ala Trp
    50                  55                  60 aga aag ctg acg ggt gcc gag cgc ggc caa tac tta tac aaa aca gcg     240
Arg Lys Leu Thr Gly Ala Glu Arg Gly Gln Tyr Leu Tyr Lys Thr Ala
65                  70                  75                  80 gat atc atg gag cag cgc ttg gag gaa atc gcc gcc tgt gca acg cgt     288
Asp Ile Met Glu Gln Arg Leu Glu Glu Ile Ala Ala Cys Ala Thr Arg
                85                  90                  95 gaa atg ggt aaa aca ttg ccg gaa gcg aag gga gaa aca gcc cgg ggg     336
Glu Met Gly Lys Thr Leu Pro Glu Ala Lys Gly Glu Thr Ala Arg Gly
            100                 105                 110 att gcc att ctg cgc tat tac gcc gga gag ggc atg cga aaa acg ggt     384
Ile Ala Ile Leu Arg Tyr Tyr Ala Gly Glu Gly Met Arg Lys Thr Gly
        115                 120                 125 gac gtc att ccg tct act gac aaa gac gcg ctc atg ttt acc acc cgt     432
Asp Val Ile Pro Ser Thr Asp Lys Asp Ala Leu Met Phe Thr Thr Arg
    130                 135                 140 gtt ccg ctc ggt gtg gtc ggt gtg att tct ccg tgg aac ttc cca gtg     480
Val Pro Leu Gly Val Val Gly Val Ile Ser Pro Trp Asn Phe Pro Val
145                 150                 155                 160 gcg att ccg att tgg aaa atg gcg ccg gca ttg gta tac ggc aat acc     528
Ala Ile Pro Ile Trp Lys Met Ala Pro Ala Leu Val Tyr Gly Asn Thr
                165                 170                 175 gtt gtc atc aaa ccg gcg aca gaa aca gct gtg aca tgc gcg aag atc     576
Val Val Ile Lys Pro Ala Thr Glu Thr Ala Val Thr Cys Ala Lys Ile
            180                 185                 190
```

```
att gcc tgc ttt gag gaa gcg ggg ctc ccg gca ggg gtc atc aat ttg      624
Ile Ala Cys Phe Glu Glu Ala Gly Leu Pro Ala Gly Val Ile Asn Leu
            195                 200                 205 gtg aca ggc ccg ggt tct gtt gtc ggg cag ggg ctt gct gag cat gac      672
Val Thr Gly Pro Gly Ser Val Val Gly Gln Gly Leu Ala Glu His Asp
    210                 215                 220 ggt gta aac gcc gtt acg ttt acc ggt tca aat caa gtc gga aaa atc      720
Gly Val Asn Ala Val Thr Phe Thr Gly Ser Asn Gln Val Gly Lys Ile
225                 230                 235                 240 atc ggg caa gcc gct tta gcg agg gga gcc aaa tat cag ctt gag atg      768
Ile Gly Gln Ala Ala Leu Ala Arg Gly Ala Lys Tyr Gln Leu Glu Met
                245                 250                 255 ggc ggc aaa aac cct gtc atc gta gct gat gac gct gac ctt gaa gct      816
Gly Gly Lys Asn Pro Val Ile Val Ala Asp Asp Ala Asp Leu Glu Ala
            260                 265                 270 gcg gca gaa gct gtc ata acg ggg gcc ttc cgt tca acc ggc cag aaa      864
Ala Ala Glu Ala Val Ile Thr Gly Ala Phe Arg Ser Thr Gly Gln Lys
        275                 280                 285 tgc acc gcg aca agc cgt gtc atc gta caa agc gga att tac gag cgc      912
Cys Thr Ala Thr Ser Arg Val Ile Val Gln Ser Gly Ile Tyr Glu Arg
    290                 295                 300 ttt aaa gaa aaa ctg ctc cag cgc aca aaa gat att aca atc gga gac      960
Phe Lys Glu Lys Leu Leu Gln Arg Thr Lys Asp Ile Thr Ile Gly Asp
305                 310                 315                 320 agc tta aaa gag gat gtc tgg atg gga ccg ata gcc agc aag aat cag     1008
Ser Leu Lys Glu Asp Val Trp Met Gly Pro Ile Ala Ser Lys Asn Gln
                325                 330                 335 ctt gat aac tgc ctg tca tac att gag aaa ggc aaa cag gag ggc gct     1056
Leu Asp Asn Cys Leu Ser Tyr Ile Glu Lys Gly Lys Gln Glu Gly Ala
            340                 345                 350 tcc ctt tta ata gga gga gaa aag ctg gag aac gga aag tat caa aac     1104
Ser Leu Leu Ile Gly Gly Glu Lys Leu Glu Asn Gly Lys Tyr Gln Asn
        355                 360                 365 ggc tat tat gtt cag cct gcc atc ttt gac aat gtg aca tct gag atg     1152
Gly Tyr Tyr Val Gln Pro Ala Ile Phe Asp Asn Val Thr Ser Glu Met
    370                 375                 380 aca att gcc cag gag gaa att ttc ggt ccg gtg atc gcc ttg atc aag     1200
Thr Ile Ala Gln Glu Glu Ile Phe Gly Pro Val Ile Ala Leu Ile Lys
385                 390                 395                 400 gtg gac tcg ata gag gag gcg ctg aac atc gcc aat gat gtg aag ttc     1248
Val Asp Ser Ile Glu Glu Ala Leu Asn Ile Ala Asn Asp Val Lys Phe
                405                 410                 415 ggt tta agt gca tcc atc ttc acg gaa aac atc ggc cga atg ctt tct     1296
Gly Leu Ser Ala Ser Ile Phe Thr Glu Asn Ile Gly Arg Met Leu Ser
            420                 425                 430 ttc att gat gaa atc gat gcc ggg ctg gtt cgg atc aat gca gaa agc     1344
Phe Ile Asp Glu Ile Asp Ala Gly Leu Val Arg Ile Asn Ala Glu Ser
        435                 440                 445 gca ggt gtt gag ctg cag gcg cct ttt ggc ggc atg aag cag tcg agc     1392
Ala Gly Val Glu Leu Gln Ala Pro Phe Gly Gly Met Lys Gln Ser Ser
    450                 455                 460 tcc cac tcc cga gaa cag ggt gag gca gcg aag gac ttt ttc aca gcg     1440
Ser His Ser Arg Glu Gln Gly Glu Ala Ala Lys Asp Phe Phe Thr Ala
465                 470                 475                 480 atc aaa act gtt ttt gtg aag ccg taa                                 1467
Ile Lys Thr Val Phe Val Lys Pro
                485
```

<210> SEQ ID NO 24

```
<211> LENGTH: 488
<212> TYPE: PRT
<213> ORGANISM: Bacillus subtilis

<400> SEQUENCE: 24

Met Ser Val Ile Thr Glu Gln Asn Thr Tyr Leu Asn Phe Ile Asn Gly
1               5                   10                  15

Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Thr Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
                165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
        195                 200                 205

Val Thr Gly Pro Gly Ser Val Val Gly Gln Gly Leu Ala Glu His Asp
    210                 215                 220

Gly Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
                245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
        275                 280                 285

Cys Thr Ala Thr Ser Arg Val Ile Val Gln Ser Gly Ile Tyr Glu Arg
    290                 295                 300

Phe Lys Glu Lys Leu Leu Gln Arg Thr Lys Asp Ile Thr Ile Gly Asp
305                 310                 315                 320

Ser Leu Lys Glu Asp Val Trp Met Gly Pro Ile Ala Ser Lys Asn Gln
                325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asn Gly Lys Tyr Gln Asn
        355                 360                 365

Gly Tyr Tyr Val Gln Pro Ala Ile Phe Asp Asn Val Thr Ser Glu Met
    370                 375                 380

Thr Ile Ala Gln Glu Glu Ile Phe Gly Pro Val Ile Ala Leu Ile Lys
```

```
                385                 390                 395                 400
Val Asp Ser Ile Glu Glu Ala Leu Asn Ile Ala Asn Asp Val Lys Phe
                    405                 410                 415

Gly Leu Ser Ala Ser Ile Phe Thr Glu Asn Ile Gly Arg Met Leu Ser
                420                 425                 430

Phe Ile Asp Glu Ile Asp Ala Gly Leu Val Arg Ile Asn Ala Glu Ser
            435                 440                 445

Ala Gly Val Glu Leu Gln Ala Pro Phe Gly Gly Met Lys Gln Ser Ser
        450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485

<210> SEQ ID NO 25
<211> LENGTH: 3481
<212> TYPE: DNA
<213> ORGANISM: Corynebacterium glutamicum
<220> FEATURE:
<221> NAME/KEY: CDS
<222> LOCATION: (1437)..(3035)

<400> SEQUENCE: 25
```

| | | | | | |
|---|---|---|---|---|---|
| gatcttgccg | atttcggcag | gatcaatgtc | ggcgtgaatg | atcttggcat | caggtgcgaa | 60 |
| agtgtcaacg | tcaccggtga | cgcggtcatc | aaagcgggag | ccgatagcaa | tcagcaggtc | 120 |
| gctgcgctgc | agtgcaccaa | cagcggacac | agtgccatgc | atgcctggca | tacccatgtg | 180 |
| cagctcgtgg | gactctggga | aggttcccag | cgccatcaat | gtggtgacaa | ctggaatgcc | 240 |
| ggtgtgctca | gcgaacgcac | gaagctcttc | gtgggcatca | gccttgataa | cgccgccgcc | 300 |
| aacgtaaagg | acaggcttct | tagactcacc | gatcagtttg | acagcctgct | caatctgtcg | 360 |
| agcatgcggt | gttgaaactg | gcggtagcc | tggcaggtcg | atctttggtg | ccagacgaa | 420 |
| atccaattca | gcgttctgaa | catccttggg | gatatccact | agaacaggac | cagggcgacc | 480 |
| agtaatcgcg | aggtggaatg | cctcagccaa | tgcctgtgga | atgtcgttgg | ggttggtgac | 540 |
| catgaagttg | tgcttggtca | ctggcatggt | gatgccgcgg | atatcggctt | cctggaaagc | 600 |
| atcggtaccc | agcaggctac | ttccgacctg | gccggtgatg | gcaaccatgg | gaacggagtc | 660 |
| caagtttgca | tcagcgattg | gggtaaccaa | gttggttgcg | cctgggccag | aggttgcaat | 720 |
| gcagacgcca | acgcgtccag | taacctgcgc | gtagccggtt | gctgcgtggc | ctgcgccctg | 780 |
| ctcgtggcgc | actaggacgt | ggcgcacctt | tgtggaggaa | tagagcgggt | catacaccgg | 840 |
| tagcaccgca | ccaccaggaa | taccgaacac | gatgtcggcg | ttaagctcct | cgagcgatcg | 900 |
| aacaattgcc | tgtgcacctg | tcatccgctc | aggggcggcg | atcgaccac | ggcttgcaac | 960 |
| cgtggcggga | gtgggctgtt | gagaagctgc | cacattcacg | actttctggc | tcctttacta | 1020 |
| aataaggatt | tcacaggac | ccgtccaagc | caagccgatt | tcaactcagc | ctaaagacaa | 1080 |
| agccctcatt | taaaattgtt | ccgacgcgga | tgcgtgtgca | cgcagtgcga | cagatgtctg | 1140 |
| ttgcaaagtt | ggctacttgg | gtcataacca | acaagaaagc | cctcgttcca | acactgtggt | 1200 |
| gagtgttgtc | gagggcgctt | gacgagacga | cttgaaggc | cgttacggca | ggcgccgcgc | 1260 |
| ggttactact | acaagtcgaa | taatggtcat | ggtgtgtcat | gctacacaca | tcgagtttcc | 1320 |
| aattccacaa | cgcacgaaaa | ttcccacccc | caaaactccc | ccacttcggt | taaggaatca | 1380 |
| ggattctcac | aaagttcagg | caggctcccg | ctacttttca | gcgctaatct | tggctc atg | 1439 |
| | | | | | Met | |

```
att tta ggc gta ccc att caa tat ttg ctc tat tca ttg tgg aat tgg    1487
Ile Leu Gly Val Pro Ile Gln Tyr Leu Leu Tyr Ser Leu Trp Asn Trp
         5                  10                  15 att gtc gat acc ggt ttt gat gta gca att atc ctg gtc ttg gcg ttt    1535
Ile Val Asp Thr Gly Phe Asp Val Ala Ile Ile Leu Val Leu Ala Phe
             20                  25                  30 ttg att cca cgt atc ggc cga ctg gcc atg cgt att atc aag cag cga    1583
Leu Ile Pro Arg Ile Gly Arg Leu Ala Met Arg Ile Ile Lys Gln Arg
         35                  40                  45 gtg gag tct gca gcc gat gcg gac acc act aag aac cag ctc gcg ttc    1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt    1679
Ala Gly Val Gly Val Tyr Ile Ala Gln Ile Val Ala Phe Phe Met Leu
                 70                  75                  80 gcc gtc tcc gcg atg cag gct ttt ggt ttc tct ctc gcg ggc gct gcg    1727
Ala Val Ser Ala Met Gln Ala Phe Gly Phe Ser Leu Ala Gly Ala Ala
             85                  90                  95 att ccg gca acc att gcg tca gct gcc att ggt ctt ggt gcg cag tcg    1775
Ile Pro Ala Thr Ile Ala Ser Ala Ala Ile Gly Leu Gly Ala Gln Ser
         100                 105                 110 att gtt gcg gac ttc ttg gcc gga ttt ttc atc ctg acg gaa aag caa    1823
Ile Val Ala Asp Phe Leu Ala Gly Phe Phe Ile Leu Thr Glu Lys Gln
     115                 120                 125 ttc ggc gtg ggt gac tgg gtg cgc ttt gag ggc aac ggc atc gtt gtt    1871
Phe Gly Val Gly Asp Trp Val Arg Phe Glu Gly Asn Gly Ile Val Val
130                 135                 140                 145 gaa ggc acc gtc att gag atc acc atg cgc gcg acc aaa att cgc acg    1919
Glu Gly Thr Val Ile Glu Ile Thr Met Arg Ala Thr Lys Ile Arg Thr
                 150                 155                 160 att gca caa gag acc gtg atc atc ccg aac tcc acg gcg aaa gtg tgc    1967
Ile Ala Gln Glu Thr Val Ile Ile Pro Asn Ser Thr Ala Lys Val Cys
             165                 170                 175 atc aac aat tct aat aac tgg tcg cgt gcg gtt gtc gtt att ccg atc    2015
Ile Asn Asn Ser Asn Asn Trp Ser Arg Ala Val Val Val Ile Pro Ile
         180                 185                 190 ccc atg ttg ggt tct gaa aac atc aca gat gtc atc gcg cgc tct gaa    2063
Pro Met Leu Gly Ser Glu Asn Ile Thr Asp Val Ile Ala Arg Ser Glu
     195                 200                 205 gct gcg act cgt cgc gca ctt ggc cag gag aaa atc gca ccg gaa atc    2111
Ala Ala Thr Arg Arg Ala Leu Gly Gln Glu Lys Ile Ala Pro Glu Ile
210                 215                 220                 225 ctc ggt gaa ctc gat gtg cac cca gcc acg gaa gtc aca ccg cca acg    2159
Leu Gly Glu Leu Asp Val His Pro Ala Thr Glu Val Thr Pro Pro Thr
                 230                 235                 240 gtg gtc ggc atg ccg tgg atg gtc acc atg cgt ttc ctc gtg caa gtc    2207
Val Val Gly Met Pro Trp Met Val Thr Met Arg Phe Leu Val Gln Val
             245                 250                 255 acc gcc ggc aat caa tgg ctg gtc gaa cgc gcc atc cgc aca gaa atc    2255
Thr Ala Gly Asn Gln Trp Leu Val Glu Arg Ala Ile Arg Thr Glu Ile
         260                 265                 270 atc aac gaa ttc tgg gaa gaa tac ggc agc gca acc act aca tcg gga    2303
Ile Asn Glu Phe Trp Glu Glu Tyr Gly Ser Ala Thr Thr Thr Ser Gly
     275                 280                 285 acc ctc att gat tcc tta cac gtt gag cat gaa gag cca aag acc tcg    2351
Thr Leu Ile Asp Ser Leu His Val Glu His Glu Glu Pro Lys Thr Ser
290                 295                 300                 305 ctt atc gac gcc tcc ccc cag gct ctt aag gaa ccg aag ccg gag gct    2399
Leu Ile Asp Ala Ser Pro Gln Ala Leu Lys Glu Pro Lys Pro Glu Ala
```

```
Leu Ile Asp Ala Ser Pro Gln Ala Leu Lys Glu Pro Lys Pro Glu Ala
            310                 315                 320 gcg gcg acg gtt gca tcg cta gct gca tcg tct aac gac gat gca gac      2447
Ala Ala Thr Val Ala Ser Leu Ala Ala Ser Ser Asn Asp Asp Ala Asp
            325                 330                 335 aat gca gac gcc tcg gcg atc aat gca ggc aat cca gag aag gaa ctt      2495
Asn Ala Asp Ala Ser Ala Ile Asn Ala Gly Asn Pro Glu Lys Glu Leu
            340                 345                 350 gat tcc gat gtg ctg gaa caa gaa ctc tcc agc gaa gaa ccg gaa gaa      2543
Asp Ser Asp Val Leu Glu Gln Glu Leu Ser Ser Glu Glu Pro Glu Glu
        355                 360                 365 aca gca aaa cca gat cac tct ctc cga ggc ttc ttc cgc act gat tac      2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc      2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt      2687
Met Ser Thr Ser Leu Leu Leu Gly Ala Leu Leu Leu Leu Ser Leu Phe
                405                 410                 415 aag gtc atg act gtg gaa cca agt gag aat tgg caa aac tcc agt gga      2735
Lys Val Met Thr Val Glu Pro Ser Glu Asn Trp Gln Asn Ser Ser Gly
                420                 425                 430 tgg ctg tca cca agc act gcc acc tca act gcg gtg acc acc tcc gaa      2783
Trp Leu Ser Pro Ser Thr Ala Thr Ser Thr Ala Val Thr Thr Ser Glu
        435                 440                 445 act tcc gcg cca gca agc acg cct tcg atg aca gtg ccc act acg gtg      2831
Thr Ser Ala Pro Ala Ser Thr Pro Ser Met Thr Val Pro Thr Thr Val
450                 455                 460                 465 gag gag acc cca acg atg gaa tct agc gtc gaa acg cag cag gaa acc      2879
Glu Glu Thr Pro Thr Met Glu Ser Ser Val Glu Thr Gln Gln Glu Thr
                470                 475                 480 tca acc cct gca acc gca acg ccc cag cga gcc gac acc atc gaa ccg      2927
Ser Thr Pro Ala Thr Ala Thr Pro Gln Arg Ala Asp Thr Ile Glu Pro
            485                 490                 495 acc gag gaa gcc acg tcg cag gag gaa acg act gca tcg cag acg cag      2975
Thr Glu Glu Ala Thr Ser Gln Glu Glu Thr Thr Ala Ser Gln Thr Gln
            500                 505                 510 tct cca gca gtg gaa gca cca acc gcg gtc caa gaa aca gtt gcg ccg      3023
Ser Pro Ala Val Glu Ala Pro Thr Ala Val Gln Glu Thr Val Ala Pro
        515                 520                 525 acg tcc acc cct taggacgctg attacagacg tgtcccattt ctttactact          3075
Thr Ser Thr Pro
530 attggaaatt atgagttcag acgcagaaaa ggcatccgtg gagctttccg aaaaatttca    3135 cccagaacgc acccatattt tgggcgccgt tgtttttggc ctgatctcat tattagtcat    3195 cggcgcagcc cctcagtacc tgttttggct gctcgcgctc cctgtcatct tcggttactg    3255 ggttctaaaa tcatccacga tcgttgatga acagggcatc accgcaaact acgccttcaa    3315 gggcaaaaag gttgtggcct gggaagacct cgcaggaatc ggattcaagg gtgcccgcac    3375 tttcgctcgc accacctccg atgcagaagt caccctcccc ggcgtcacct tcaactccct    3435 tccccgcctt gaagctgctt cccacggccg catccccgat gcgatc                   3481

<210> SEQ ID NO 26
<211> LENGTH: 533
<212> TYPE: PRT
<213> ORGANISM: Corynebacterium glutamicum
```

<400> SEQUENCE: 26

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415
```

```
Phe Lys Val Met Thr Val Glu Pro Ser Glu Asn Trp Gln Asn Ser Ser
            420                 425                 430
Gly Trp Leu Ser Pro Ser Thr Ala Thr Ser Thr Ala Val Thr Thr Ser
        435                 440                 445
Glu Thr Ser Ala Pro Ala Ser Thr Pro Ser Met Thr Val Pro Thr Thr
450                 455                 460
Val Glu Glu Thr Pro Thr Met Glu Ser Ser Val Glu Thr Gln Gln Glu
465                 470                 475                 480
Thr Ser Thr Pro Ala Thr Ala Thr Pro Gln Arg Ala Asp Thr Ile Glu
                485                 490                 495
Pro Thr Glu Glu Ala Thr Ser Gln Glu Glu Thr Thr Ala Ser Gln Thr
            500                 505                 510
Gln Ser Pro Ala Val Glu Ala Pro Thr Ala Val Gln Glu Thr Val Ala
        515                 520                 525
Pro Thr Ser Thr Pro
    530
```

<210> SEQ ID NO 27
<211> LENGTH: 44
<212> TYPE: DNA
<213> ORGANISM: Artificial Sequence
<220> FEATURE:
<223> OTHER INFORMATION: primer

<400> SEQUENCE: 27
tacccgggga tcctctaggc gctgaactca caattccgat tagt            44

<210> SEQ ID NO 28
<211> LENGTH: 50
<212> TYPE: DNA
<213> ORGANISM: Artificial Sequence
<220> FEATURE:
<223> OTHER INFORMATION: primer

<400> SEQUENCE: 28
atattcagcg ggttctggaa ccacattggg tggaactcta gattccaaga      50

<210> SEQ ID NO 29
<211> LENGTH: 50
<212> TYPE: DNA
<213> ORGANISM: Artificial Sequence
<220> FEATURE:
<223> OTHER INFORMATION: primer

<400> SEQUENCE: 29
tcttggaatc tagagttcca cccaatgtgg ttccagaacc cgctgaatat      50

<210> SEQ ID NO 30
<211> LENGTH: 41
<212> TYPE: DNA
<213> ORGANISM: Artificial Sequence
<220> FEATURE:
<223> OTHER INFORMATION: primer

<400> SEQUENCE: 30
tgcaggtcga ctctaggggc aggttttggt gtggcaggat g              41

<210> SEQ ID NO 31
<211> LENGTH: 39
<212> TYPE: DNA
<213> ORGANISM: Artificial Sequence
<220> FEATURE:

<223> OTHER INFORMATION: primer

<400> SEQUENCE: 31
ggagccttcg cctctatgac cattgagaaa attttcacc            39

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
tggttcttgg aatctttaaa ttccgagcgc ttttttaccg           40

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33
attgggtgga actctaaatt cctgtgaagt agctgat              37

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
agaggcgaag gctccttgaa taggta                          26

<210> SEQ ID NO 35
<211> LENGTH: 1383
<212> TYPE: DNA
<213> ORGANISM: Corynebacterium glutamicum

<400> SEQUENCE: 35
atggctctgg ttcttggaat cgatagttcc acccaatcct gcaaggcttt gcttgtcgac    60
gccgccagcg gccgcattat cgacgaaggc cgcgcgagtc acccgagcgg gtcggaggta   120
gatccacgtg cgtggatcgc tgcgctggat caagctaccg aggggttgct agaacgtgcg   180
gatgctgtgt ctattgcagg ccagcagcac ggcatggtgg cgttggatga aaacgatgaa   240
atcgttcgcc cggcgttgtt gtggaatgac actcgttctg cccaggctgc gttggatctc   300
aatgaggaga tcggcggcga tcaggctgcg gtagatgcca cggaagtgt gtatgttgct   360
tctttaactg ccaccaagat gcggtggatg cgtgatcatg agccagaaaa tgcagcgcgt   420
acagcgtcgg tgatgttgcc tcatgatttc ctcacctggc atttgatggg acgtggccgc   480
aaagtcactg atcatggtga tgcttccgga acgggctact acagcactcg tgatcgtgcg   540
tggcgcaccg atctagctgc cttggcgctg ggccatgagg tggaacttcc tgaactcctg   600
gctccgaatg agattgcggg aacaactcca gtggtgtga agttgctgc aggcacgggc    660
gataatgctg cggctgcgct tggccttgat ttgcatccag gcgatgtcag cgtgtcgatc   720
ggcacctcag gcgttgccgg catgactgtt caaaacagcg tccacgatcc gtctggtctg   780
gtcactggtt ttgccgatgc cacgggtgcg tatttcccgc tggcctgcac gctcaatggc   840
gcaccggtgc tggaattcgg ccgccgcatt ctgggcgtgg aatgggaaga gttcgatgcg   900

```
cttgcgctag ctgctcaacc cggttcaggt ggagtaacgt tccagcctta tttggagggc    960
gagcgtacgc cgaatcgtcc cgcagcacgt ggcgttttgg ctggactaaa cagtgcaact   1020 accgcgagg attttgcccg cgcaactgtt gaaggcttgt tgttggcgtt agatgatgct   1080
gtaacggctc tggttgaggc cacggggtg cccgttcagc gcattcaact catcggtggc   1140
ggcgcgcgtt cacgggcagt tcgtgagatc gctcctgaga ttttcggcca tgagattgtg   1200
gttccagaac ccgctgaata tgtggcgttg ggtgcagctc gtcaggcggc atgggcgctg   1260
tcgggtgagg ccacgccacc gcagtggcca acccttggtt cagatccgca ccgcgcgccc   1320
aaaaacactg agctgagcac gcgttatgcg aagctgcgtg atgcaacgca gggttggtac   1380
tag                                                                1383
```

<210> SEQ ID NO 36  
<211> LENGTH: 460  
<212> TYPE: PRT  
<213> ORGANISM: Corynebacterium glutamicum

<400> SEQUENCE: 36

```
Met Ala Leu Val Leu Gly Ile Asp Ser Thr Gln Ser Cys Lys Ala
1               5                   10                  15

Leu Leu Val Asp Ala Ala Ser Gly Arg Ile Ile Asp Glu Gly Arg Ala
            20                  25                  30

Ser His Pro Ser Gly Ser Glu Val Asp Pro Arg Ala Trp Ile Ala Ala
        35                  40                  45

Leu Asp Gln Ala Thr Glu Gly Leu Leu Glu Arg Ala Asp Ala Val Ser
    50                  55                  60

Ile Ala Gly Gln Gln His Gly Met Val Ala Leu Asp Glu Asn Asp Glu
65                  70                  75                  80

Ile Val Arg Pro Ala Leu Leu Trp Asn Asp Thr Arg Ser Ala Gln Ala
                85                  90                  95

Ala Leu Asp Leu Asn Glu Glu Ile Gly Gly Asp Gln Ala Ala Val Asp
            100                 105                 110

Ala Thr Gly Ser Val Tyr Val Ala Ser Leu Thr Ala Thr Lys Met Arg
        115                 120                 125

Trp Met Arg Asp His Glu Pro Glu Asn Ala Ala Arg Thr Ala Ser Val
    130                 135                 140

Met Leu Pro His Asp Phe Leu Thr Trp His Leu Met Gly Arg Gly Arg
145                 150                 155                 160

Lys Val Thr Asp His Gly Asp Ala Ser Gly Thr Gly Tyr Tyr Ser Thr
                165                 170                 175

Arg Asp Arg Ala Trp Arg Thr Asp Leu Ala Ala Leu Ala Leu Gly His
            180                 185                 190

Glu Val Glu Leu Pro Glu Leu Leu Ala Pro Asn Glu Ile Ala Gly Thr
        195                 200                 205

Thr Pro Gly Gly Val Lys Val Ala Ala Gly Thr Gly Asp Asn Ala Ala
    210                 215                 220

Ala Ala Leu Gly Leu Asp Leu His Pro Gly Asp Val Ser Val Ser Ile
225                 230                 235                 240

Gly Thr Ser Gly Val Ala Gly Met Thr Val Gln Asn Ser Val His Asp
                245                 250                 255

Pro Ser Gly Leu Val Thr Gly Phe Ala Asp Ala Thr Gly Ala Tyr Phe
            260                 265                 270

Pro Leu Ala Cys Thr Leu Asn Gly Ala Pro Val Leu Glu Phe Gly Arg
```

```
                275                 280                 285
Arg Ile Leu Gly Val Glu Trp Glu Glu Phe Asp Ala Leu Ala Leu Ala
            290                 295                 300
Ala Gln Pro Gly Ser Gly Val Thr Phe Gln Pro Tyr Leu Glu Gly
305                 310                 315                 320
Glu Arg Thr Pro Asn Arg Pro Ala Ala Arg Gly Val Leu Ala Gly Leu
                325                 330                 335
Asn Ser Ala Thr Thr Arg Glu Asp Phe Ala Arg Ala Thr Val Glu Gly
            340                 345                 350
Leu Leu Leu Ala Leu Asp Asp Ala Val Thr Ala Leu Val Glu Ala Thr
            355                 360                 365
Gly Val Pro Val Gln Arg Ile Gln Leu Ile Gly Gly Ala Arg Ser
    370                 375                 380
Arg Ala Val Arg Glu Ile Ala Pro Glu Ile Phe Gly His Glu Ile Val
385                 390                 395                 400
Val Pro Glu Pro Ala Glu Tyr Val Ala Leu Gly Ala Ala Arg Gln Ala
                405                 410                 415
Ala Trp Ala Leu Ser Gly Glu Ala Thr Pro Pro Gln Trp Pro Thr Leu
            420                 425                 430
Gly Ser Asp Pro His Arg Ala Pro Lys Asn Thr Glu Leu Ser Thr Arg
            435                 440                 445
Tyr Ala Lys Leu Arg Asp Ala Thr Gln Gly Trp Tyr
450                 455                 460

<210> SEQ ID NO 37
<211> LENGTH: 1437
<212> TYPE: DNA
<213> ORGANISM: Caulobacter crescentus

<400> SEQUENCE: 37
atgaccgaca ccctgcgcca ttacatcggc ggcgaacgcg tcgcggccga cgccccggcc      60
gagagcctga acccgtccaa caccaacgac gtcgtcgcca aggtcccgat gggcggccag     120
gccgaggtcg acgccgccgt cgacgccgcg cgcaaggcct tcccggcctg gccgacgcc      180 tcgccggagg tccgctcgga cctcttggac aaggtcggtt cgaccatcat cgcccgcagc     240
gccgacatcg gccgcctgct ggcccgcgaa gagggcaaga ccctggcgga aggcatcggc     300
gagaccgtcc gcgccggccg catcttcaag tacttcgccg gtgaagccct cgccgtcac      360 ggccagaacc tggaaagcac ccgtccgggc gtcgagatcc agacctatcg tcaggccgtg     420
ggcgtctatg gcctgatcac gccctggaac ttcccgatcg ccatcccggc ctggaaggcc     480
gccccggcgc tcgccttcgg caacaccgtg gtgatcaagc cggccggccc gacgcccgcc     540
accgccaacg tgctggccga catcatggcc gagtgcggcg ccccggccgg cgtgttcaac     600
atgctgtttg gtcgcggctc gatgggcgat gcgctgatca agcacaagga cgtggacggc     660
gtctcgttca ccggctcgca gggcgtgggc gcgcaggtcg ccgccgccgc cgtgcccgt      720 caggcccgcg tgcagctgga gatgggcggc aagaacccgc tgatcgtgct ggacgacgcc     780
gacctggagc gcgcggtcgc catcgccctg acggctcgt tcttcgccac cggccagcgc      840
tgcaccgcca gctcgcgcct gatcgtccag acgggattc acgacaagtt cgtggccctg     900
ctggccgaga aggtcgccgc cctgcgcgtg ggcgacgctc tggaccccaa caccccagatc    960 ggcccggccc tctccgaaga ccagatggag acttcgtacc gctatatcga catcgctgcc    1020
tccgaaggcg gccgcgtggt caccggcggc gaccgcatca agctcgacaa tccgggctgg    1080
```

-continued

```
tacgtgcgtc cgaccctgat cgccgacacg caagccggca tgcggatcaa caacgaggag    1140
gtcttcggcc ccgtcgcctc gaccatccgc gtcaagagct acgaagaggc gctggagatc    1200
gccaacggcg tcgagttcgg cctttcggcc ggcatcgcca ccacctcgct caagcacgcc    1260
cgccacttcc agcgctatgc ccgcgcgggc atgaccatgg tcaatctggc cacggccggc    1320
gtcgactatc acgtgccgtt cggcggcacg aagagcagct cgtacggcgc ccgcgagcag    1380
ggcttcgcgg cggtcgagtt cttcacccag accaaaacct cctactcgtg gtcgtaa      1437
```

<210> SEQ ID NO 38
<211> LENGTH: 478
<212> TYPE: PRT
<213> ORGANISM: Caulobacter crescentus

<400> SEQUENCE: 38

```
Met Thr Asp Thr Leu Arg His Tyr Ile Gly Gly Glu Arg Val Ala Ala
1               5                   10                  15

Asp Ala Pro Ala Glu Ser Leu Asn Pro Ser Asn Thr Asn Asp Val Val
            20                  25                  30

Ala Lys Val Pro Met Gly Gly Gln Ala Glu Val Asp Ala Ala Val Asp
        35                  40                  45

Ala Ala Arg Lys Ala Phe Pro Ala Trp Ala Asp Ala Ser Pro Glu Val
    50                  55                  60

Arg Ser Asp Leu Leu Asp Lys Val Gly Ser Thr Ile Ile Ala Arg Ser
65                  70                  75                  80

Ala Asp Ile Gly Arg Leu Leu Ala Arg Glu Glu Gly Lys Thr Leu Ala
                85                  90                  95

Glu Gly Ile Gly Glu Thr Val Arg Ala Gly Arg Ile Phe Lys Tyr Phe
            100                 105                 110

Ala Gly Glu Ala Leu Arg Arg His Gly Gln Asn Leu Glu Ser Thr Arg
        115                 120                 125

Pro Gly Val Glu Ile Gln Thr Tyr Arg Gln Ala Val Gly Val Tyr Gly
    130                 135                 140

Leu Ile Thr Pro Trp Asn Phe Pro Ile Ala Ile Pro Ala Trp Lys Ala
145                 150                 155                 160

Ala Pro Ala Leu Ala Phe Gly Asn Thr Val Val Ile Lys Pro Ala Gly
                165                 170                 175

Pro Thr Pro Ala Thr Ala Asn Val Leu Ala Asp Ile Met Ala Glu Cys
            180                 185                 190

Gly Ala Pro Ala Gly Val Phe Asn Met Leu Phe Gly Arg Gly Ser Met
        195                 200                 205

Gly Asp Ala Leu Ile Lys His Lys Asp Val Asp Gly Val Ser Phe Thr
    210                 215                 220

Gly Ser Gln Gly Val Gly Ala Gln Val Ala Ala Ala Val Ala Arg
225                 230                 235                 240

Gln Ala Arg Val Gln Leu Glu Met Gly Gly Lys Asn Pro Leu Ile Val
                245                 250                 255

Leu Asp Asp Ala Asp Leu Glu Arg Ala Val Ala Ile Ala Leu Asp Gly
            260                 265                 270

Ser Phe Phe Ala Thr Gly Gln Arg Cys Thr Ala Ser Ser Arg Leu Ile
        275                 280                 285

Val Gln Asp Gly Ile His Asp Lys Phe Val Ala Leu Leu Ala Glu Lys
    290                 295                 300

Val Ala Ala Leu Arg Val Gly Asp Ala Leu Asp Pro Asn Thr Gln Ile
305                 310                 315                 320
```

Gly Pro Ala Val Ser Glu Asp Gln Met Glu Thr Ser Tyr Arg Tyr Ile
            325                 330                 335

Asp Ile Ala Ala Ser Glu Gly Gly Arg Val Val Thr Gly Gly Asp Arg
            340                 345                 350

Ile Lys Leu Asp Asn Pro Gly Trp Tyr Val Arg Pro Thr Leu Ile Ala
            355                 360                 365

Asp Thr Gln Ala Gly Met Arg Ile Asn Asn Glu Glu Val Phe Gly Pro
        370                 375                 380

Val Ala Ser Thr Ile Arg Val Lys Ser Tyr Glu Glu Ala Leu Glu Ile
385                 390                 395                 400

Ala Asn Gly Val Glu Phe Gly Leu Ser Ala Gly Ile Ala Thr Thr Ser
            405                 410                 415

Leu Lys His Ala Arg His Phe Gln Arg Tyr Ala Arg Ala Gly Met Thr
            420                 425                 430

Met Val Asn Leu Ala Thr Ala Gly Val Asp Tyr His Val Pro Phe Gly
        435                 440                 445

Gly Thr Lys Ser Ser Ser Tyr Gly Ala Arg Glu Gln Gly Phe Ala Ala
            450                 455                 460

Val Glu Phe Phe Thr Gln Thr Lys Thr Ser Tyr Ser Trp Ser
465                 470                 475

<210> SEQ ID NO 39
<211> LENGTH: 747
<212> TYPE: DNA
<213> ORGANISM: Caulobacter crescentus

<400> SEQUENCE: 39

```
atgtcctcag ccatctatcc cagcctgaag ggcaagcgcg tcgtcatcac cggcggcggc      60
tcgggcatcg gggccggcct caccgccggc ttcgcccgtc agggcgcgga ggtgatcttc     120
ctcgacatcg ccgacgagga ctccagggct cttgaggccg agctggccgg ctcgccgatc     180
ccgccggtct acaagcgctg cgacctgatg aacctcgagg cgatcaaggc ggtcttcgcc     240
gagatcggcg acgtcgacgt gctggtcaac aacgccggca tgacgaccg ccacaagctg      300
gccgacgtga ccgcgccta tgggacgag cggatcaacg tcaacctgcg ccacatgctg       360
ttctgcaccc aggccgtcgc gccgggcatg aagaagcgtg cggcggggc ggtgatcaac       420
ttcggttcga tcagctggca cctggggctt gaggacctcg tcctctacga aaccgccaag     480
gccggcatcg aaggcatgac ccgcgcgctg gcccgggagc tgggtcccga cgacatccgc     540
gtcacctgcg tggtgccggg caacgtcaag accaagcgcc aggagaagtg gtacacgccc     600
gaaggcgagg cccagatcgt ggcggcccaa tgcctgaagg ccgcatcgt cccggagaac      660
gtcgccgcgc tggtgctgtt cctggcctcg gatgacgcgt cgctctgcac cggccacgaa     720
tactggatcg acgccggctg cgttga                                           747
```

<210> SEQ ID NO 40
<211> LENGTH: 248
<212> TYPE: PRT
<213> ORGANISM: Caulobacter crescentus

<400> SEQUENCE: 40

Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
            35                  40                  45

Arg Ala Leu Glu Ala Glu Leu Ala Gly Ser Pro Ile Pro Pro Val Tyr
 50                  55                  60

Lys Arg Cys Asp Leu Met Asn Leu Glu Ala Ile Lys Ala Val Phe Ala
 65                  70                  75                  80

Glu Ile Gly Asp Val Asp Val Leu Val Asn Asn Ala Gly Asn Asp Asp
                 85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
            115                 120                 125

Gly Met Lys Lys Arg Gly Gly Ala Val Ile Asn Phe Gly Ser Ile
130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
            195                 200                 205

Ala Gln Cys Leu Lys Gly Arg Ile Val Pro Glu Asn Val Ala Ala Leu
            210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245

<210> SEQ ID NO 41
<211> LENGTH: 870
<212> TYPE: DNA
<213> ORGANISM: Caulobacter crescentus

<400> SEQUENCE: 41
atgaccgctc aagtcacttg cgtatgggat ctgaaggcca cgttgggcga aggcccgatc      60
tggcatggcg acaccctgtg gttcgtcgac atcaagcagc gtaaaatcca caactaccac     120
cccgccaccg gcgagcgctt cagcttcgac gcgccggatc aggtgacctt cctcgcgccg     180
atcgtcggcg cgaccggctt tgtcgtcggt ctgaagaccg ggattcaccg cttccacccg     240
gccacgggct tcagcctgct gctcgaggtc gaggacgcgg cgctgaacaa ccgccccaac     300
gacgccacgg tcgacgcgca aggccgtctg tggttcggca ccatgcacga cggggaagag     360
aacaatagcg gctcgctcta tcggatggac ctcaccggcg tcgcccggat ggaccgcgac     420
atctgcatca ccaacggccc gtgcgtctcg cccgacggca agaccttcta ccacaccgac     480
accctggaaa agacgatcta cgccttcgac ctggccgagg acggcctgct gtcgaacaag     540
cgcgtcttcg tgcagttcgc cctgggcgac gatgtctatc cggacggttc ggtcgtcgat     600
tccgaaggct atctgtggac cgccctgtgg ggcggtttcg cgcgcggtcc gcttctcgccg    660 caaggcgacg ccgtgacgcg catcgaactg cccgccccca acgtcaccaa gccctgcttc     720
ggcgggcctg acctgaagac cctctatttc accaccgccc gcaagggcct gagcgacgag     780
accctgcccc agtacccgct ggccggcggt gtgttcgccg ttccggtcga tgtggccggc     840
caaccccagc atgaggtccg ccttgtctaa                                      870

<210> SEQ ID NO 42
<211> LENGTH: 289
<212> TYPE: PRT
<213> ORGANISM: Caulobacter crescentus

<400> SEQUENCE: 42

Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
            20                  25                  30

Gln Arg Lys Ile His Asn Tyr His Pro Ala Thr Gly Glu Arg Phe Ser
        35                  40                  45

Phe Asp Ala Pro Asp Gln Val Thr Phe Leu Ala Pro Ile Val Gly Ala
    50                  55                  60

Thr Gly Phe Val Val Gly Leu Lys Thr Gly Ile His Arg Phe His Pro
65                  70                  75                  80

Ala Thr Gly Phe Ser Leu Leu Leu Glu Val Glu Asp Ala Ala Leu Asn
                85                  90                  95

Asn Arg Pro Asn Asp Ala Thr Val Asp Ala Gln Gly Arg Leu Trp Phe
            100                 105                 110

Gly Thr Met His Asp Gly Glu Glu Asn Asn Ser Gly Ser Leu Tyr Arg
        115                 120                 125

Met Asp Leu Thr Gly Val Ala Arg Met Asp Arg Asp Ile Cys Ile Thr
    130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                165                 170                 175

Leu Ser Asn Lys Arg Val Phe Val Gln Phe Ala Leu Gly Asp Asp Val
            180                 185                 190

Tyr Pro Asp Gly Ser Val Val Asp Ser Glu Gly Tyr Leu Trp Thr Ala
        195                 200                 205

Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255

Leu Ser Asp Glu Thr Leu Ala Gln Tyr Pro Leu Ala Gly Gly Val Phe
            260                 265                 270

Ala Val Pro Val Asp Val Ala Gly Gln Pro Gln His Glu Val Arg Leu
        275                 280                 285

Val

<210> SEQ ID NO 43
<211> LENGTH: 1788
<212> TYPE: DNA
<213> ORGANISM: Caulobacter crescentus

<400> SEQUENCE: 43
atgaggtccg ccttgtctaa ccgcacgccc cgccggttcc ggtcccgcga ttggttcgat      60
aaccccgacc atatcgacat gaccgcgctc tatctggagc gcttcatgaa ctacgggatc     120
acgccggagg agctgcgcag cggcaagccg atcatcggca tcgcccagac cggcagcgac     180

-continued

```
atctcgccct gcaaccgcat ccacctggac ctggtccagc gggtgcggga cgggatccgc    240
gacgccgggg gcatccccat ggagttcccg gtccatccga tcttcgagaa ctgccgtcgc    300
ccgacggcgg cgctggaccg gaacctctcg tacctgggtc tcgtcgagac cctgcacggc    360
tatccgatcg acgccgtggt tctgaccacc ggctgcgaca agaccacccc ggccgggatc    420
atggccgcca ccacggtcaa tatcccggcc atcgtgctgt cgggcggccc gatgctggac    480
ggctggcacg agaacgagct cgtgggctcg gcaccgtga tctggcgctc cgccgcaag    540 ctggcggccg gcgagatcac cgaggaagag ttcatcgacc gcgccgccag ctcggcgccg    600
tcggcgggcc actgcaacac catgggcacg gcctcgacca tgaacgccgt ggccgaggcg    660
ctgggcctgt cgctgaccgg ctgcgcggcc atccccgccc cctaccgcga gcgcggccag    720
atggcctaca agaccggcca gcgcatcgtc gatctggcct atgacgacgt caaaccgctc    780
gacatcctga ccaagcaagc cttcgagaac gccatcgccc tggtggcggc ggccggcgg    840 tcgaccaacg cccagccgca catcgtggcc atggcccgtc acgccggcgt cgagatcacc    900
gccgacgact ggcgcgcggc ctatgacatc ccgctgatcg tcaacatgca gccggccggc    960
aagtatctgg gcgagcgctt ccaccgagcc ggcggcgcgc cggcggtgct gtgggagctg   1020
ttgcagcaag gccgcctgca cggcgacgtg ctgaccgtca ccggcaagac gatgagcgag   1080
aacctgcaag gccgcgaaac cagcgaccgc gaggtgatct ccccgtacca cgagccgctg   1140
gccgagaagg ccgggttcct ggttctcaag ggcaacctct tcgacttcgc gatcatgaag   1200
tccagcgtga tcggcgagga gttccgcaag cgctacctgt cgcagcccgg ccaggaaggc   1260
gtgttcgaag cccgcgccat cgtgttcgac ggctcggacg actatcacaa gcggatcaac   1320
gatccggccc tggagatcga cgagcgctgc atcctggtga tccgcggcgc gggtccgatc   1380
ggctggcccg gctcggccga ggtcgtcaac atgcagccgc cggatcacct tctgaagaag   1440
gggatcatga gcctgcccac cctgggcgat ggccgtcagt cgggcaccgc cgacagcccc   1500
tcgatcctga acgcctcgcc cgaaagcgcg atcggcggcg cctgtcgtg gctgcgcacc   1560 ggcgacacca tccgcatcga cctcaacacc ggccgctgcg acgccctggt cgacgaggcg   1620
acgatcgccg cgcgcaagca ggacggcatc ccggcggttc ccgccaccat gacgccctgg   1680
caggaaatct accgcgccca cgccagtcag ctcgacaccg gcggcgtgct ggagttcgcg   1740
gtcaagtacc aggacctggc ggccaagctg ccccgccaca accactga                1788
```

<210> SEQ ID NO 44
<211> LENGTH: 595
<212> TYPE: PRT
<213> ORGANISM: Caulobacter crescentus

<400> SEQUENCE: 44

```
Met Arg Ser Ala Leu Ser Asn Arg Thr Pro Arg Phe Arg Ser Arg
1               5                  10                  15

Asp Trp Phe Asp Asn Pro Asp His Ile Asp Met Thr Ala Leu Tyr Leu
            20                  25                  30

Glu Arg Phe Met Asn Tyr Gly Ile Thr Pro Glu Glu Leu Arg Ser Gly
        35                  40                  45

Lys Pro Ile Ile Gly Ile Ala Gln Thr Gly Ser Asp Ile Ser Pro Cys
    50                  55                  60

Asn Arg Ile His Leu Asp Leu Val Gln Arg Val Arg Asp Gly Ile Arg
65                  70                  75                  80

Asp Ala Gly Gly Ile Pro Met Glu Phe Pro Val His Pro Ile Phe Glu
                85                  90                  95
```

```
Asn Cys Arg Arg Pro Thr Ala Ala Leu Asp Arg Asn Leu Ser Tyr Leu
            100                 105                 110

Gly Leu Val Glu Thr Leu His Gly Tyr Pro Ile Asp Ala Val Val Leu
            115                 120                 125

Thr Thr Gly Cys Asp Lys Thr Thr Pro Ala Gly Ile Met Ala Ala Thr
        130                 135                 140

Thr Val Asn Ile Pro Ala Ile Val Leu Ser Gly Gly Pro Met Leu Asp
145                 150                 155                 160

Gly Trp His Glu Asn Glu Leu Val Gly Ser Gly Thr Val Ile Trp Arg
                165                 170                 175

Ser Arg Arg Lys Leu Ala Ala Gly Glu Ile Thr Glu Glu Phe Ile
            180                 185                 190

Asp Arg Ala Ala Ser Ser Ala Pro Ser Ala Gly His Cys Asn Thr Met
            195                 200                 205

Gly Thr Ala Ser Thr Met Asn Ala Val Ala Glu Ala Leu Gly Leu Ser
        210                 215                 220

Leu Thr Gly Cys Ala Ala Ile Pro Ala Pro Tyr Arg Glu Arg Gly Gln
225                 230                 235                 240

Met Ala Tyr Lys Thr Gly Gln Arg Ile Val Asp Leu Ala Tyr Asp Asp
                245                 250                 255

Val Lys Pro Leu Asp Ile Leu Thr Lys Gln Ala Phe Glu Asn Ala Ile
            260                 265                 270

Ala Leu Val Ala Ala Ala Gly Gly Ser Thr Asn Ala Gln Pro His Ile
        275                 280                 285

Val Ala Met Ala Arg His Ala Gly Val Glu Ile Thr Ala Asp Asp Trp
290                 295                 300

Arg Ala Ala Tyr Asp Ile Pro Leu Ile Val Asn Met Gln Pro Ala Gly
305                 310                 315                 320

Lys Tyr Leu Gly Glu Arg Phe His Arg Ala Gly Gly Ala Pro Ala Val
                325                 330                 335

Leu Trp Glu Leu Leu Gln Gln Gly Arg Leu His Gly Asp Val Leu Thr
            340                 345                 350

Val Thr Gly Lys Thr Met Ser Glu Asn Leu Gln Gly Arg Glu Thr Ser
        355                 360                 365

Asp Arg Glu Val Ile Phe Pro Tyr His Glu Pro Leu Ala Glu Lys Ala
        370                 375                 380

Gly Phe Leu Val Leu Lys Gly Asn Leu Phe Asp Phe Ala Ile Met Lys
385                 390                 395                 400

Ser Ser Val Ile Gly Glu Glu Phe Arg Lys Arg Tyr Leu Ser Gln Pro
                405                 410                 415

Gly Gln Glu Gly Val Phe Glu Ala Arg Ala Ile Val Phe Asp Gly Ser
            420                 425                 430

Asp Asp Tyr His Lys Arg Ile Asn Asp Pro Ala Leu Glu Ile Asp Glu
        435                 440                 445

Arg Cys Ile Leu Val Ile Arg Gly Ala Gly Pro Ile Gly Trp Pro Gly
        450                 455                 460

Ser Ala Glu Val Val Asn Met Gln Pro Pro Asp His Leu Leu Lys Lys
465                 470                 475                 480

Gly Ile Met Ser Leu Pro Thr Leu Gly Asp Gly Arg Gln Ser Gly Thr
                485                 490                 495

Ala Asp Ser Pro Ser Ile Leu Asn Ala Ser Pro Glu Ser Ala Ile Gly
            500                 505                 510
```

-continued

```
Gly Gly Leu Ser Trp Leu Arg Thr Gly Asp Thr Ile Arg Ile Asp Leu
            515                 520                 525

Asn Thr Gly Arg Cys Asp Ala Leu Val Asp Glu Ala Thr Ile Ala Ala
        530                 535                 540

Arg Lys Gln Asp Gly Ile Pro Ala Val Pro Ala Thr Met Thr Pro Trp
545                 550                 555                 560

Gln Glu Ile Tyr Arg Ala His Ala Ser Gln Leu Asp Thr Gly Gly Val
                565                 570                 575

Leu Glu Phe Ala Val Lys Tyr Gln Asp Leu Ala Ala Lys Leu Pro Arg
            580                 585                 590

His Asn His
        595

<210> SEQ ID NO 45
<211> LENGTH: 1329
<212> TYPE: DNA
<213> ORGANISM: Caulobacter crescentus

<400> SEQUENCE: 45
gtggtttgtc ggcggcttct agcatggacc gcccgcgccc gtgaggccga ggatttcgcg      60
ctggtcagac aacctacttg ccgtccccac atgttagcgc taccaagtgc cgacgaacgc     120
gcgccgccga cggtgtcggc gcttcagacg ctcgagtttt ggggagacga cgccgtgggc     180
gtgagtgaat tcctgccgga agattggaaa gccgcgaccc tgctggggcg catcgacttt     240
ggcgaaggcc cgacgccggt gctggtgcgc ggcggccgcg tcgaggacgt ctcgaagatc     300
gcccccaccg tcgctgacct gatgaacgcc ttccagcccg gcgcggtgat cccgcgcggc     360
gaggacaagg gtccgctgga agccctcgac atccgcccag tctgggaaga cccggacggc     420
gccgcgccgg tcaagctgtt ggcccccgtc gacctgcaat gcctgaaggc cgccggcgtg     480
accttcgcgg tctcgaccct tgagcgggtc atcgaggagc gcgcgcgcgg cgacgccggc     540
gaggcgctga agatccgcac cctgctggcc gaacgcatgg cggcgaccct caagagcgtc     600
gagccgggct cgcagggcgc ccagcgcctg aaggacgccc tgatcgccga cggcctgtgg     660
tcgcagtatc tggaagtggc gatcggcccg gacgccgaga tcttcaccaa gggcccgacc     720
ctgtcctcga tgggctgggg cgaccaggtc ggcgtccgct atgacagcca ctggaacaat     780
cccgagccgg aagtcgtgct gctgtgcgac ggttcgggcc tgatccgcgg cgcggcgctg     840
ggcaacgacg tcaatctgcg cgacttcgaa ggtcgttcgg ccctgctgct cagcaaggcc     900
aaggacaaca acgccagctg cgccatcggt ccgttcttcc gctgttcga cgagaccttc     960 ggcctggacg acgtccgttc ggccgaggtc gagctgaaga tcaccggccg cgacaacttc    1020
gtgctcgacg gcaagtcgaa catgagcctg atcagccgcg acccggccgt gctggccgga    1080
caggcctatg gcaagcagca ccagtatccg gacggctttg ctttgttcct gggcaccatg    1140
ttcgccccga tccaggaccg cgacaccccc ggccagggtt tcacccacaa ggtcggcgac    1200
cgcgtgcgtg tctcgacgcc gaagctgggc gtgctcgaga cgaagtcac cacctgcgac    1260 aaggccaagc cgtggacgtt cggcatctcg gccctgatcc gcaacctggc cggccgcggc    1320
ctcctctaa                                                           1329

<210> SEQ ID NO 46
<211> LENGTH: 442
<212> TYPE: PRT
<213> ORGANISM: Caulobacter crescentus

<400> SEQUENCE: 46
```

```
Met Val Cys Arg Arg Leu Leu Ala Trp Thr Ala Arg Ala Arg Glu Ala
1               5                   10                  15

Glu Asp Phe Ala Leu Val Arg Gln Pro Thr Cys Arg Pro His Met Leu
            20                  25                  30

Ala Leu Pro Ser Ala Asp Glu Arg Ala Pro Pro Thr Val Ser Ala Leu
        35                  40                  45

Gln Thr Leu Glu Phe Trp Gly Asp Ala Val Gly Val Ser Glu Phe
50                  55                  60

Leu Pro Glu Asp Trp Lys Ala Ala Thr Leu Leu Gly Arg Ile Asp Phe
65                  70                  75                  80

Gly Glu Gly Pro Thr Pro Val Leu Val Arg Gly Gly Arg Val Glu Asp
                85                  90                  95

Val Ser Lys Ile Ala Pro Thr Val Ala Asp Leu Met Asn Ala Phe Gln
                100                 105                 110

Pro Gly Ala Val Ile Pro Arg Gly Glu Asp Lys Gly Pro Leu Glu Ala
        115                 120                 125

Leu Asp Ile Arg Pro Val Trp Glu Asp Pro Asp Gly Ala Ala Pro Val
        130                 135                 140

Lys Leu Leu Ala Pro Val Asp Leu Gln Cys Leu Lys Ala Ala Gly Val
145                 150                 155                 160

Thr Phe Ala Val Ser Thr Leu Glu Arg Val Ile Glu Glu Arg Ala Arg
                165                 170                 175

Gly Asp Ala Gly Glu Ala Leu Lys Ile Arg Thr Leu Leu Ala Glu Arg
            180                 185                 190

Met Gly Gly Asp Leu Lys Ser Val Glu Pro Gly Ser Gln Gly Ala Gln
        195                 200                 205

Arg Leu Lys Asp Ala Leu Ile Ala Asp Gly Leu Trp Ser Gln Tyr Leu
210                 215                 220

Glu Val Ala Ile Gly Pro Asp Ala Glu Ile Phe Thr Lys Gly Pro Thr
225                 230                 235                 240

Leu Ser Ser Met Gly Trp Gly Asp Gln Val Gly Val Arg Tyr Asp Ser
                245                 250                 255

His Trp Asn Asn Pro Glu Pro Glu Val Val Leu Leu Cys Asp Gly Ser
            260                 265                 270

Gly Leu Ile Arg Gly Ala Ala Leu Gly Asn Asp Val Asn Leu Arg Asp
        275                 280                 285

Phe Glu Gly Arg Ser Ala Leu Leu Leu Ser Lys Ala Lys Asp Asn Asn
        290                 295                 300

Ala Ser Cys Ala Ile Gly Pro Phe Phe Arg Leu Phe Asp Glu Thr Phe
305                 310                 315                 320

Gly Leu Asp Asp Val Arg Ser Ala Glu Val Glu Leu Lys Ile Thr Gly
                325                 330                 335

Arg Asp Asn Phe Val Leu Asp Gly Lys Ser Asn Met Ser Leu Ile Ser
            340                 345                 350

Arg Asp Pro Ala Val Leu Ala Gly Gln Ala Tyr Gly Lys Gln His Gln
        355                 360                 365

Tyr Pro Asp Gly Phe Ala Leu Phe Leu Gly Thr Met Phe Ala Pro Ile
370                 375                 380

Gln Asp Arg Asp Thr Pro Gly Gln Gly Phe Thr His Lys Val Gly Asp
385                 390                 395                 400

Arg Val Arg Val Ser Thr Pro Lys Leu Gly Val Leu Glu Asn Glu Val
                405                 410                 415
```

```
Thr Thr Cys Asp Lys Ala Lys Pro Trp Thr Phe Gly Ile Ser Ala Leu
        420                 425                 430

Ile Arg Asn Leu Ala Gly Arg Gly Leu Leu
        435                 440

<210> SEQ ID NO 47
<211> LENGTH: 578
<212> TYPE: DNA
<213> ORGANISM: Corynebacterium glutamicum

<400> SEQUENCE: 47
aaattcctgt gaattagctg atttagtact tttcggaggt gtctattctt accaaatcgt      60
caagttgtgg gtagagtcac ctgaatatta attgcaccgc acgggtgata tatgcttatt     120
tgctcaagta gttcgaggtt aagtgtattt taggtgaaca aatttcagct tcgggtagaa     180
gactttcgat gcgcttcaga gcttctattg ggaaatctga caccacttga ttaaatagcc     240 taccccgaa ttgggggatt ggtcattttt tgctgtgaag gtagttttga tgcatatgac      300
ctgcgtttat aaagaaatgt aaacgtgatc agatcgatat aaaagaaaca gtttgtactc     360
aggtttgaag cattttctcc gattcgcctg gcaaaaatct caattgtcgc ttacagtttt     420
tctcaacgac aggctgctaa gctgctagtt cggtggccta gtgagtggcg tttacttgga     480
taaaagtaat cccatgtcgt gatcagccat tttgggttgt ttccatagca atccaaaggt     540
ttcgtctttc gataccatt caaggagcct tcgcctct                              578
```